US012257184B2

(12) United States Patent
LaBombard

(10) Patent No.: US 12,257,184 B2
(45) Date of Patent: Mar. 25, 2025

(54) OCULAR DEVICE AND DRUG DELIVERY SYSTEM, WITH CASE

(71) Applicant: Denis LaBombard, Georgetown, MA (US)

(72) Inventor: Denis LaBombard, Georgetown, MA (US)

( * ) Notice: Subject to any disclaimer, the term of this patent is extended or adjusted under 35 U.S.C. 154(b) by 748 days.

(21) Appl. No.: 17/076,634

(22) Filed: Oct. 21, 2020

(65) Prior Publication Data
US 2021/0121324 A1 Apr. 29, 2021

Related U.S. Application Data

(60) Provisional application No. 62/925,695, filed on Oct. 24, 2019.

(51) Int. Cl.
| | |
|---|---|
| *A61F 9/00* | (2006.01) |
| *C08L 23/08* | (2006.01) |
| *C08L 23/0853* | (2025.01) |
| *C08L 23/12* | (2006.01) |

(Continued)

(52) U.S. Cl.
CPC ........ *A61F 9/0017* (2013.01); *C08L 23/0853* (2013.01); *C08L 23/12* (2013.01); *C08L 71/02* (2013.01); *A61F 2210/0004* (2013.01); *A61F 2250/0004* (2013.01); *A61F 2250/0068* (2013.01); *A61K 45/06* (2013.01)

(58) Field of Classification Search
None
See application file for complete search history.

(56) References Cited

U.S. PATENT DOCUMENTS

| | | |
|---|---|---|
| 772,028 A | 10/1904 | Carpenter |
| 2,347,488 A | 4/1944 | Lawlor et al. |
| 3,186,540 A | 6/1965 | Breger |

(Continued)

FOREIGN PATENT DOCUMENTS

| | | |
|---|---|---|
| EP | 0 443 809 A2 | 8/1991 |
| JP | 2012-528695 A | 11/2012 |

(Continued)

OTHER PUBLICATIONS

International Search Report and Written Opinion of PCT/US2020/056700 dated May 19, 2021 titled "Ocular Device and Drug Delivery System, With Case".

(Continued)

*Primary Examiner* — Dominic Lazaro
(74) *Attorney, Agent, or Firm* — Hamilton, Brook, Smith & Reynolds, P.C.

(57) ABSTRACT

An ocular device for placement under an eyelid that includes a plate with a back surface having at least one protrusion having a convex contact surface to contact the sclera of the eye and to provide an offset space. The plate can be connected to an elongated support member. The ocular device can deliver a material to an eye of a user, including, for example, a pharmaceutically active agent. A case for holding and dispensing an ocular device includes a well configured to retain fluid, a stabilizer, and a lid. The lid is connected to the well and rotatable between a position covering the well and a position with the well uncovered. The lid can have a port for adding fluid to the well, and a receiver, which can hold an ocular device, can project from the lid.

67 Claims, 45 Drawing Sheets

(51) Int. Cl.
*C08L 71/02* (2006.01)
*A61K 45/06* (2006.01)

(56) References Cited

U.S. PATENT DOCUMENTS

| | | | |
|---|---|---|---|
| 3,220,960 A | 11/1965 | Wichterle et al. |
| 3,302,646 A | 2/1967 | Behney |
| 3,310,235 A | 3/1967 | Zbinden et al. |
| 3,416,530 A | 12/1968 | Ness |
| 3,618,604 A | 11/1971 | Ness |
| 3,630,200 A | 12/1971 | Higuchi |
| 3,710,795 A | 1/1973 | Higuchi et al. |
| 3,710,796 A | 1/1973 | Neefe |
| 3,828,777 A | 8/1974 | Ness |
| 3,845,201 A | 10/1974 | Haddad et al. |
| 3,867,519 A | 2/1975 | Michaels |
| 3,903,880 A | 9/1975 | Higuchi |
| 3,920,805 A | 11/1975 | Roseman |
| 3,933,411 A | 1/1976 | Winner |
| 3,937,680 A | 2/1976 | de Carle |
| 3,944,347 A | 3/1976 | Barkdoll et al. |
| 3,948,871 A | 4/1976 | Butterfield, Jr. et al. |
| 3,949,021 A | 4/1976 | Kunitomo et al. |
| 3,950,315 A | 4/1976 | Cleaver |
| 3,959,102 A | 5/1976 | Wajs et al. |
| 3,961,628 A | 6/1976 | Arnold |
| 3,962,414 A | 6/1976 | Michaels |
| 3,963,025 A | 6/1976 | Whitaker et al. |
| 3,973,837 A | 8/1976 | Page |
| 3,973,838 A | 8/1976 | Page |
| 3,986,510 A | 10/1976 | Higuchi et al. |
| 3,993,071 A | 11/1976 | Higuchi et al. |
| 3,995,635 A | 12/1976 | Higuchi et al. |
| 4,014,335 A | 3/1977 | Arnold |
| 4,057,619 A | 11/1977 | Higuchi et al. |
| 4,095,712 A | 6/1978 | Perrella |
| 4,135,514 A | 1/1979 | Zaffaroni et al. |
| 4,164,559 A | 8/1979 | Miyata |
| 4,179,497 A | 12/1979 | Cohen et al. |
| 4,186,184 A | 1/1980 | Zaffaroni |
| 4,190,642 A | 2/1980 | Gale et al. |
| 4,201,210 A | 5/1980 | Hughes et al. |
| 4,287,175 A | 9/1981 | Katz |
| 4,327,725 A | 5/1982 | Cortese et al. |
| 4,343,787 A | 8/1982 | Katz |
| 4,418,991 A | 12/1983 | Breger |
| 4,484,922 A | 11/1984 | Rosenwald |
| 4,540,417 A | 9/1985 | Poler |
| 4,592,752 A | 6/1986 | Neefe |
| 4,652,099 A | 3/1987 | Lichtman |
| 4,730,013 A | 3/1988 | Bondi et al. |
| 4,889,693 A | 12/1989 | Su et al. |
| 5,098,443 A | 3/1992 | Parel et al. |
| 5,137,728 A | 8/1992 | Bawa |
| 5,147,647 A | 9/1992 | Darougar |
| 5,322,691 A | 6/1994 | Darougar et al. |
| 5,349,395 A | 9/1994 | Stoyan |
| 5,395,618 A | 3/1995 | Darougar et al. |
| 5,515,964 A | 5/1996 | Bauman |
| 5,723,132 A | 3/1998 | Tseng et al. |
| 5,756,044 A | 5/1998 | Mowrey-Mckee et al. |
| 5,773,019 A | 6/1998 | Ashton et al. |
| 5,835,187 A | 11/1998 | Martin |
| 5,989,579 A | 11/1999 | Darougar et al. |
| 6,001,386 A | 12/1999 | Ashton et al. |
| 6,217,896 B1 | 4/2001 | Benjamin |
| 6,241,355 B1 | 6/2001 | Barsky |
| 6,264,971 B1 | 7/2001 | Darougar et al. |
| 6,416,777 B1 | 7/2002 | Yaacobi |
| 6,669,950 B2 | 12/2003 | Yaacobi |
| 6,986,900 B2 | 1/2006 | Yaacobi |
| 7,004,584 B1 | 2/2006 | Meyers et al. |
| 7,094,226 B2 | 8/2006 | Yaacobi |
| 7,488,343 B2 | 2/2009 | O'Brien et al. |
| 7,866,814 B2 | 1/2011 | Ye et al. |
| 7,906,143 B1 | 3/2011 | Odidi et al. |
| 7,914,842 B1* | 3/2011 | Greenberg ........... H05K 3/0035 |
| | | 427/2.24 |
| 8,007,480 B2 | 8/2011 | Kawashiro et al. |
| 8,167,855 B2 | 5/2012 | Leahy et al. |
| 8,287,504 B2 | 10/2012 | Leahy et al. |
| 8,679,078 B2 | 3/2014 | Leahy et al. |
| 8,923,961 B2 | 12/2014 | Singh et al. |
| 8,939,948 B2 | 1/2015 | De Juan, Jr et al. |
| 9,095,412 B2 | 8/2015 | Badawai et al. |
| 9,149,619 B2 | 10/2015 | Isaacs et al. |
| 9,421,126 B2 | 8/2016 | Alster et al. |
| 9,750,636 B2 | 9/2017 | Rubin et al. |
| 9,937,073 B2 | 4/2018 | De Juan, Jr. et al. |
| 2005/0134062 A1 | 6/2005 | Nigam |
| 2008/0024095 A1 | 1/2008 | Lampinen |
| 2009/0162417 A1 | 6/2009 | Eells |
| 2010/0226962 A1 | 9/2010 | Rodstrom et al. |
| 2010/0233241 A1 | 9/2010 | Leahy et al. |
| 2012/0109082 A1* | 5/2012 | Leahy ................. A61F 9/0017 |
| | | 604/294 |
| 2013/0178933 A1 | 7/2013 | Serrano Olmedo et al. |
| 2017/0056242 A1* | 3/2017 | Alster ................... A61K 31/58 |

FOREIGN PATENT DOCUMENTS

| | | |
|---|---|---|
| JP | 2013-545521 A | 12/2013 |
| JP | 2014-530044 A | 11/2014 |
| WO | WO 93/19707 | 10/1993 |
| WO | 2018205022 A1 | 11/2018 |
| WO | 2021081117 A2 | 4/2021 |

OTHER PUBLICATIONS

Atchison et al., "Eye Shape in Emmetropia and Myopia," Investigative Ophthalmology & Visual Science, Oct. 2004, vol. 45, No. 10, Association for Research in Vision and Ophthalmology, pp. 3380-3386.

Bekerman et al., Research Article, "Variations in Eyeball Diameters of the Healthy Adults," Journal of Ophthalmology, vol. 2014, Article ID 503645, pp. 1-5.

Bentivoglio et al., "Analysis of Blink Rate Patterns in Normal Subjects," Movement Disorder Society, Movement Disorders, vol. 12, No. 6, 1997. pp. 1028-1034.

Brazel et al., Chapter 19, "The Cost of Optimal Drug Delivery: Reducing and Preventing the Burst Effect in Matrix Systems," Svenson; Carrier-Based Drug Delivery, ACS Symposium Series; American Chemical Society: Washington, DC, 2004, pp. 267-282.

Brecher, "Graphical Representation of Stereochemical Configuration," Pure Appl. Chem., vol. 78, No. 10, pp. 1897-1970, 2006.

Brecher, "Graphical Representation Standards for Chemical Structure Diagrams," Pure Appl. Chem., vol. 80, No. 2, pp. 277-410, 2008.

Castelhano et al., "Stable Individual Differences Across Images in Human Saccadic Eye Movements," Canadian Journal of Experimental Psychology 2008, vol. 62, No. 1, pp. 1-14.

Findlay et al., "Human saccadic eye movements," Scholarpedia 7(7): 5995, Aug. 1, 2012, 10 pages.

Francis et al., "Lower eyelid tensometry in younger and older normal subjects," Nature Publishing Group, Eye (2006) 20, pp. 166-172.

Hashemi et al., "White-to-white corneal diameter distribution in an adult population," Journal of Current Ophthalmology, 27 (2015), pp. 21-24.

Huang et al., Review, "On the importance and mechanisms of burst release in matrix-controlled drug delivery systems," Journal of Controlled Release, 73 (2001), pp. 121-136.

Khan et al., "Defining the Limits of Normal Conjunctival Fornix Anatomy in a Healthy South Asian Population," American Academy of Opthalmology, Opthalmology, vol. 121, No. 2, Feb. 2014, pp. 492-497.

Laurutis et al., "The Vestibulo-Ocular Reflex During Human Saccadic Eye Movements," J. Physiol. (1986), 373, pp. 209-233.

(56) References Cited

OTHER PUBLICATIONS

Mircioiu et al., Review, "Mathematical Modeling of Release Kinetics from Supramolecular Drug Delivery Systems," Pharmaceutics 2019, 11, 140.
Mishima et al., "Determination of tear vol. and tear flow," Investigative Opthalmology, vol. 5, No. 3, Jun. 1966, pp. 264-276.
Ora Clinical, "It is Time to Think About the Blink," Ora, Inc., Jun. 13, 2011; https://www.oraclinical.com/resource/it-is-time-to-think-about-the-blink/2019, pp. 1-8.
Ousler et al., "Blink patterns and lid-contact times in dry-eye and normal subjects," Clin. Ophthalmol. 2014; 8: pp. 869-874.
Quaia, et al., "Three-Dimensional Rotations of the Eye," Chapter for Adler's Physiology of the Eye, 10th Edition. Kaufman & Alm, Eds., May 22, 2001, 22 pages.
Robinson, "The Mechanics of Human Saccadic Eye Movement," J. Physiol. (1964), 174, pp. 245-264.
Sagar Kishor Savale, "Drug release kinetics and mathematical models," Department of Pharmacy (Pharmaceutics), 2015-2016, May 19, 2016, 51 pages.
Vasanthakumar et al., "Anthropometric Analysis of Palpebral Fissure Dimensions and its Position in South Indian Ethnic Adults," Oman Med J. Jan. 2013; 28(1): pp. 26-32.
Vojnikovic et al., "Curvature Analyses of the Corneal Front and Back Surface," Coll. Antropol. 37 (2013) Suppl. 1: pp. 93-96.
Doughty MJ, Laiquzzaman M, Oblak E, Button N.; (2002) "The tear (lacrimal) meniscus height in human eyes: a useful clinical measure or an unusable variable sign?" Cont Lens Anterior Eye. Jun. 2002; 25(2):57-65.
Almeida, et al., "Sustained release from hot-melt extruded matrices based on ethylene vinyl acetate and polyethylene oxide," European Journal of Pharmaceutics and Biopharmaceutics 82 (2012) 526-533.
International Preliminary Report on Patentability for PCT/US2020/056700 dated May 5, 2022.
Abelson, "It's Time to Think About the Blink," https://www.reviewofophthalmology.com/article/its-time-to-think-about-the-blink Jun. 13, 2011.
Kumari, et al., "Ocular Inserts—Advancement in Therapy of Eye Diseases," J Adv Pharm Technol Res., 1(3): 291-296 (Jul.-Sep. 2010).
Lacrisert® Instructions for Use; "3 Simple Steps for Placement," Distributed by: Bausch + Lomb, a division of Valeant Pharmaceuticals North America LLC Bridgewater, NJ 08807 USA. Manufactured by: DPT Lakewood, Inc. Lakewood, NJ 08701 USA, Mar. 27, 2014.
Peet, "Spacecraft and Aircraft Dynamics," Lecture 9: 6DOF Equations of Motion, Illinois Institute of Technology, 24 pages, Sep. 27, 2010.
Tatke, et al., "Melt-Cast Films Significantly Enhance Triamcinolone Acetonide Delivery to the Deeper Ocular Tissues," *Pharmaceutics* 2019, 11, 158, 14 pages (published Apr. 2, 2019).
Allen et al., "Lateral Displacement of the Intact Mandibular Condyle: A Report of Five Cases," British Journal of Oral Surgery, 7 pages, 1969.
Shaw, A., "Eyelid pressure on the cornea", Thesis, Institute of Health of Biomedical Innovation School of Optometry, Queensland University of Technology, Brisbane, Australia , Nov. 1, 2009.
Invitation to Pay Additional Fees and, Where Applicable, Protest Fee, issued for International Application No. PCT/US2020/056700, entitled "Ocular Device and Drug Delivery System, With Case," mailed on Feb. 11, 2021.
Cantin, "PEO Hot Melt Extrudes for Controlled Drug Delivery," Human Health and Pathology, Université du Droit et de la Santé—Lille II, 2016. English. NNT:2016LIL2S035.
"Factors Influencing the Solubility of Drugs: Introduction; Introduction," The Pharmaceutics and Compounding Laboratory, UNC Eshelman School of Pharmacy, retrieved from the Internet on Mar. 1, 2021; https://pharmlabs.unc.cdu/labs/solubility/intro.htm.
Schneider, et al., Corrigendum to Applications of Ethylene Vinyl Acetate Copolymers (EVA) in Drug Delivery Systems' *Journal of Controlled Release:* 278 (2018) 156-158.
Sigma-Aldrich Product Specification, downloaded Mar. 28, 2020.

\* cited by examiner

SECTION A-A

SECTION B-B

SECTION C-C

SECTION D-D

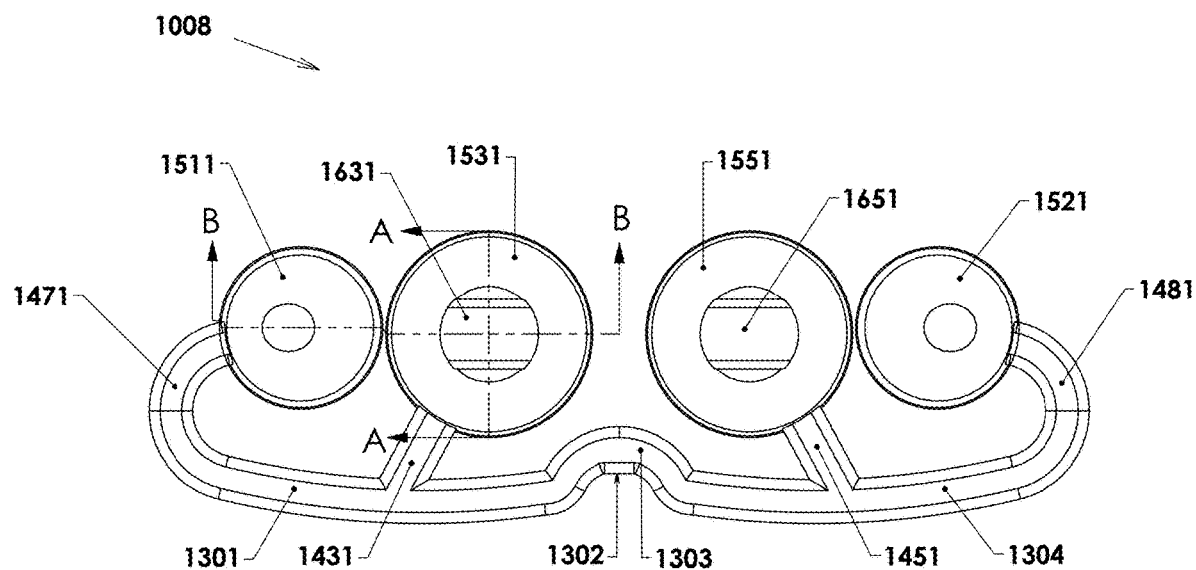
FIG. 20A
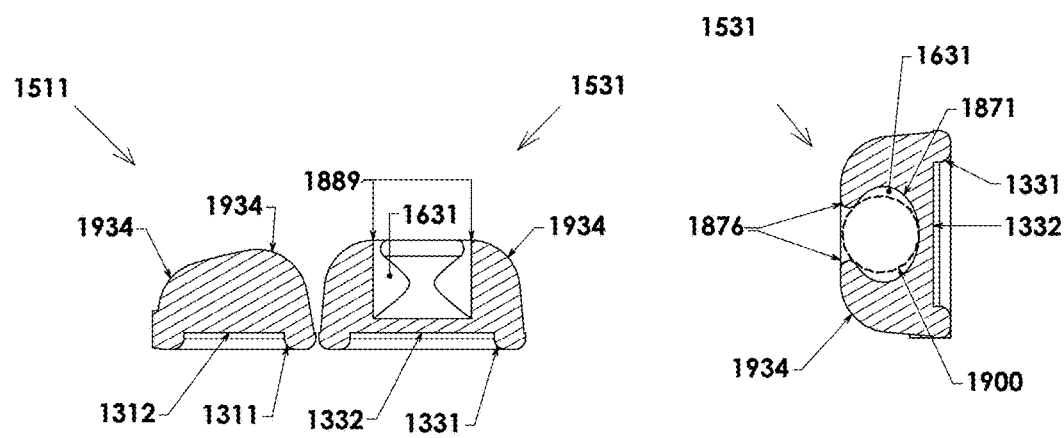
FIG. 20B
SECTION B-B
FIG. 20C
SECTION A-A

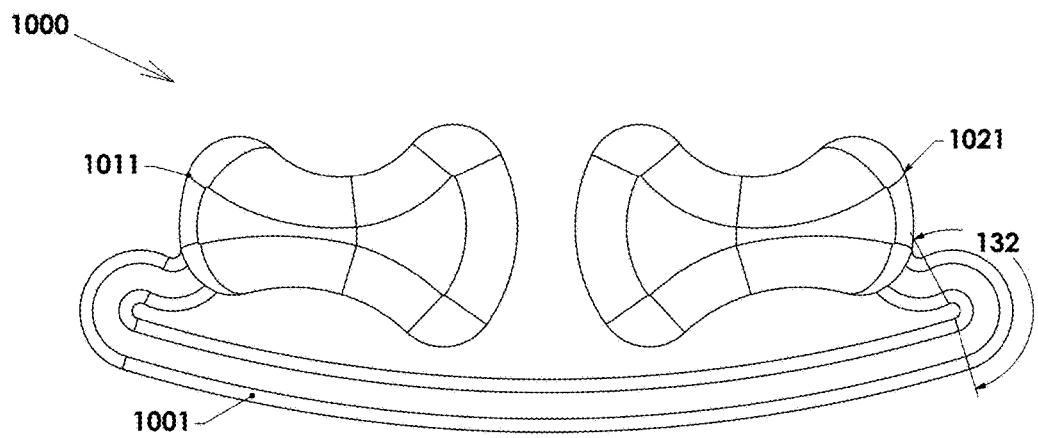
FIG. 22A
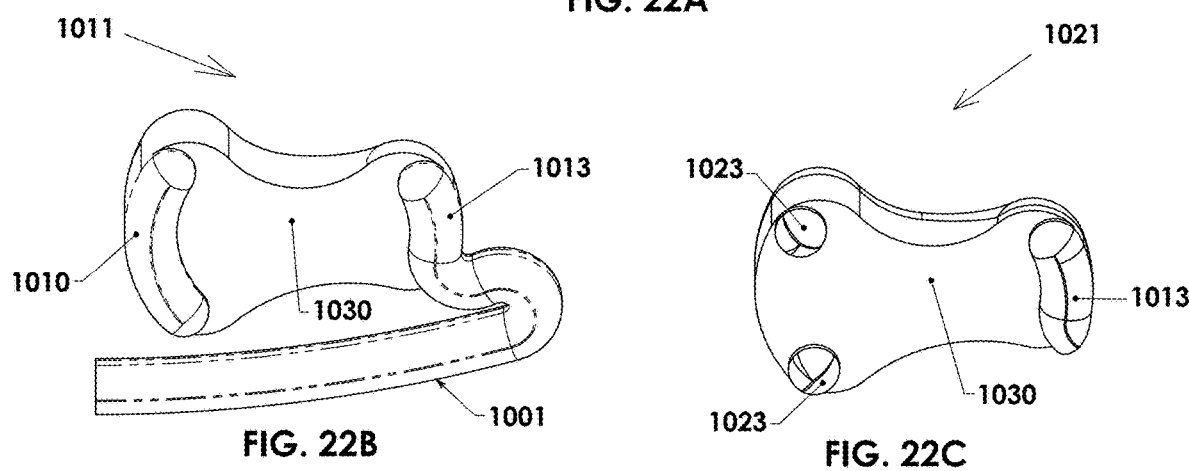
FIG. 22B
FIG. 22C
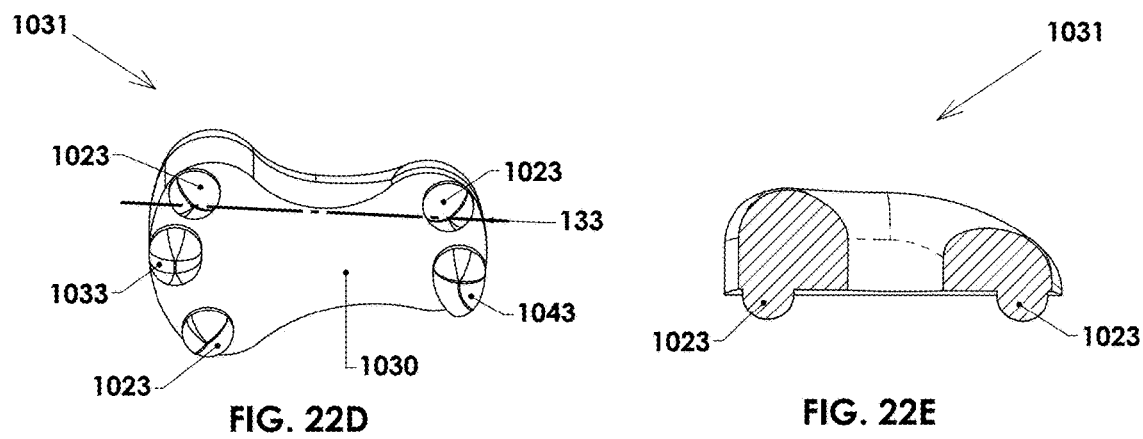
FIG. 22D
FIG. 22E

SECTION A-A

SECTION A-A

OCULAR DEVICE AND DRUG DELIVERY SYSTEM, WITH CASE

RELATED APPLICATION(S)

This application claims the benefit of U.S. Provisional Application No. 62/925,695, filed on Oct. 24, 2019. The entire teachings of the above application(s) are incorporated herein by reference.

BACKGROUND

Devices for delivery of medication into the eye have a long history for numerous purposes. An early example is a pair of spectacles with a medication chamber to be worn over the eyes for the application and delivery of medication into the eye for a set period of time. This example demonstrates a clinical device to treat ocular physiology by direct contact.

Over time, the art has progressed to include devices and/or materials with therapeutic agents intended to be placed independently within the ocular anatomical space. Examples include constructs and drug delivery systems that can provide a uniform drug delivery rate to the eye and design geometry for such purposes, intended to be placed and retained in some manner within the ocular anatomical space. This historical migration to apply clinical therapy directly has generated multiple therapeutic modalities.

The evolution of ocular devices has progressed over time to include smaller and more complicated devices. Many of these devices require that the device be placed within the ocular space in a specific orientation. For example, a contact lens is to be placed on an eyeball with one surface of the lens against the eye and not the other. In general, users identify the surface of the contact lens to apply to the eye. For an ocular device designed for placement in a particular orientation, it would be advantageous for a case to denote to the user, simply and clearly, the preferred orientation for the ocular device. Current cases for ocular devices, such as contact lenses, identify to a user a left eye device and a right eye device.

A user may not be able to determine the correct orientation of ocular devices that are smaller and more complex than a contact lens. Ocular devices that are not placed on the cornea of an eye present challenges for correct placement and orientation. Without correct placement and orientation, these devices can function improperly or sub-optimally.

SUMMARY

Ocular devices can be useful for placement in an eye. Contact lenses are ocular devices placed on the surface of an eyeball. An ocular device can be placed under an eyelid. The eyelid can be the upper or the lower eyelid. A person with dry eye may have a diminished ability to form tear meniscus and may have decreased tear volume, and tear fluid can decrease with age. A comfortable adaptive hydrophilic (water attracting) ocular device placed under an eyelid can be beneficial because, for example, it can collect tear fluid and, in doing so, increase the amount and residence time of tear fluid. An ocular device can include features configured to retain tear fluid, may be capable of retaining a significant volume of tear fluid, which is desirable, for example, in an aging population and in users with dry eye, who experience difficulty achieving sufficient ocular lubrication. Ocular devices for placement under an eyelid can be used, for example, for delivering a therapeutic agent to the eye. It is advantageous to place an ocular device under an eyelid that can adapt to patient-to-patient variability of ocular anatomical structures and kinetic motions of the eye, including variability that can result from factors such as age, health, and genetics or ancestral factors.

An ocular device for placement under an eyelid includes a plate. The plate includes a back surface, the back surface having at least one protrusion having a contact surface to contact the sclera of the eye and to provide an offset space between the sclera and the back surface of the plate. The insertion of the device into the eye further offsets the eyelid in relation to the sclera.

The plate can be connected to an elongated support member of flexible material with a first end and a second end. The plate can be connected proximate to the first end of the elongated support member. The ocular device can further include a plate connected proximate to the second end of the elongated support member.

A flexible connector can connect at least one plate to the elongated support member. The connection between the flexible connector and the elongated support member can be configured to be located adjacent to a canthus of an eye, when the ocular device is under the eyelid. The contact surface can form a boundary around the offset space.

At least one protrusion can be a complete annulus. The at least one protrusion can be toroidal.

The back surface of the plate can have at least three protrusions having a contact surface to contact the sclera of an eye and to provide an offset space between the sclera and the back surface of the plate. The contact surface of the at least one protrusion on the back surface can be a convex contact surface.

Each plate includes a front surface, on the other side of the plate from the back surface. The front surface can have at least one protrusion having a contact surface to contact the sclera of the eye and to provide an offset space between the sclera and the front surface of the plate. The contact surface of the at least one protrusion on the front surface can be a convex contact surface.

The perimeter of at least one plate of an ocular device can be curved.

At least one plate of an ocular device can extend laterally from an elongated support member.

The length of an elongated support member of an ocular device can be between about 3 millimeters and about 24 millimeters. The length of the elongated support member of an ocular device can be between about 3 millimeters and about 8 millimeters. The length of the elongated support member of an ocular device can be between about 4 millimeters and about 10 millimeters. The length of the elongated support member can be between about 6 millimeters and about 16 millimeters.

The elongated support member, the plate connected proximate to the first end of the elongated support member, and the plate connected proximate to the second end of the elongated support member can be substantially coplanar, flexibly interconnected, and configured to adapt to irregular surfaces.

At least one plate can be connected to the elongated support member of the ocular device between the first end and the second end of the elongated support member, the at least one plate being substantially coplanar with the elongated support member.

An ocular device can include at least three plates.

Each plate of an ocular device can be connected to an elongated support member by a flexible connector.

At least two plates of an ocular device can be connected to an elongated support member by a curved flexible connector and at least an additional two plates of the ocular device can be connected to the elongated support member by a substantially straight flexible connector.

The thickness from the front to the back of at least one of plate of an ocular device can decrease with distance from a central area of the ocular device.

Plates of an ocular device can be connected to the same side of an elongated support member.

An ocular device can include an elongated support member that is curved. An ocular device can include an elongated support member that has a smoothly curved outer surface.

An ocular device can include at least one plate that is substantially circular.

An ocular device can include at least one plate with a back surface in which the widest portion of the back surface of the at least one plate is about 2 millimeters to about 7 millimeters.

An ocular device can have a plate that is substantially circular. A substantially circular plate can have a diameter in a range of about 2 millimeters to about 7 millimeters.

An ocular device can have an elongated support member with an arch portion and outer sweep portions, each sweep portion extending from the arch portion. An arch portion of an elongated support member can have a radius of curvature between about 0.0 millimeters and about 6.0 millimeters. An arch portion of an elongated support member can be a segmental arch that is positioned in the central area of the ocular device, between the ends of the elongated support member.

An ocular device can have a substance to be delivered to an eye. A substance to be delivered to the eye can be in at least one plate of an ocular device. At least one plate of an ocular device can provide at least one pocket that is for holding a substance to be delivered to the eye. A pocket in a plate can be cylindrical. A substance to be delivered to an eye can be in a pocket in a plate. A plate can have an opening to a pocket, with the pocket configured to receive, through the opening, a substance to be delivered to the eye.

An insert that contains the substance to be delivered to the eye can be placed in a pocket of a plate of an ocular device.

An ocular device can have a retention element to retain an insert in a pocket. A retention element can, for example, be a sealing membrane bonded to an ocular device, to an insert, or to the ocular device and the insert. A sealing membrane that serves as a retention element can include an aperture. A lip at an opening of a pocket can serve as a retention element. An opening to a pocket can be substantially in the shape of a polygon. An opening to a pocket can be substantially in the shape of a hexagon.

There can be an orifice in a plate of an ocular device, the ocular device being configured to dispense, through the orifice to an eye, a substance from an insert in the plate. The orifice can be different from the opening and provide a dual direction drug delivery system.

At least a portion of an ocular device can be formed from polymeric material.

An ocular device for placement under an eyelid includes an elongated support member of flexible material and at least one plate connected to the elongated support member. The plate has a back surface with at least one protrusion having a contact surface to contact the sclera of the eye and to provide an offset space between the sclera and the back surface of the plate. The contact surface can be convex. The elongated support member and the plate can be substantially coplanar. The at least one plate can be connected to the elongated support member proximate to an end of the elongated support member. The ocular device can have at least two plates connected to the elongated support member proximate to an end of the elongated support member, the elongated support member and the plates being substantially coplanar. The ocular device can include at least three plates connected to the elongated support member.

An ocular device for placement under an eyelid to deliver material to an eye includes an elongated support member, a plate connected proximate to each end of the elongated support member and substantially coplanar with the elongated support member, each plate comprising a back surface, the back surface having at least one protrusion having a contact surface to contact the sclera of the eye and to provide an offset space between the sclera and the back surface of the plate. The contact surface can be convex. The ocular device can further include a pharmaceutically active agent. The pharmaceutically active agent can be disposed within at least one plate.

An ocular device for placement under an eyelid can deliver material such as a pharmaceutically active agent to an eye by forming at least a portion of the ocular device of pharmaceutically active agent blended with other material.

An ocular device can include at least one plates that has a pocket capable of receiving pharmaceutically active agent. Pharmaceutically active agent can be in the pocket of a plate of the ocular device. A removable insert containing pharmaceutically active agent can be in at least one of the pockets. The plate can further comprise a retention element to retain the insert in the pocket.

An ocular device for placement under an eyelid of an eye including a sclera contact surface with at least three points configured to contact a sclera of an eye, a remote surface configured to be maintained remote from the sclera of the eye by the at least three contact points, the remote surface and the at least three contact points providing an offset space configured to retain a tear fluid. The ocular device can further include pharmaceutically active agent for delivery to the eye. The ocular device can be placed under an eyelid, and the pharmaceutically active agent can be delivered to the eye by the tear fluid.

An ocular device for placement under an eyelid of an eye can have a contact surface for contacting the sclera that is less than about 20% of the surface area of the remote surface. The ocular device can be flexible and adaptive to the sclera contact surface.

A method for delivering a pharmaceutically active agent to an eye including providing an ocular device having an elongated support member, a plate connected proximate to each end of the elongated support member and substantially coplanar with the elongated support member, at least one plate having a back surface with at least one protrusion having a contact surface to contact the sclera of the eye and to provide an offset space between the sclera and the back surface of the plate, adding a pharmaceutically active agent to at least one of the plates, and placing the ocular device under an eyelid of the eye. The contact surface can be convex. Adding the pharmaceutically active agent to at least one of the plates of the ocular device can include disposing the pharmaceutically active agent in at least one pocket in at least one of the plates. Disposing the pharmaceutically active agent in the at least one pocket can include inserting an insert in the at least one pocket, the insert containing pharmaceutically active agent.

An ocular device can be placed under an eyelid with the back surface of at least one plate toward the sclera of the eye. The ocular device can be placed under the eyelid with the front surface of at least one plate toward the sclera of the eye. The ocular device can be placed under the eyelid with the elongated support member toward the fornix. The ocular device can be placed under the eyelid with at least one plate toward the fornix.

An insert for use with an ocular device or a method can comprise, consist essentially of, or consist of a composition comprising the pharmaceutically active agent and a pharmaceutically acceptable carrier. The pharmaceutically acceptable carrier can include a water-soluble polymer. The pharmaceutically acceptable carrier can include a water-insoluble polymer. The pharmaceutically acceptable carrier can form a matrix, and the pharmaceutically active agent can be dispersed within the matrix.

A composition comprises one or more pharmaceutically active agents; from about 20% to about 80% by weight of a water-insoluble polymer; and from about 20% to about 80% by weight of a water-soluble polymer. The composition can comprise from about 25% to about 70% by weight of water-insoluble polymer. The composition can comprise from about 40% to about 75% by weight of water-soluble polymer. The water-insoluble polymer of the composition can be ethylene vinyl acetate (EVA). The weight percent of vinyl acetate in the EVA can be 25% or greater. The water-soluble polymer of the composition can bepolyethylene oxide (PEO). The molecular weight of the PEO can be from about 100,000 to about 300,000. The water-insoluble polymer of the composition can have a melting temperature of about 99° C. or less. The water-soluble polymer of the composition can have a melting temperature of about 99° C. or less. The composition can have from about 0.5% to about 50% by weight of pharmaceutically active agent. Each of the one or more pharmaceutically active agents can have a melting temperature of greater than about 99° C. and be water-soluble. The one or more pharmaceutically active agents can be in the form of particles. The one or more pharmaceutically active agents can include ciprofloxacin, dexamethasone, olopatadine, pilocarpine, hyaluronic acid or hydroxypropylcellulose, or a pharmaceutically acceptable salt of the foregoing.

The composition can be formulated for ocular administration. The composition can be in the form of a semi-erodible polymer matrix. The composition can be formulated to provide controlled release of one or more pharmaceutically active agents.

A method of making a disclosed composition includes hot melt blending one or more pharmaceutically active agents, water-insoluble polymer, and water-soluble polymer to form a hot melt blend and cooling the hot melt blend to produce the composition. Hot melt blending can be performed at a temperature of less than about 99° C. Hot melt blending can be performed at a temperature below the melting temperature of the one or more pharmaceutically active agents.

A case for holding and dispensing an ocular device has a well configured to retain fluid, the well having an open top, a stabilizer connected to the well, a lid connected to the well, the lid rotatable between a position covering the open top of the well and a position with the well uncovered, the lid having a port in fluid communication with the interior of the well when the lid covers the open top of the well, and a receiver projecting from the lid and configured to receive and hold an ocular device proximate to the port, the receiver being within the well when the well is covered by the lid.

The receiver of a case can form a channel that is open on at least one side of the receiver. The channel can be open on two sides of the receiver, and the channel can be configured to enable the ocular device to be dispensed from either of the two sides of the receiver, maintaining the orientation of the dispensed ocular device. The channel can be shorter than the ocular device. The receiver can include a restraining element configured to hold the ocular device in a specific orientation. The restraining element can be a ridge.

The lid can be removably secured to the well when the lid is in the position covering the open top of the well, and the lid can be configured to extend past the well when the lid is in the position covering the open top of the well.

The case can include a latch for removably securing the lid in the position covering the open top of the well. The latch can be latch post and a key.

The lid can be connected to the well by a hinge formed of flexible material.

The stabilizer can form a ring that surrounds the well.

The well, stabilizer, lid, and receiver can be of unitary construction.

The port can be configured to permit fluid to enter the well when the lid is in the position covering the open top of the well. The port is of a length that is sufficient for the escape of gas from and the entry of fluid into the well.

The case can include a removable peel strip sealing the port.

The case can be composed of a high melt flow polypropylene material.

The case can have an ocular device in the case.

The case can include features for orienting the ocular device. Features for orienting the device can be tactile and visual features.

The case can be for holding and dispensing an ocular device, including an ocular device that is disclosed herein.

The receiver of the case can further include a restraining element. The restraining element can be a ridge.

A case for holding and dispensing an ocular device includes a well configured to retain fluid, the well having an open top, a stabilizer connected to the well, a lid connected to the well, the lid rotatable between a position covering the open top of the well and a position with the well uncovered, and a receiver projecting from the lid and configured to receive and hold an ocular device, the receiver being within the well when the well is covered by the lid.

The case can include a port. The port can be on the lid and in fluid communication with the interior of the well when the lid is in the position covering the open top of the well. An ocular device held by the receiver can be proximate to the port.

The port can be configured to permit liquid to enter the well through the port and flow across the ocular device when the lid is in the position covering the open top of the well.

A kit can be provided that includes an ocular device, a case, and material to administer to an eye of a user. The material can be a medication, a pharmaceutical, a drug, or a combination. The kit can include solution for wetting the ocular device.

A method of inserting into an eye of a user an ocular device held in a case by a receiver, the ocular device having a surface for contacting the sclera of the eye. The method includes positioning the case on a substantially flat location in front of the user with the surface of the ocular device to be in contact with the sclera oriented toward the user, rotating a lid covering the open top of a well of the case to remove the receiver from the well, and revealing the ocular device held by the receiver, removing the ocular device from the receiver while maintaining the orientation of the ocular device, and inserting the ocular device into the eye of the user under an eyelid.

The method can further include sterilizing the ocular device sealed in the well with the lid in the position covering the open top of the well.

The method can further include adding to the well a material to be administered to the eye of the user. The material can be added through the port.

The material can be added directly to the interior space of the well through the open top of the well.

The method can include removing a peel strip from the lid, and removal of the peel strip can unseal the port.

Before rotation of the lid, the lid can be covering the open top of the well and the port can be in fluid communication with the interior space of the well.

Removing the ocular device from the case can be achieved by a pulling hand to grasp a protruding portion of the ocular device from the right or left side of the receiver with the right hand or the left hand. In removing the ocular device, a pushing hand can be used to direct the protruding portion of the ocular device toward the pulling hand.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments. Descriptions of the drawings that identify a "front" view, "back" view, "top" view, and "bottom" view provide a frame of reference and are not intended as a limitation on the direction of use of what appears in the drawing.

FIG. 9A1 is a front view of an ocular device with the plates cut on a horizontal plane to reveal pockets.

FIG. 9A2 is a front view of the device of FIG. 9A1 with inserts aligned to be inserted into the pockets in the plates.

FIG. 20A is a front view of an ocular device.

FIG. 20B is a section view along line B-B of the ocular device of FIG. 20A.

FIG. 20C is a section view along line A-A of the ocular device of FIG. 20A.

FIG. 22A is a front view of an ocular device.

FIGS. 22B-22E illustrate plates with protrusions.

DETAILED DESCRIPTION

Descriptions of examples of ocular devices follow.

An example ocular device is configured to be placed in the eye. The front of the device is the surface of the device that is toward the eyelid. The back of the device is the surface that is toward the sclera of the eye. The device can optionally be configured so that the front or the back of the device can be toward the sclera of the eye.

Clinical Detail and Illustration of the Physical Geometries and Measures of the Eye, and the Eyelid.

Researchers studying eye anatomy have described a wide range of anatomy data variability across the human population.

Figure 1:
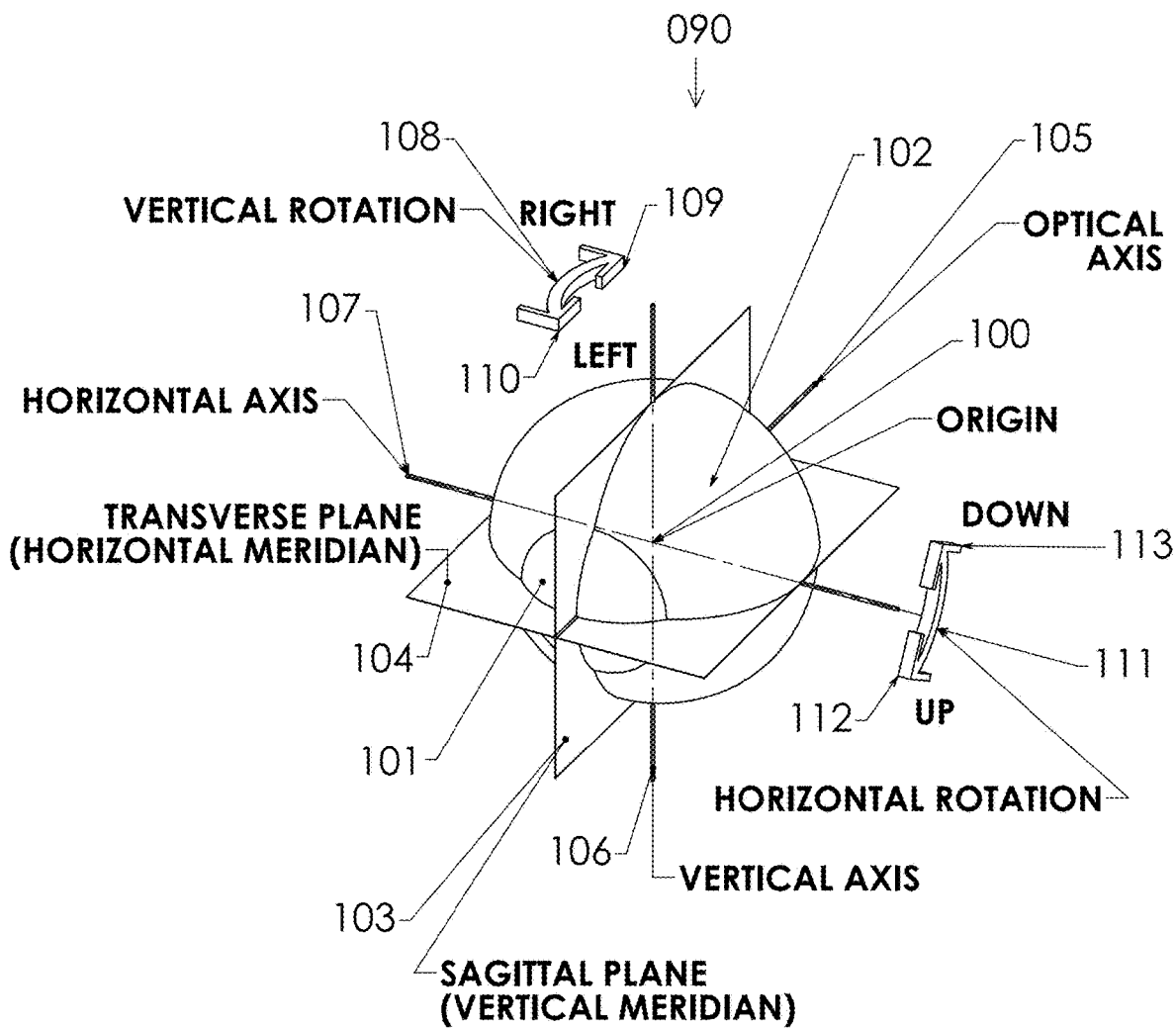
FIG. 1 is an isometric view of a three-dimensional (3D) model of an eyeball with normal focus (emmetropic) identifying a sagittal (vertical) plane, a transverse (horizontal) plane, and an optical axis as spatial references and showing degrees of freedom.

FIG. 1 is an isometric view of a three-dimensional (3D) "CAD" model of an emmetropic eyeball with normal focus (emmetropic) identifying a sagittal (vertical) plane, a transverse (horizontal) plane, and an optical axis as spatial references and showing degrees of freedom. The model includes eyeball, outer cornea, and outer scleral surfaces. The sclera or scleral surface is the white outer layer of the eyeball. The sclera is an opaque, fibrous, tough, protective outer layer of the eye ("white of the eye"), continuous with the cornea in the front of the eyeball and with the sheath covering the optic nerve at the back of the eye. Clinically defined section planes from which clinical imaging measurements have been taken across populations appear with the eyeball, along with an optical axis defining a focal length and kinematic axial rotation indicators defining the eye motion capability and the degree(s) of freedom of human eyeball visual gaze motion. The anatomical model is derived from representative clinical publication data. The retina is a thin layer of tissue that lines the eye on the inside, located near the optic nerve. The purpose of the retina is to receive light that the lens has focused, convert the light into neural signals, and send these signals on to the brain for visual recognition.

Eyeball 090 includes a cornea 101 and a sclera 102 showing the outer surface bounds of an emmetropic eye. The cornea 101 is the optical vision focus element comprised of spherical geometry with historical classical outer radius measure 7.7 mm and a diameter of generally 11.7 mm, which optically defines an optical "focus" axis ("X") 105 projecting an image on the retina. The sagittal (vertical) plane 103 and transverse (horizontal) plane 104 are perpendicular to each other, intersecting along the optical axis ("X") 105.

Defining the local origin, the three axes, and the centerline sectional planes using "6DOF" convention, vertical axis ("Z") 106 is perpendicular to horizontal axis ("Y") 107 and optical axis ("X") 105. Horizontal axis ("Y") 107 is also perpendicular to optical axis ("X"). Prescribed axes 105, 106, and 107 intersect singularly at local origin point 100, the nominal center point to the vision ocular anatomy. The sagittal plane (vertical meridian) 103 is created by vertical axis 106 and optical axis 105. The transverse plane (horizontal meridian) 104 is created by the horizontal axis 107 and optical axis 105. The sagittal plane 103 is perpendicular to the transverse plane 104 intersecting optical axis 105.

Further illustrated by FIG. 1 are the rotational movement capabilities of eyeball 090 as constrained by ocular fixation and muscle movement anatomy (not shown). Vertical axis rotation arrow 108 describes the left 110 and right 109 visual input effect of eyeball rotation about vertical ("Z") axis 106. Horizontal rotation arrow 111 describes the up 112 and down 113 visual input effect of eyeball rotation about the horizontal ("Y") axis 107. In combination, these gaze rotations define two degrees of rotational freedom of eyeball 090, about origin 100, sufficient to observe any object within the field of view.

While the internal optical focus structure of the eyeball has been demonstrated to be relatively consistent, the external width of the eyeball and optical axis length is shown to have a wide range of variability. This variability range defines curvature and surface shape of the non-optical sclera surfaces and adjoining support tissue.

Figure 2A:
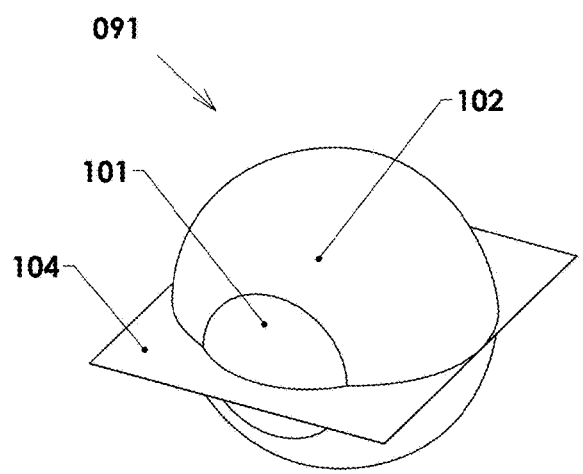
FIG. 2A is an isometric view of a model of an eyeball showing the surface of an emmetropic eye and a sagittal plane.

FIG. 2A is an isometric view of eyeball 091 including a cornea 101 and a sclera 102 showing the outer surface bounds of an emmetropic eye. The transverse (horizontal) plane 104 as shown in FIG. 1 defines the eyeball cross-section location of the remaining figures. The eyeball shown in FIG. 2A represents an emmetropic (normal) eyeball with measurements shown in Table 1.

Figure 2B:
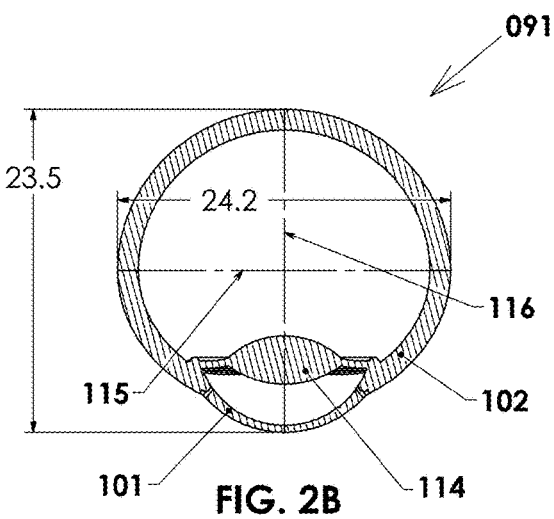
FIG. 2B is a transverse (horizontal) cross-sectional view of an eyeball illustrating measures of axial length and transverse width for an emmetropic eye corresponding to FIG. 2A.

FIG. 2B is a transverse (horizontal) cross-section view of emmetropic eyeball 091 shown in FIG. 2A. The figure shows internal optics eye anatomy including lens capsule and iris 114, cornea 101, and sclera 102. The optical axial length 116 of example eyeball 091 is 23.5 mm and the transverse (horizontal) width 115 is 24.2 mm, representing mean values of an "idealized" clinical eye model.

Figure 2C:
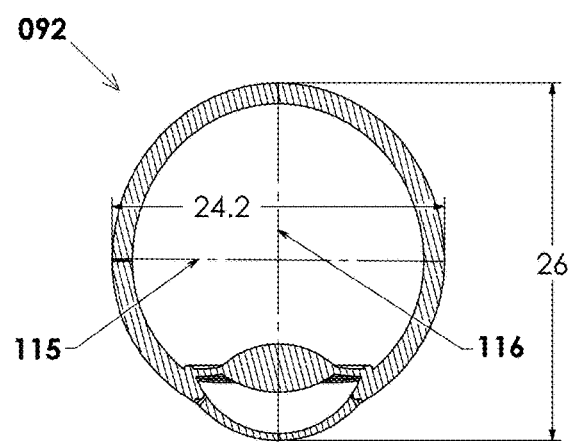
FIGS. 2C, 2D, 2E, and 2F are cross-sectional views of eyeballs that represent clinical assessments and observed anatomical measures of axial length and transverse width, as further summarized in Table 1.

FIG. 2C is a transverse (horizontal) cross-section view of myopic (near-sighted) eyeball 092, with optical axial length 116 of 26 mm and transverse (horizontal) width 115 of 24.2 mm, representing mean values of a myopic clinical eye model.

Figure 2D:
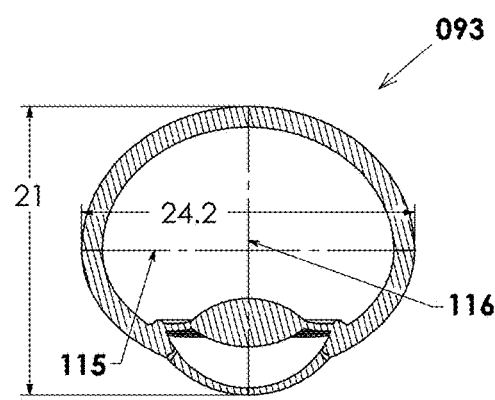

FIG. 2D is a transverse (horizontal) cross-section view of hypermetropia (far-sighted) eyeball 093, optical axial length 116 of 21 mm and transverse (horizontal) width 115 of 24.2 mm, representing typical mean values of a hypermetropia clinical eye model.

Figure 2E:
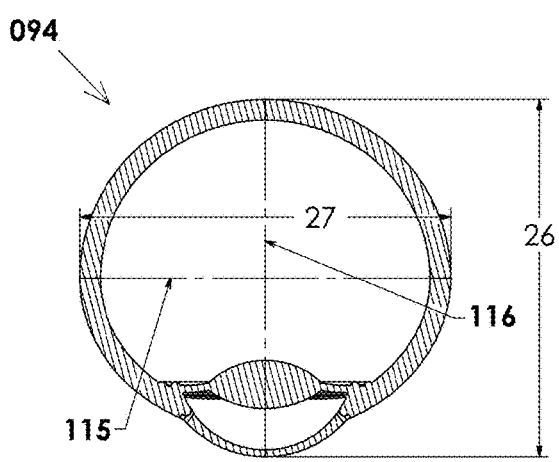

FIG. 2E is an isometric view of largest volume eyeball 094, with optical axial length 116 of 26 mm and transverse (horizontal) width 115 of 27 mm.

Figure 2F:
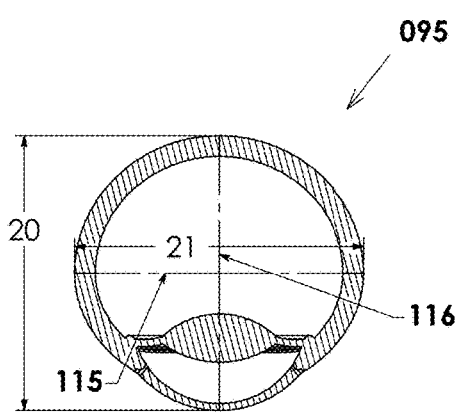

FIG. 2F is a transverse (horizontal) cross-section view of smallest volume eyeball 095, with optical axial length 116 of 20 mm and transverse (horizontal) width 115 of 21 mm.

The measures are shown within the illustration figures for comparison and understanding of surface shape and curve shape variability range as seen at the transverse (horizontal) plane cross-section meridian (FIG. 2A, 104) (see, Bekerman, I; Gottlieb, P; & Vaiman, M; (2014) "Variations in Eyeball Diameters of the Healthy Adults," Journal of Ophthalmology, vol. 2014, Article ID 503645, 5 pages, 2014 incorporated here by reference in its entirety).

TABLE 1

|  | ID# | Clinical Diagnosis | ID# | Axial (mm) | ID# | Transverse (mm) |
|---|---|---|---|---|---|---|
| FIGS. 2A and 2B | 091 | Emmetropic ('Normal') | 116 | 23.5 mm | 115 | 24.2 mm |
| FIG. 2C | 092 | Myopic ('Near Sighted') | 116 | 26 mm | 115 | 24.2 mm |
| FIG. 2D | 093 | Hypermetropia ('Far Sighted') | 116 | 21 mm | 115 | 24.2 mm |
| FIG. 2E | 094 | Largest (Volume) Eyeball | 116 | 26 mm | 115 | 27 mm |
| FIG. 2F | 095 | Smallest (Volume) Eyeball | 116 | 20 mm | 115 | 21 mm |
|  |  | Variability Range (mm) |  | 6 mm |  | 6 mm |

FIGS. 3A and 3B and FIGS. 4A to 4F illustrate clinical data and anatomy variability of eyelid size, shape, depth-to-fornix, width, and canthus-to-canthus opening across a human population based on studies in publications on the topic. The figures follow the "6DOF" nomenclature introduced in FIG. 1 and apply the nominal emmetropic clinical cornea and sclera measures used in FIGS. 2A and 2B to present the mean and variability range of eyelid data as described by clinical studies in publications.

Figure 3A:
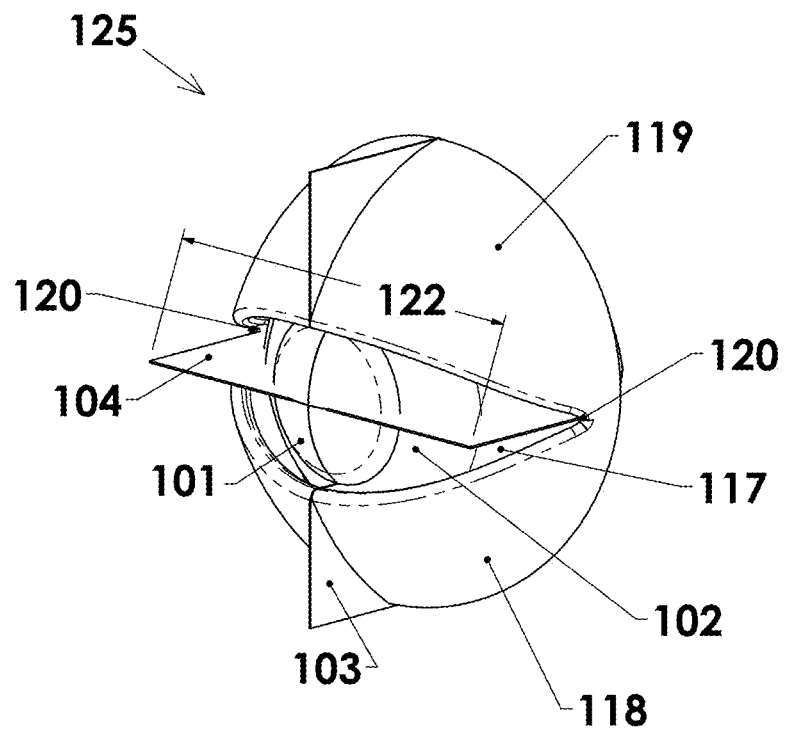
FIG. 3A is an isometric view of a representative eyeball and eyelid with no particular parameters.

FIG. 3A is an isometric view of a representative eyeball 125 with no particular parameters. Geometric control values are the ideal mean value of the representative clinical data of the cited publications. The figure includes cornea 101 and sclera 102, an upper eyelid 119, a lower eyelid 118, the conjunctiva tissue 117, the two canthi (corners) of the palpebral fissure where upper and lower eyelids meet 120, and the palpebral fissure width ("PFW") 122 along transverse (horizontal) plane 104 between canthi 120 that defines an upper eyelid 119 and a lower eyelid 118 geometry.

The sagittal (vertical) plane 103 and the transverse (horizontal) plane 104, as in FIG. 1, are perpendicular to each other, located and intersecting at the cornea 101 optical axis.

Figure 3B:
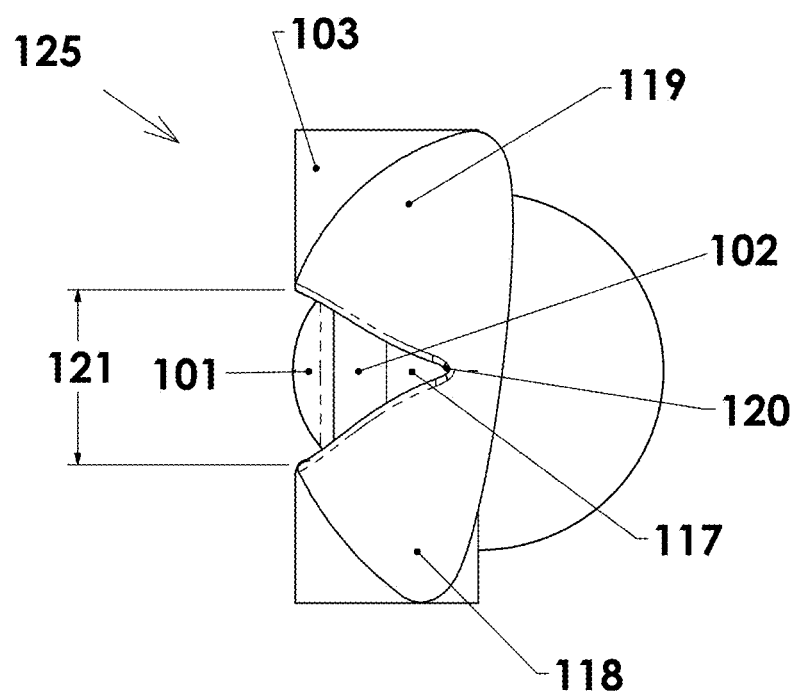
FIG. 3B is a side view of the eyeball and eyelid of FIG. 3A.

FIG. 3B is a side view of the eyeball 125 with eyelid anatomy of FIG. 3A, further illustrating the cornea 101, sclera 102, upper eyelid 119 and lower eyelid 118, conjunctiva tissue 117, and one of the two canthi 120. The view also illustrates the palpebral fissure height ("PFH") clinical measure location 121, which measures the vertical eyelid gap across the cornea.

Table 2 summarizes the variability of eyelid width and under the eyelid depth across many populations and cultures. Table 2 presents the average, the smallest, and the largest general clinical measures for a canthus to canthus palpebral width along the transverse plane, and the under the eyelid measurement: average, minimum, and maximum along the vertical plane of both the upper eyelid UFD and lower eyelid LFD depth to describe the range of anatomical variability of the human population. FIGS. 4A to 4F show example eyeballs, with eyelids, that illustrate data summarized in Table 2.

Figure 4A:
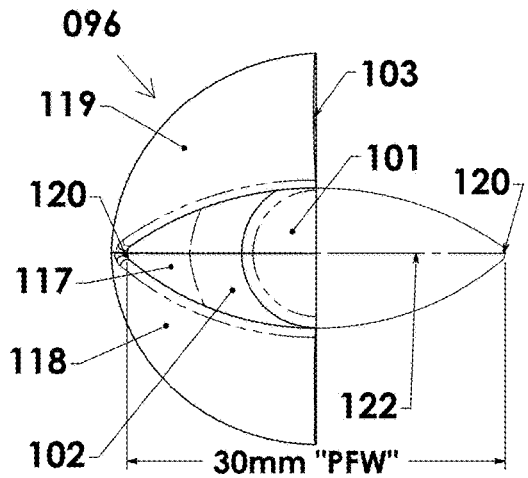
FIG. 4A is a facial view of an emmetropic eyeball of Table 1 with an eyelid representative of a person 20 to 30 years of age, shown as a cross-section in a vertical plane.

FIG. 4A is a facial view of an emmetropic eyeball of Table 1 with an eyelid 096 representative of a person of 20 to 30 years of age, perpendicular to the sagittal plane 103 and the transverse plane 104 and is shown as a cross section in a vertical plane parallel to the median plane (sagittal section). Eyeball 096 has cornea 101, sclera 102, an upper eyelid 119, a lower eyelid 118, the conjunctiva tissue 117, the two canthi (corners) of the palpebral fissure where upper and lower eyelids meet 120, and PFW 122. The example eyeball 096 is shown in FIG. 4A to have a PFW of 30 mm shown as a cross-section in a vertical plane.

Figure 4B:
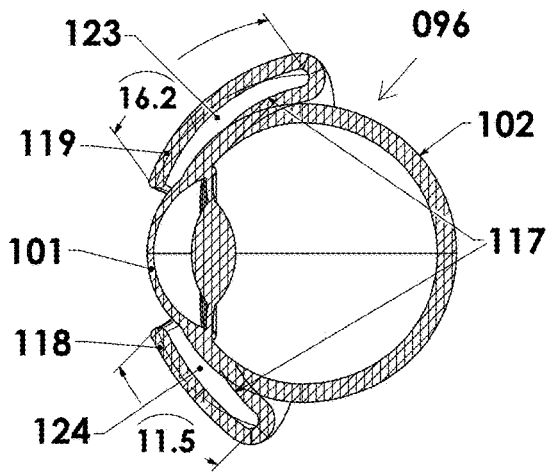
FIG. 4B is a cross-sectional view of the eyeball and eyelid of FIG. 4A showing average upper eyelid depth ("UFD") and average lower eyelid depth ("LFD").

FIG. 4B is a cross-sectional view of eyeball 096 shown in FIG. 4A. FIG. 4B illustrates the upper eyelid (119) fornix depth 123 is 16.2 mm and the lower eyelid (118) fornix depth 124 is 11.5 mm.

Figure 4C:
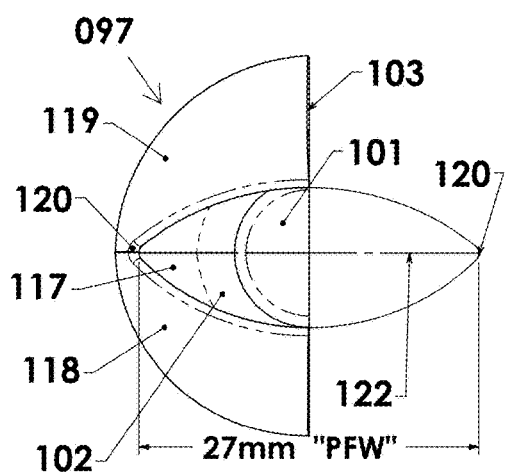
FIG. 4C is a facial view of an eyeball and eyelid representative of a person with palpebral fissure width ("PFW") that is an average canthi width measure of smaller eyes, more likely to be observed in particular populations, shown as a cross-section in a vertical plane.

FIG. 4C is a facial view of an eyeball 097 with smallest observed values for PFW as shown in Table 2, shown as a cross-section in a vertical plane. Example eyeball 097 has a PFW of 27 mm.

Figure 4D:
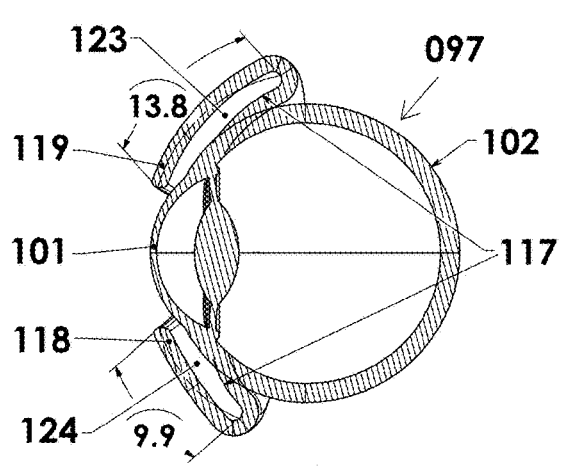
FIG. 4D is a cross-sectional view of the eyeball and eyelid of FIG. 4C showing minimum UFD and LFD.

FIG. 4D is a cross-sectional view of eyeball 097 of FIG. 4C. FIG. 4D illustrates the upper eyelid (119) fornix depth 123 is 13.8 mm and the lower eyelid (118) fornix depth 124 is 9.9 mm.

Figure 4E:
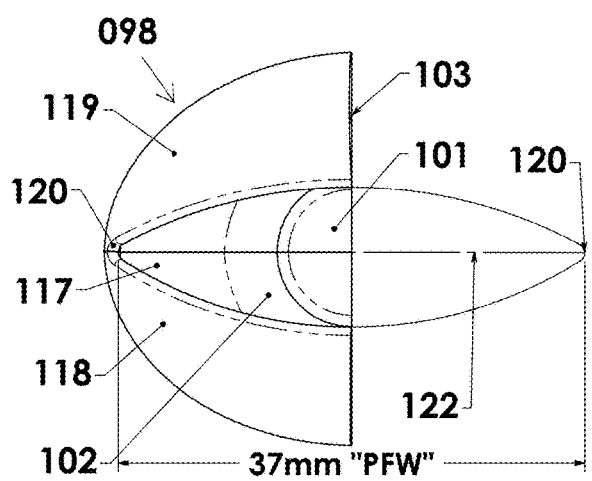
FIG. 4E is a facial view of an eyeball and eyelid representative of a person with PFW that is an average canthi width measure of larger eyes, more likely to be observed in particular populations, shown in cross-section in a vertical plane.

FIG. 4E is a facial view of an eyeball 098 representative of an eyeball with the maximum observed PFW 122 of 37 mm, maximum upper eyelid depth (mean) ("UFD"), and maximum lower eyelid depth (mean) ("LFD") provided in Table 2.

Figure 4F:
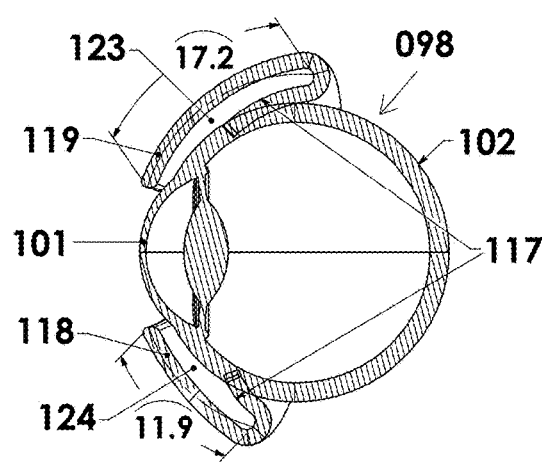
FIG. 4F is a cross-sectional view of the eyeball and eyelid of FIG. 4E showing maximum UFD and LFD.

FIG. 4F is a cross-sectional view of the eyeball and eyelid of FIG. 4E.

TABLE 2

|  | ID# |  | ID# | "PFW" | ID# | "UFD" | ID# | "LFD" |
|---|---|---|---|---|---|---|---|---|
| FIGS. 4A and 4B | 096 | Average Values | 122 | 30 mm | 123 | 16.2 mm | 124 | 11.5 mm |
| FIGS. 4C and 4D | 097 | Smallest Values | 122 | 27 mm | 123 | 13.8 mm | 124 | 9.9 mm |
| FIGS. 4E and 4F | 098 | Largest Values | 122 | 37 mm | 123 | 17.2 mm | 124 | 11.9 mm |
|  |  | Range of the Figures (mean) by Feature |  | 10 mm |  | 3.4 mm |  | 2.0 mm |
|  |  | Max Range of the Raw Data by Feature |  | 27-37 mm |  | 8.2-24.3 mm |  | 5.9-16.0 mm |

"PFW" = Palpebral Fissure Width (mean)
"UFD" = Upper eyelid depth (mean)
"LFD" = Lower eyelid depth (mean)

Clinical Detail and Illustration of the Kinematics and Observed Forces of the Eye, and the Eyelid.

Researchers studying kinematics of eye anatomy have described significant rapid and frequent motion of the eyeball and the eyelids in the human population. The following description, summary tables, and accompanying figures illustrate clinical observations, measurements, and ocular forces as background to assist in understanding the description that follows. Clinical observations include measurements of saccade eye motion, saccade eye motion during fixation, eye blink, and eyelid tension.

Saccade

Saccade eye motion is rapid, has a nominal constant strength value and is millisecond length in duration, which is a function of angular displacement. Vision requires continuous motion of the ocular anatomy for retina cell stimulation. Thus, an eyeball is typically not completely motionless.

The extent to which the surface of an eyeball (sclera) of known radius (half the diameter) moves, known as surface translation, can be calculated from the angle that the eye moves. The formula for determining surface translation is the radius of the eye (r) times the angle of movement in degrees θ times pi (π) divided by 180 or (r×θ×π)÷180. As an example, an eyeball with a diameter of 24 mm would have a radius of 12 mm. If the eyeball moves 5 degrees, the surface translation would be (12 mm×5×3.14)/180 or 1.05 mm.

Table 3 below summarizes scleral surface translation based on clinical saccade eye motion studies of an eyeball with a diameter of 24 mm (radius of 12 mm) for the following:

Gross (macro) angular eye motion in the field of view; and
Fixation saccade (micro angular eye motion) across image types.

See Robinson D A; (1964) "The Mechanics of Human Saccadic Eye Movement" J. Physiol [1964] 174 PP 245-264, and Castelhano, M; & Henderson, J (2008) "Stable Individual Differences Across Images in Human Saccadic Eye Movements" Canadian Journal of Experimental Psychology: 2008 Vol. 62 No. 1 PP 1-14.

The study summarized in Table 3 considered macro non-fixated saccade angular displacements, in the range of 5° to 40° for an eyeball with cross-section of nominal thickness with a 12 mm outer surface radius 102 with external surface curvature length displacement amount as defined by angular saccade values of 5°, 10°, 15°, 20°, 25°, 30°, 35°, and 40°. Surface displacement calculated values are provided, representing expected surface displacement for each macro saccade angle.

Table 3 further summarizes results of a study of the gaze fixation micro saccade angular displacements an eyeball with cross-section of nominal thickness with a 12 mm outer surface radius at angular saccade values of 1.4°, 2.5°, and 3.3°. Calculated sclera surface translations appear in Table 3 for each fixation type.

The Table 3 summary of continuous saccade motion and time is relevant to a device to be placed under an eyelid or within a "conjunctival sac" and thus affected by this dynamic rapid motion environment.

TABLE 3

| | | Saccade magnitude (deg.) | | | | | | | |
|---|---|---|---|---|---|---|---|---|---|
| | | 5° | 10° | 15° | 20° | 25° | 30° | 35° | 40° |
| Excess force | Strength (g) | 25 | 24-6 | 26 | 25-2 | 25-2 | 23 | 23 | 22 |
| | Duration (msec.) | 29 | 40 | 55 | 65 | 74 | 87 | 95 | 100 |
| | Sclera Surface Translation (mm) | 1.05 | 2.09 | 3.14 | 4.19 | 5.24 | 6.28 | 7.33 | 8.38 |

| | "Fixation" Visual Saccade (deg.) | | |
|---|---|---|---|
| | 1.4° | 2.5° | 3.3° |
| Time between saccades (msec.) | 209 | 329 | 337 |
| Sclera Surface Translation (mm) | 0.29 | 0.52 | 0.69 |

Eye Blink

An eye blink is movement of the eyelids to wipe the surfaces of the eye. The blink action closes the Palpebral Fissure height ("PFH") in a range of 25% to 100% in about 0.1 seconds, an extended blink closure minimal of ½ second. Eyelid movement, a surface translation of the inner eyelid in relation to the eyeball anatomy, is generally along the vertical eye meridian. Eyelids generally move in a range of 25% to 100% ("PFH"=0 at 100%).

Information about blink rates and the blink actions is summarized in Table 4.

TABLE 4

| Duration of Eye-Blink (seconds) 0.1(80%-95%)/0.5(5%-15%) | | | |
|---|---|---|---|
| | Average #/Minute | Men | Women |
| Rest | 17 (4-48, 6-40) | 15.6 | 18 |
| Reading | 4.5 (0.7-22, 1-16) | 3.0 (0-13, 0-10) | 6.2 (0-26, 0-20) |
| Conversation | 26 (11-53, 13-47) | 24 | 26.7 |

| | Average #/Minute | |
|---|---|---|
| Rest | 8-21 | |
| Reading/Focus | 4.5 | |
| Conversation | 10.5-32.5/19-26 | |

| | Normal Eye | "Dry-Eye" |
|---|---|---|
| Blink #/Minute Events (0.1/0.2 sec duration) | 13 | 28.55 |
| # Blinks (>0.2 sec duration) | 6.11 | 14.12 |

Eyelid Tension

Eyelid force(s), important for the retention of a device intended to be placed under an eyelid, have been measured in posteroanterior (PA), nasal, and temporal directions. These forces represent lower eyelid anatomy performance for device retention capability. Relevant factors are summarized in Table 5 and Table 6.

TABLE 5

Mean Postero-anterior (PA) Eyelid Tension by age and gender

|  | Younger n = 12<br>29 ± 5 years of age | Older n = 20<br>74 ± 6 years of age | All<br>n = 32 |
|---|---|---|---|
| Males n = 16 | 14.8 ± 5.1 mN/mm | 12.2 ± 4.0 mN/mm | 13.2 ± 4.8 mN/mm |
| Females n = 16 | 10.7 ± 1.8 mN/mm | 10.0 ± 2.4 mN/mm | 10.3 ± 2.3 mN/mm |
| All Subjects | 12.8 ± 4.2 mN/mm | 11.1 ± 3.5 mN/mm | 11.8 ± 4.0 mN/mm |

TABLE 6

Comparative Eyelid Tension by Location for the "Younger" age group population

| Group Age<br>n = 12 | Nasal | Postero-<br>anterior (PA) | Temporal |
|---|---|---|---|
| 29 ± 5 years of age | 13.0 ± 4.6 mN/mm | 11.2 ± 5.3 mN/mm | 7.8 ± 2.9 mN/mm |

Described is a system of interactive elements that work cooperatively to provide to the user an adaptive ocular device that remains stable and comfortable when placed under an eyelid. The unique challenges in this area of ocular anatomy and the degree of anatomical variability, motions, and forces provide a particular environment for ocular devices for this purpose.

The description illustrates aspects of an ocular device, including its adaptive characteristics. Features of an ocular device may be presented isolated from the device for additional clarity. Features can be incorporated with each other into an ocular device.

Described is a system that includes an ocular device that adapts to variations of ocular anatomy, is comfortable within the ocular space, locates and remains stable within the ocular anatomy, resists forces from eyeball and eyelid motion, and retains tear fluid.

Devices are described for the upper and lower eyelid. The devices have adaptive characteristics. The descriptions of the devices are not intended to be restrictive or limiting in any way. In particular, there can be alternative anatomical placement locations for any of the devices described.

Materials for Ocular Devices.

It is advantageous that the composition and properties of an ocular device enable translation along multiple degrees of freedom.

Materials are advantageous that facilitate transition from a planar "as manufactured" configuration, or from an intermediate partially transitioned manufactured configuration shape, into a device that is patient compatible when placed within the ocular anatomy to perform its purpose.

Ocular devices may be made from a material that provides a device that is configured to be adaptive. Anatomy compatible virgin and composite combinations of materials can be used to make ocular devices, including injection moldable materials.

Materials that can be used in making an ocular device with adaptive characteristics can include but is not limited to the following, alone or in combination or as a composite: metal, polymer, composite, thermoplastic polymers, thermoset polymers, thermoplastic elastomers, thermoset elastomers, metallic compositions, or pure elements, such as carbon nanotubes, or combinations thereof.

Suitable material can but need not be hydrophilic. A hydrophilic property material for any under the eyelid or on the cornea or on the sclera devices is well defined and characterized by contact lens material practice and many ocular clinical publications.

A suitable, low-cost injection moldable material, which has a proven history of use in anatomical contact medication delivery systems that provides superior patient comfort residing in the ocular space, is the class of ethyl-vinyl acetate (EVA) thermoplastic copolymers. These materials, with ocular anatomy compatible, hydrophilic properties provide the appropriate hardness, flexural modulus for translation during adaptation and critical tear wetting properties for compatibility and comfort within the ocular anatomy.

Surface Finish for Ocular Devices.

The surface finish of an optical device can include injection molding technology surfaces with optical quality finishing.

Compositions, materials, and methods known in the art can be used. The compositions, material, and methods can be selected to increase patient comfort and device retention and minimize user sensation.

Manufacturing Methods.

Manufacture and validation of an ocular device and transport mechanism require process steps that include process loss that impacts cost. A manufacturing process is described in U.S. Pat. No. 9,937,073 (de Juan et al), the entire teachings of which are incorporated here by reference in their entirety.

There are many manufacturing methods that may be used to generate the device. One example that may be used is to select an injection molding material that meets material performance attributes and utilize an injection molding process to create the device, then apply a mechanical assembly method to place medication delivery inserts within the ocular device.

Ocular devices are not limited to devices made by any particular method. Manufacture Process steps can follow the flowchart in FIG. 8A as an example:

Injection mold the ocular device;
Generate the medication insert(s) to fit the ocular device pocket(s);
Optionally add medication or another substance; and
Assemble the insert(s) with the ocular device, creating a clinical use device.

Figure 8A:
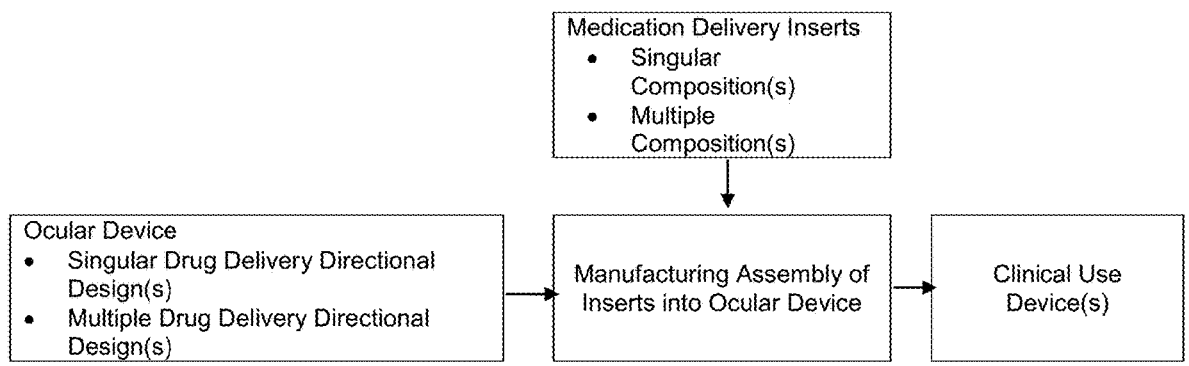
FIG. 8A is a flowchart illustrating an example of a manufacturing process for clinical use device(s) according to an example embodiment.
Figure 8B:
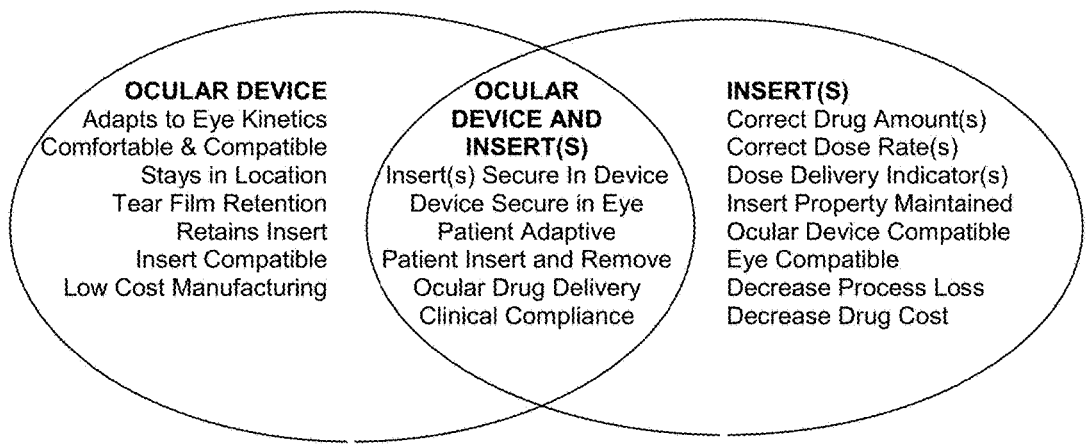
FIG. 8B is a diagram illustrating performance attribute contributions of ocular device(s) and insert(s).

This example is a simple process that is scalable and low cost, providing manufacture process steps that generally follow the FIG. 8A and providing the Performance Attributes of Ocular Devices and Insert(s) shown in FIG. 8B.

An ocular device can be formed, in whole or in part, of pharmaceutically active agent blended with other material enabling delivery of pharmaceutically active agent from the ocular device. As an example, an ocular device can be a plate, or can include a plate, that is formed, in whole or in part, of material that includes a pharmaceutically active agent.

Ocular Devices Provided as Structural Examples.

Ocular devices for placement under an eyelid are described and depicted in figures that illustrate features that can be included in an ocular device. Descriptions and figures include multiple features connected together, for example, one or more plates connected to an elongated support member. Features are shown connected for illustrative purposes and not as a limitation. An ocular device for placement under an eyelid can be a plate that is not connected to other features. It should therefore be understood that each of the plates illustrated herein could serve as an ocular device, without any other feature attached to the plate. Alternatively, one or more plates can be connected to a support member or an elongated support member. The connection of one or more plates to a support member or an elongated support member is not limited to any of the configurations described or shown in a particular figure.

Normal eye tear fluid volume is considered to be about 7.2 μl. Each eye can have tear fluid volume that is greater or less than normal. It should be understood that an ocular device shown in a figure or described herein, when placed under an eyelid, provides open space 250. An eye with an ocular device placed under an eyelid generally has greater tear fluid volume than the eye would have without the ocular device.

Increased tear fluid volume can facilitate enhanced residence time for absorption of a drug into ocular anatomy tissues. Drugs will experience longer ocular tissue contact residence times as compared to eye drop ocular medication delivery systems. Low solubility barriers of many medications can be overcome by the increased delivery of the drug in concert with increased tear residence time.

Figure 5A:
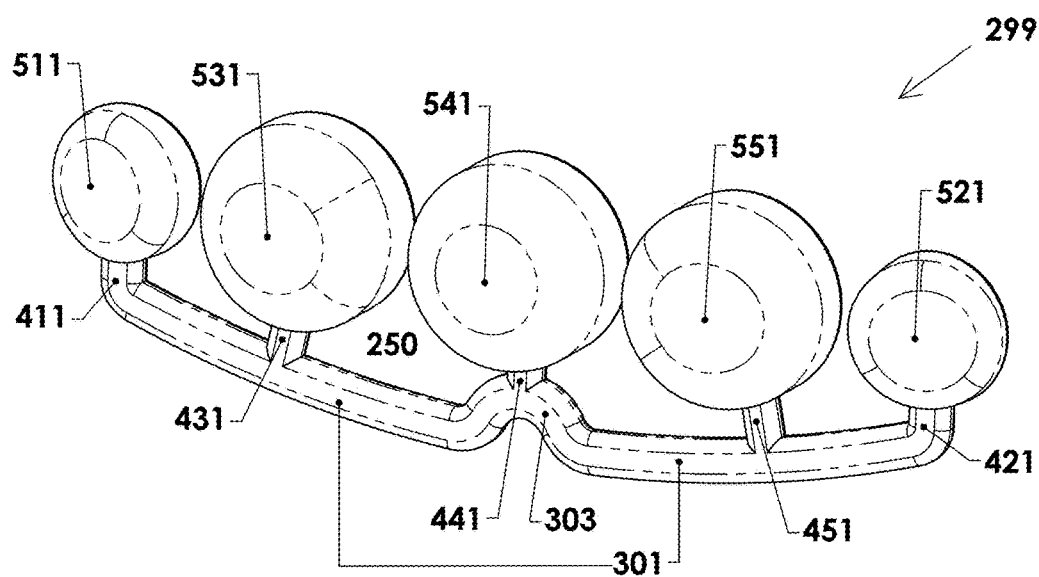
FIG. 5A is an isometric view of an example of an ocular device.
Figure 5B:
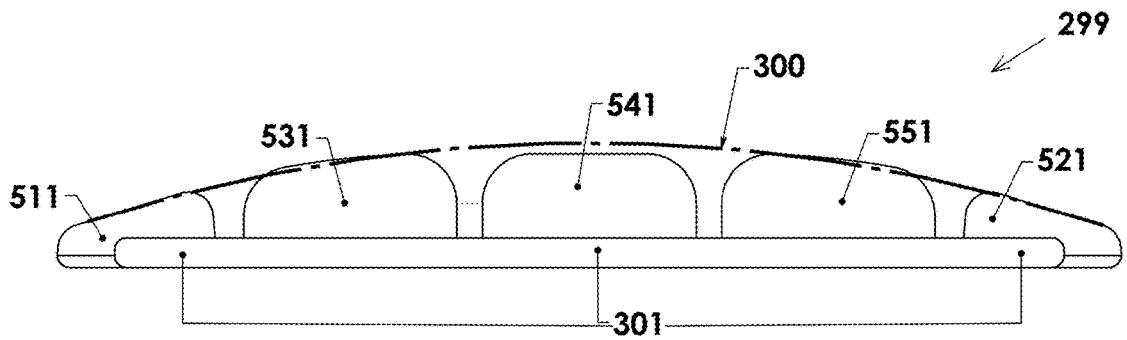
FIG. 5B is a bottom view of the ocular device of FIG. 5A.
Figure 5C:
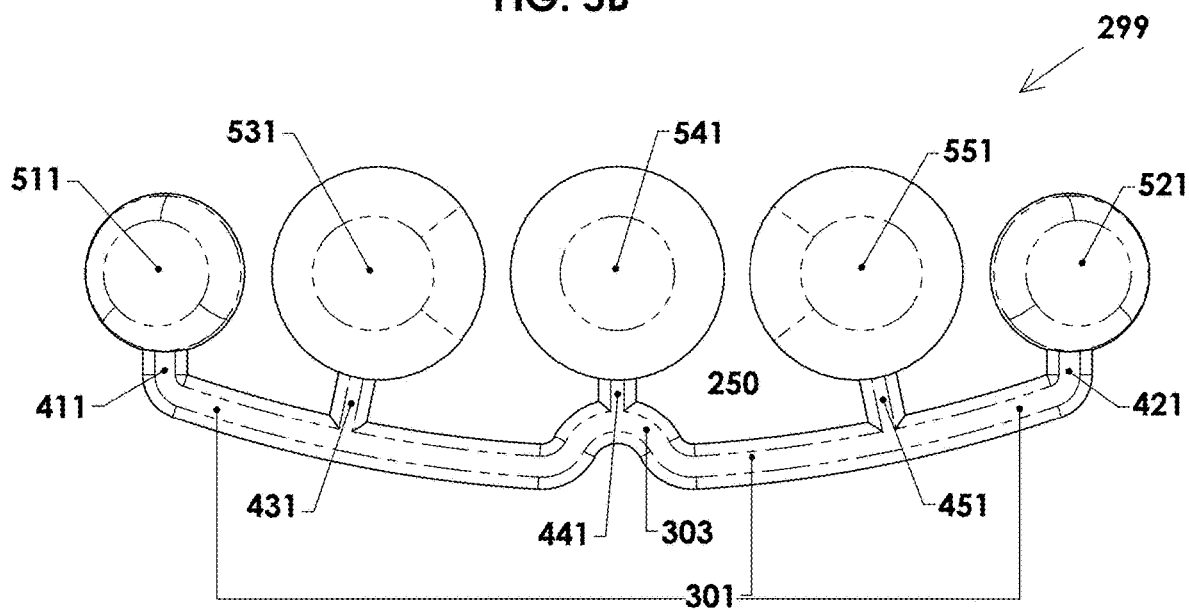
FIG. 5C is a front view of the ocular device of FIG. 5A.

FIGS. 5A, 5B, and 5C are isometric, bottom, and front views, respectively, of an example of an adaptive ocular device 299 for the eye. The ocular device 299 includes an elongated support member 301, plates 511 and 521 connected proximate to each end of the support member and substantially coplanar with the support member, and plates 531, 541, and 551 connected to the support member between plates 511 and 521. An ocular device can be placed under an eyelid in various positions and orientations. As an example, without limitation, an ocular device can be placed under an eyelid with the elongated support member toward the fornix. As another example, without limitation, an ocular device can be placed under an eyelid with the plates toward the fornix. Once placed under the eyelid, an ocular device can position itself and can rotate about its horizontal axis. Plates 511 and 521 are configured to be positioned adjacent to the canthi of the eye. The plates are configured to adapt to the ocular anatomy. Plates 531, 541, and 551 are substantially coplanar with the support member and plates 511 and 521. A plate has a back surface that can have at least one protrusion having a convex contact surface. The ocular device can include a substance to be delivered to the eye, such as medication. The elongated support member 301, when in an eye, extends toward each canthus of the eye. Elongated support member 301 can be made of flexible material. The elongated support member 301 can include an arch 303. The ocular device can have an elongated support member with a variable cross-section along its length (see FIG. 19A).

Adaptability of each plate of ocular device 299, alone or in concert, provides an adaptive device that adjusts to variation in ocular anatomy, which is advantageous.

FIG. 5A shows, with example ocular device 299, the presence of open space 250 around ocular device 299. Open space 250 allows multiple degrees of freedom of movement of each plate and other features of ocular device 299 relative to each other. Ocular device 299 in an eye generates a larger tear volume than the eye without the ocular device. Open space 250 and the offset space between the sclera and the back surface of the plate assist in achieving the larger tear fluid volume resulting from the insertion of the ocular device in the eye. The elongated support member 301 can itself be formed from flexible material, providing its own degrees of freedom, further providing an adaptive ocular device.

When in the eye, plates 511 and 521 can stabilize the ocular device.

In FIGS. 5A and 5C, ocular device 299 includes flexible connectors 411, 431, 441, 451, and 421, which connect the plates to the support member.

FIG. 5B shows an ocular device with a plane curve surface 300 to show the projected feature shape or height of the plates in the example ocular device 299. Plane curve surface 300 appears in FIG. 5B merely for illustrative purposes.

Eyelids have both a diminishing volume capacity and a diminishing fornix to the palpebral eyelid depth as the eyelid approaches the canthi 120 junctions, located at the nasal and temporal position, see FIGS. 3A and 3B. To achieve a comfortable design fit and device retention, it is advantageous that plates 511, 521 be placed closer to the canthi, connected to an elongated support member 301 that is compatible with the fornix, and that the plates be adapted in shape, size, and contour to reside within the eyelid volume and depth.

In FIG. 5B, in an example ocular device 299, illustrative plane curve surface 300 is best described as follows: beginning with plate 511, the plates generally follow plane curve surface 300, as shown, starting at the left of FIG. 5B at plate 511, increasing in height across plate 531, to a peak at plate 541, shown central in this device 299, then decreasing in height across plate 551 and returning to a reduced height along plate 521, shown to the right in FIG. 5B.

The radius of curvature of 300 may be adjusted to be steeper (smaller radius) or flatter (larger radius) than has been illustrated in FIG. 5B, providing more or less volume to plates 531, 541, and 551, and changing the overall device height along the path of curve 300. The plate volume and overall device height determines the offset location of the eyelid in relation to the sclera, on insertion, where the eyelid is the most remote surface from the sclera.

Device 299, with plates, flexible connectors, and an elongated support member made of flexible material provides an ocular device that can be inserted under an eyelid and adjust and adapt individually or in concert to the variations of ocular anatomy and ocular structures.

The shape and height of the curve of 300 for an ocular device can be adjusted to allow for a user's eyelid tension and the shape of a user's eyelid. Such adjustments can provide an ocular device with an appearance when inserted under an eyelid that is cosmetically acceptable in order to achieve successful adoption of the ocular device.

Figure 18A:
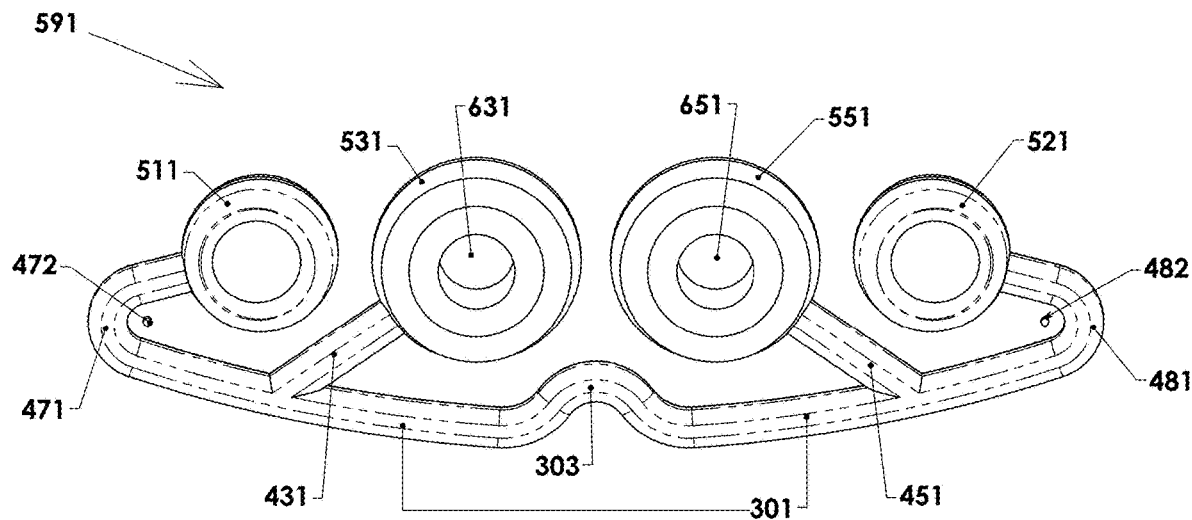
FIG. 18A is a front view of an ocular device.
Figure 18B:
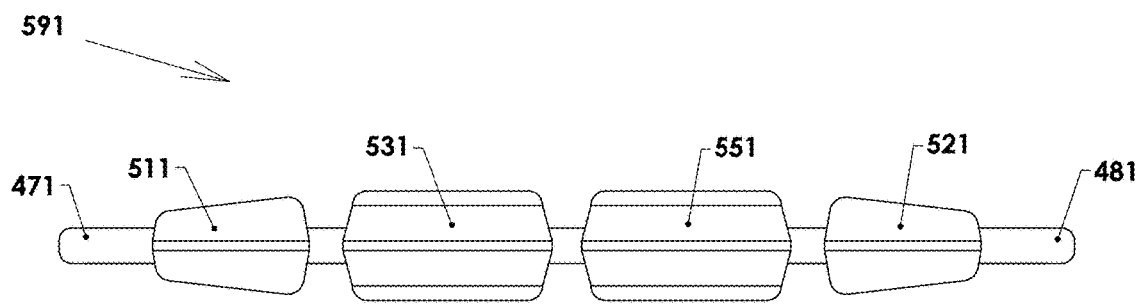
FIG. 18B is a top view of the ocular device of FIG. 18A.
Figure 18C:
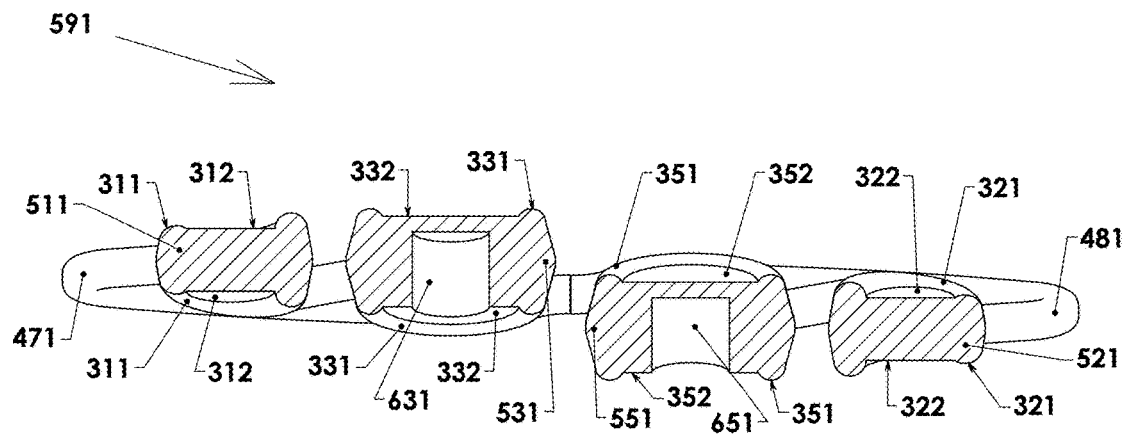
FIG. 18C is a top view of the ocular device of FIG. 18A with the top portion of the plates cut away.

The plates in an ocular device such as the device exemplified in FIGS. 5A to 5C can include a front surface, on the other side of the plate from the back surface, and the front surface can, optionally, have at least one protrusion having a convex contact surface to contact the sclera of an eye and to provide an offset space between the sclera and the front surface of the plate, so that the ocular device can be inserted with the front surface toward the sclera (see, e.g., device 591 illustrated in FIGS. 18A-18C). The ocular device can be placed in the eye with the back or the front surface of the device toward the sclera.

Figure 5D:
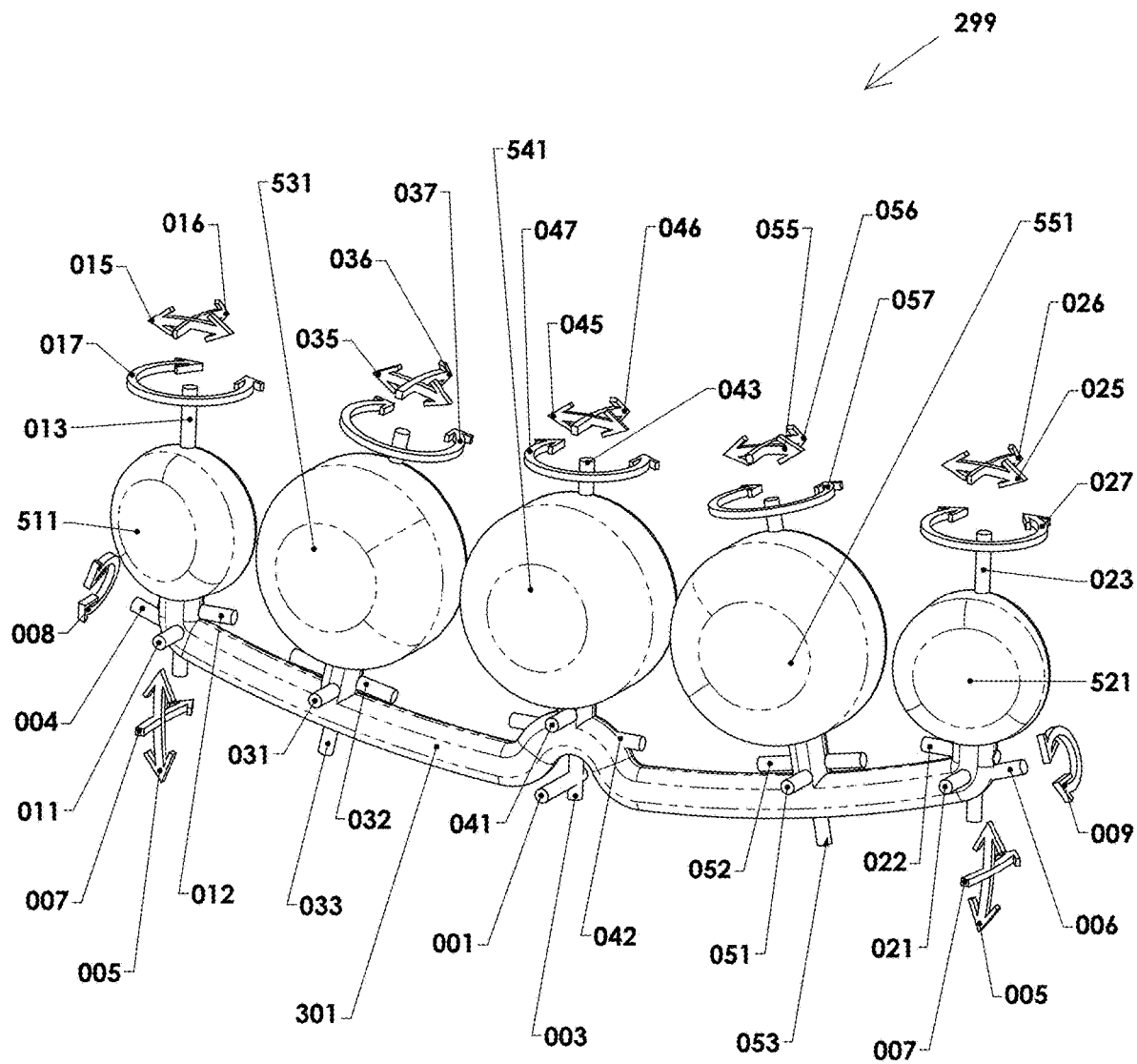
FIG. 5D is an isometric view of the ocular device of FIG. 5A, showing multiple degrees of freedom of adaptability of the ocular device of FIG. 5A.

FIG. 5D is an isometric view of the ocular device of FIG. 5A. To illustrate adaptive capabilities of the example ocular device in FIGS. 5A to 5C, FIG. 5D shows ocular device 299 with the addition of rotational axes that are not actually present in the device but are shown in FIG. 5D for illustrative purposes. FIG. 5D provides arrows to illustrate multiple degrees of freedom, illustrating adaptability of ocular device 299. In FIG. 5D, rotational degrees of freedom of the plates is illustrated by rotational directional "arrows" associated with the inserted axis of rotation added for each of the plates.

Degrees of freedom of the elongated support member are also identified in the example.

The ocular device disclosed is further described by referring to FIGS. 6A-6G, which show examples of elongated support members 301 that can be in an adaptive ocular device and examples of ocular devices. Exemplary elongated support members 301 can have different configurations.

Figure 6A:
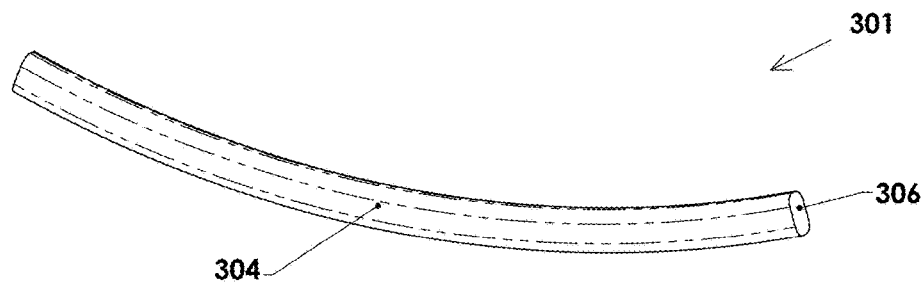
FIG. 6A is an isometric view of an example of an elongated support member for an ocular device.

FIG. 6A illustrates elongated support member 301 without an arch.

Figure 6B:
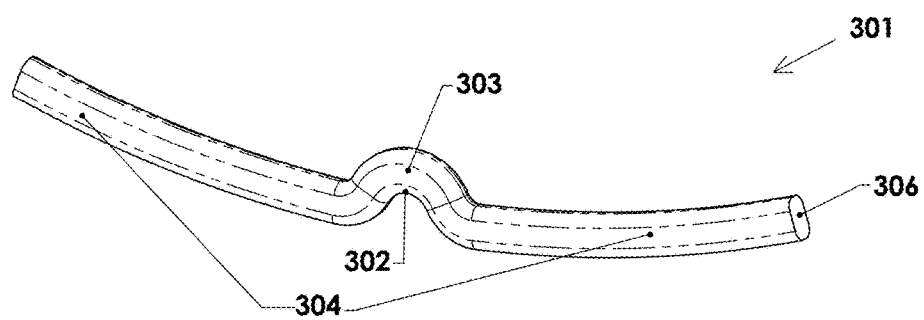
FIG. 6B is an isometric view of an example of an elongated support member for an ocular device.

As illustrated in FIG. 6B, elongated support member 301 can have a rectangular cross-section 306. The cross-section of elongated support member 301 can vary along the length of the elongated support member (see, e.g., device 800 illustrated in FIGS. 19A-19C). The cross-section can be rounded so that it provides an atraumatic surface, with an approximate thickness of about 0.2 mm to about 1.5 mm and a height about 0.45 mm to 2.25 mm. Member 301 can follow a sweep curve 304 across the width of the device, and can include an arch 303, which can be located in the general area of the midpoint of member 301. The arch 303 can be centrally placed within the structure 301.

In FIG. 6B, the peak of arch 303 is at about double the vertical cross-section 306, and at about the device midpoint. The arch 303 can represent approximately 15% of the overall horizontal width of member 301.

As shown, for example, by FIG. 6A and FIG. 6B, the elongated support member of an ocular device can be made with or without an arch 303. When an arch is present, the underside 302 of the arch 303 can include an attachment to assist with manufacturing. Placing an attachment or manufacturing aid on the underside 302 of the arch 303 so that it is away from and not interfering with placement of the ocular device under an eyelid can minimize negative clinical impact on performance of the ocular device.

A manufacturing aid can be a gate for injection molding or injection casting or solution casting with and by singular or multi-staged methods and materials including but not be limited to: thermoplastic polymers, thermoset polymers, in situ polymerizations, drug-polymer composite constructs, and coatings. A manufacturing aid can also be a handling attachment tab for manufacturing processing and/or high-speed automation. In addition, a manufacturing aid can also be a location feature for subsequent element creation processing, lamination, composite assembly, coating, medication insertion, and/or medication infusion by multiple process step methods. A manufacturing aid can also be a patient or physician removable identification marker, with or without an embedded electronic scannable identification tag component or a medical device regulatory sanctioned scannable device barcode identifier.

Figure 6C:
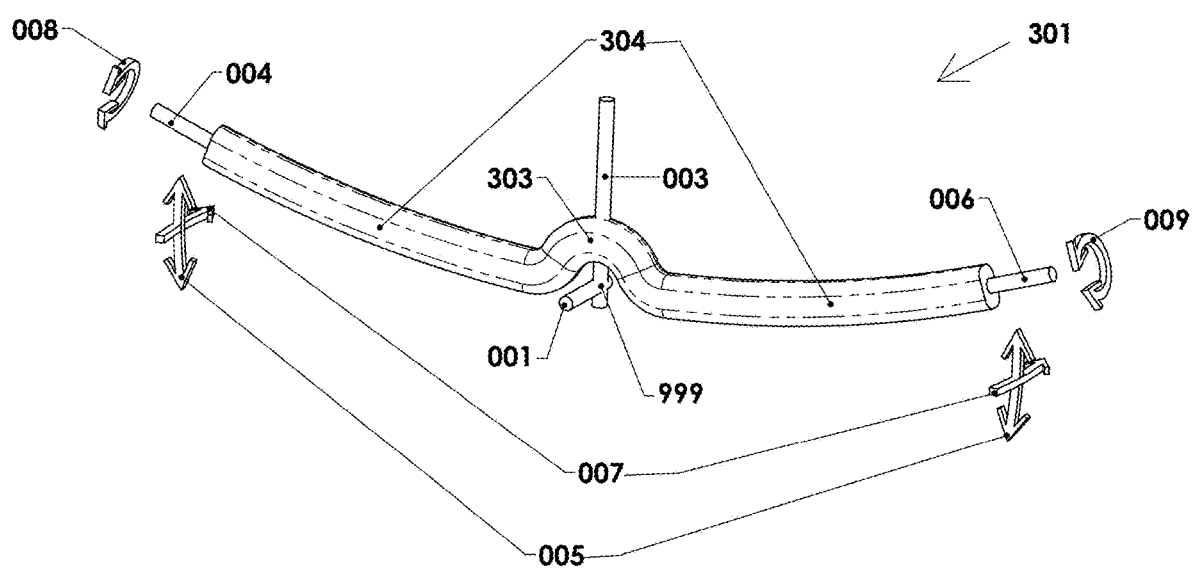
FIG. 6C is an isometric view of the elongated support member of FIG. 6B, including vertical, horizontal, and twisting axes and associated arrows that show rotational degrees of freedom. The axes are provided for reference and are not part of the device.

FIG. 6C illustrates rotational capabilities of an example elongated support member 301 that contribute to the ocular device being adaptive. A horizontal (perpendicular projecting) axis 001 and a vertical (perpendicular to the horizontal plane) axis 003 define a local origin point 999 of elongated support member 301. The arch 303 provides a rotational feature about which each sweeping arc 304 has a twisting capability as is defined by an axis 004 and twist directional arrow 008 on one end and an axis 006 and twist directional arrow 009 at the other end.

Figure 6D:
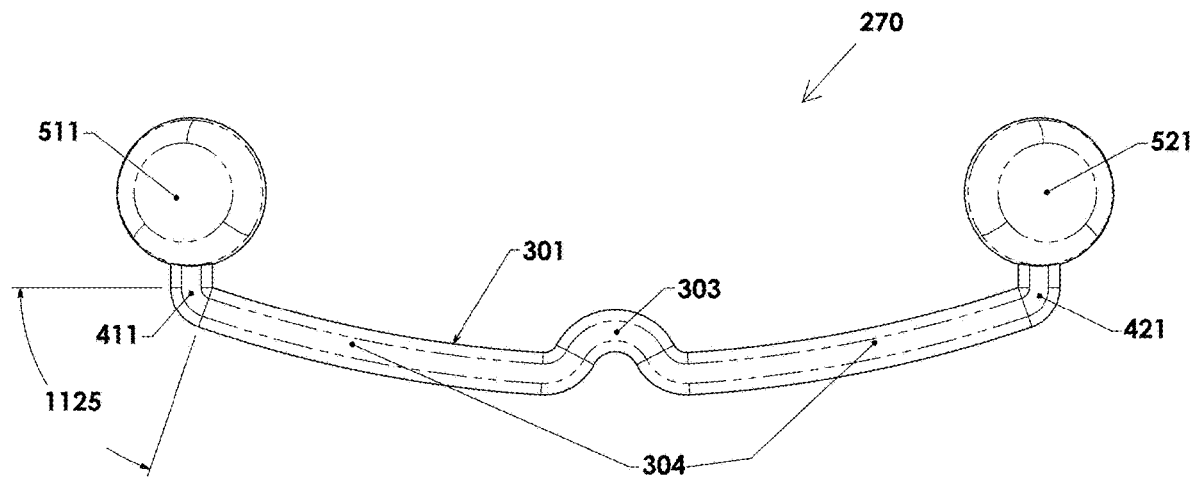
FIG. 6D is a front view of an elongated support member with plates connected to the elongated support member, showing flexible connectors.

FIG. 6D illustrates ocular device 270 with plates 511, 521 connected proximate to each end of the elongated support member, each of plates 511, 521 is configured to be positioned adjacent to a canthus of an eye. Plates 511, 521 of the ocular device 270 are capable of adapting to ocular anatomy. Ocular device 270 is an example of a device that does not include plates other than the plates that are connected proximate to each end of the elongated support member 301.

Elongated support member 301 appears in FIG. 6D with arch 303 and sweeping arcs 304. Flexible connector 411 is connected to the elongated support member at an acute angle 1125 and connects plate 511 to the elongated support member, and similarly on the other end of the elongated support member flexible connector 421 is at an acute angle to the elongated support member, connecting plate 521 to the elongated support member.

In general, a flexible connector can form an angle with the elongated support member that is a range of less than 90 degrees to more than 180 degrees, connecting the elongated support member to the plate, with the elongated support member and a surface of the plate being substantially coplanar.

Figure 6E:
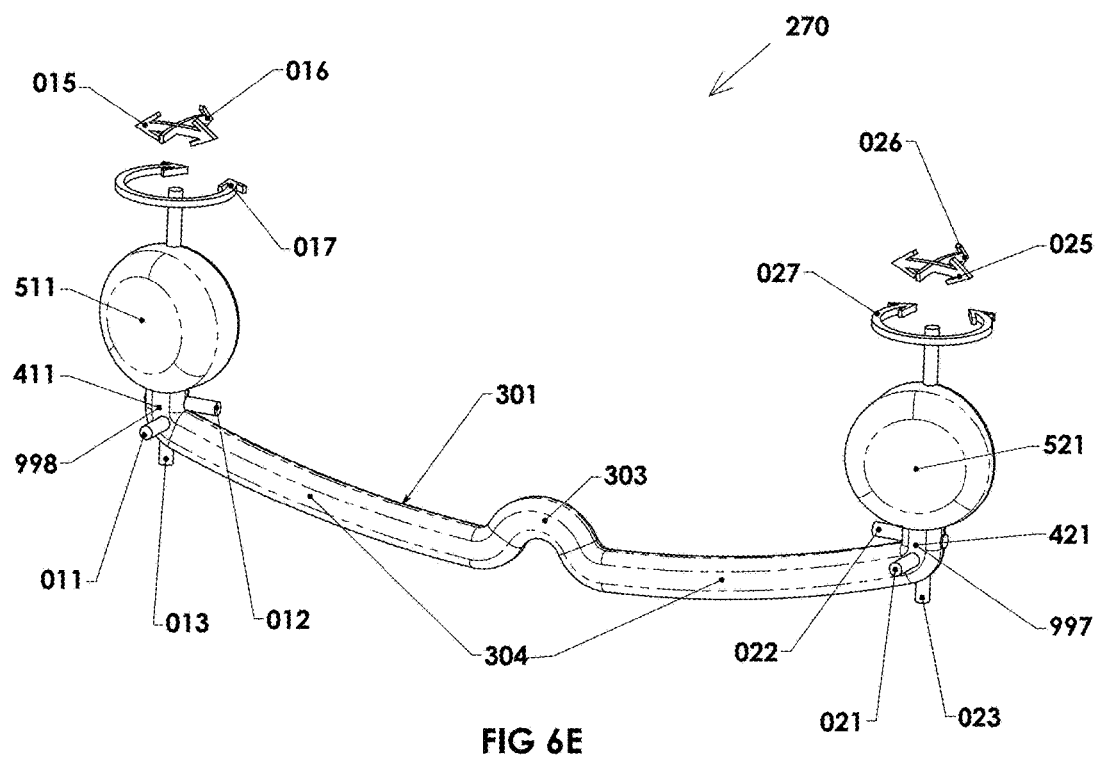
FIG. 6E is an isometric view of the device of FIG. 6D, including vertical, horizontal, and twisting axes and associated arrows that show rotational degrees of freedom. The axes are provided for reference and are not part of the device.

FIG. 6E illustrates an isometric front view of ocular device 270 shown in FIG. 6D, with plates 511, 521 and flexible connectors 411, 421 attached to the elongated support member 301. Vertical, facial and twisting axes, which are not part of the device and provided for illustration, and associated rotation arrows show degrees of freedom of motion of the plates in relation to the elongated support member that enable adaptation to ocular anatomy.

In FIG. 6E, the rotational capabilities of plates 511, 521 and connecting elements 411, 421 are shown relative to the elongated support member 301. Point 998 on flexible connector 411 (left illustrated element) provides a point of reference for adaptive motion of connector 411 and plate 511 at the intersection axis 011, horizontal axis 012, and vertical "twist" axis 013. Directional arrow 015 indicates motion about axis 011, arrow 016 about axis 012, and arrow 017 about axis 013 for plate 511 and flexible connector 411 relative to the location and position of sweeping arc 304. Point 997 on flexible connector 421 (right illustrated element) provides a point of reference for adaptive motions of connector 421 and plate 521 at the intersection axis 021, horizontal axis 022, and vertical "twist" axis 023. Directional arrow 025 indicates motion about axis 021, arrow 026 about axis 022, and arrow 027 about axis 023 for plate 521 and connector 421 relative to the location and position of sweeping arc 304.

Figure 6F:
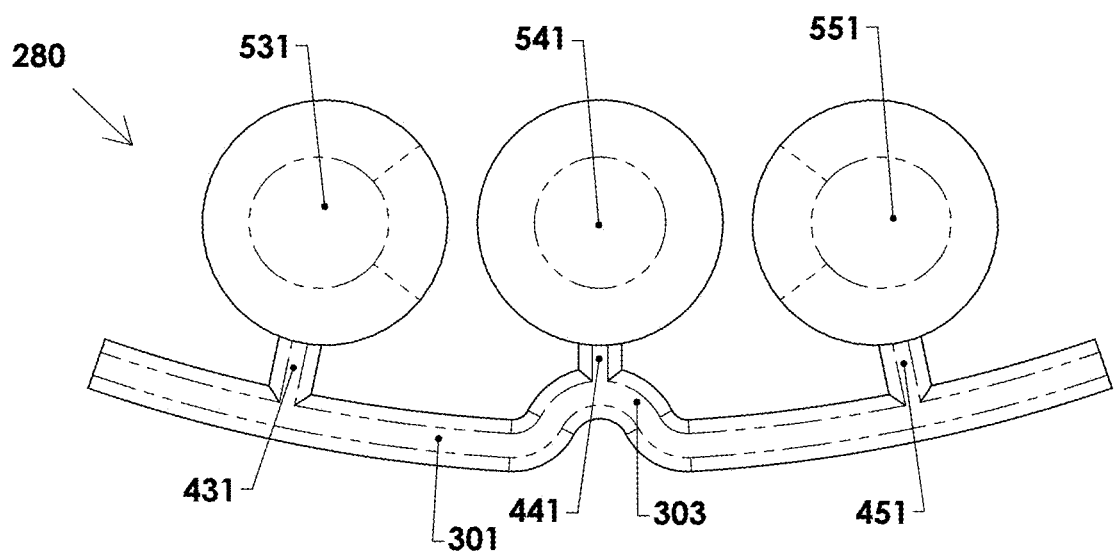
FIG. 6F is a front view of an elongated support member with plates connected to the elongated support member, showing flexible connectors.

FIG. 6F illustrates an ocular device 280 with plates 531, 541, 551 that can adapt to ocular anatomy and that are linked to the elongated support member 301 by flexible connectors 431, 441, 451. It can be noted that plates 531 and 551 are connected further from the ends of the elongated support member than plates 511 and 521 in FIG. 6E.

In FIG. 6F, elongated support member 301 is shown with the arch and sweeping arc and the flexible connectors 431, 441, 451 projecting perpendicular to the elongated support member curvature to engage the plates 531, 541, 551, respectively. Connector 441 and plate 541 in the ocular device 280 are located centrally and attached to the top of the arch of elongated support member 301. Connector 441 and plate 551 may alternatively be located in a non-central position and, as shown in FIG. 6A, the arch may not be present. It should be appreciated that features shown in any figure, such as perpendicular projection of a connector, are merely illustrative of an example.

Figure 6G:
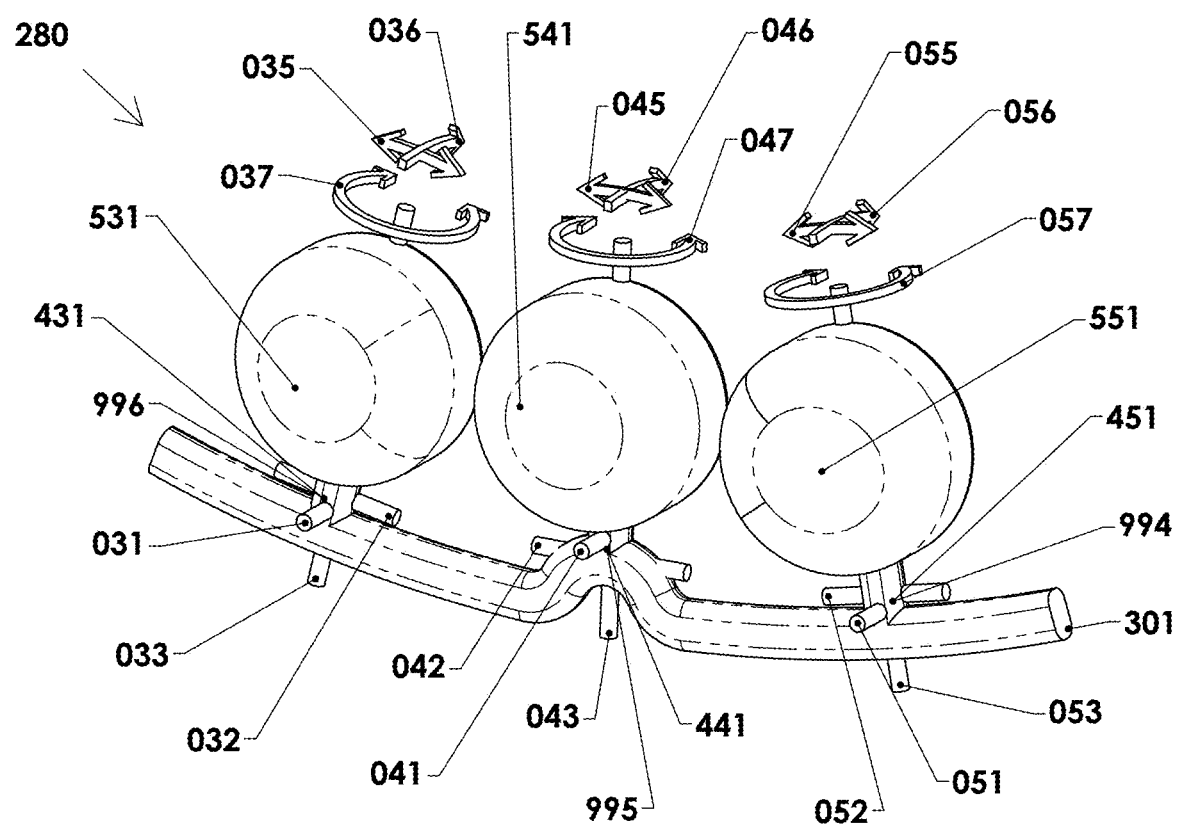
FIG. 6G is an isometric view of FIG. 6F, including vertical, horizontal, and twisting axes and associated arrows that show rotational degrees of freedom. The axes are provided for reference and are not part of the device.

FIG. 6G is an isometric front view illustrating plates 531, 541, 551 and connectors 431, 441, 451 attached to the elongated support member 301 of ocular device 280. Vertical, facial, and twisting axes and associated rotation arrows define degrees of freedom motion of the plates relative to the elongated support member in a device 280 that is adaptive to ocular anatomy.

FIG. 6G provides further illustration of rotational capabilities of the plates 531, 541, 551 and flexible connectors 431, 441, 451 relative to elongated support member 301.

Ocular Device Placed within Eye Anatomy.

An adaptive ocular device with multiple degrees of freedom capability will be further described by illustrating an ocular device in an eye. The descriptions and associated figures are not meant to be limiting. For example, while an example of an ocular device may be shown located under the lower eyelid of an emmetropic eye, the same ocular device could instead be shown under the upper eyelid of the emmetropic eye or under the upper or lower eyelid of an eye with myopia or hypermetropia. As a further example, an example of an ocular device may be shown in an orientation, the ocular device could be in a different orientation in the eye. Similarly, and as a further example, an ocular device may be shown in a location under an eyelid, but the location under the eyelid where it is shown is not a limitation on where under an eyelid an ocular device can be placed or to which it can move.

When placed into an ocular space, the disclosed optical device self-adjusts to adapt and fit to the anatomy of the eye. The disclosed ocular device can continue to adjust and self-correct to conform to possible changing variations of non-corneal ocular anatomy that may be present and come into contact with any element or group of elements of the ocular device in any configuration as a result of vision motions.

Figure 7A:
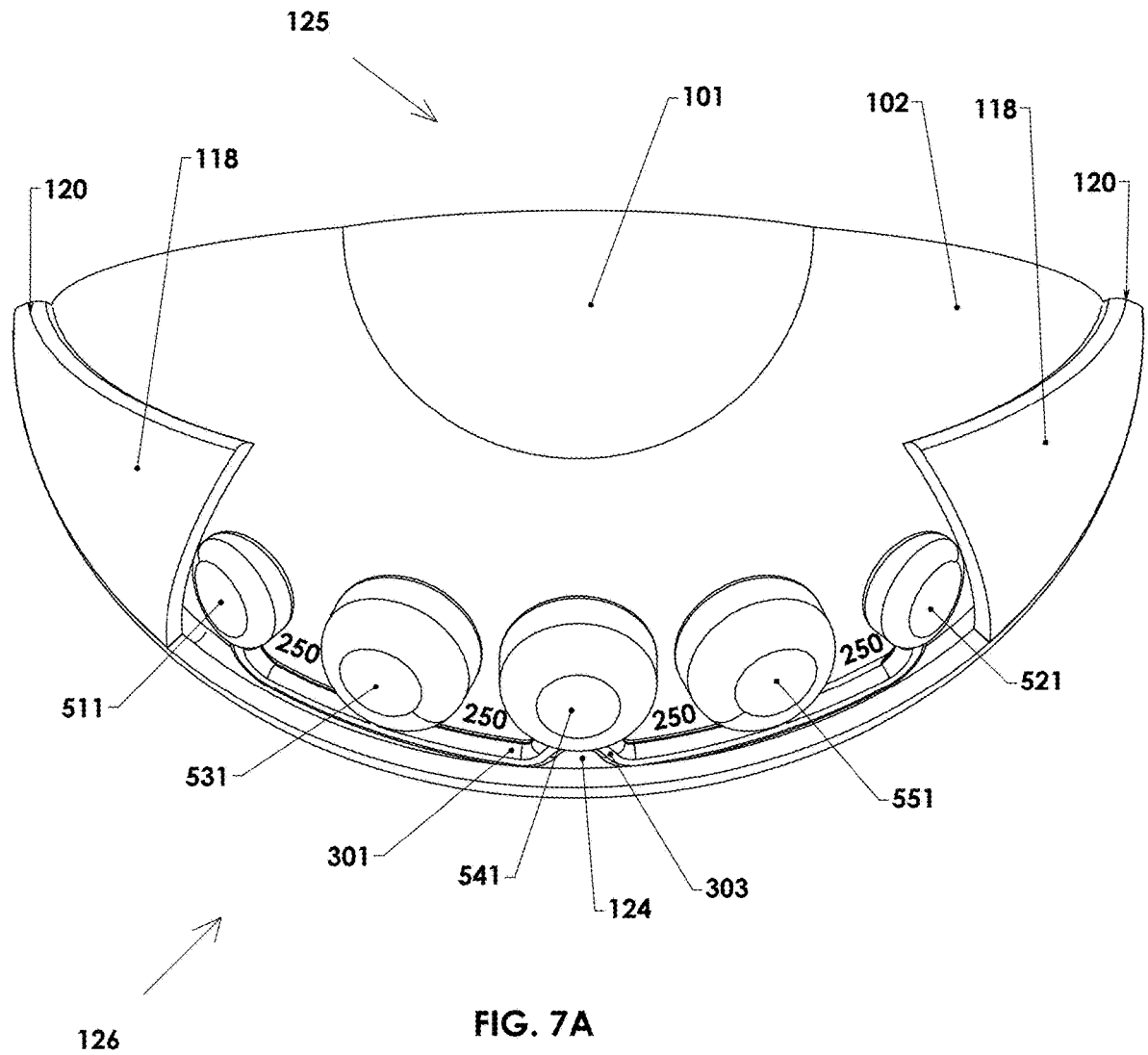
FIG. 7A is a front view of a portion of an eye, with the lower eyelid partially cut away to reveal an ocular device placed and seated in the eye.

FIG. 7A is an isometric, front view of a portion of an eye 125 illustrating placement of an ocular device 126 under a lower eyelid 118. The lower eyelid has been partially cut away in FIG. 7A, to reveal a device placed and seated and oriented with the elongated support member toward the fornix of the eye. Engagement of the inner surface of the eyelid with ocular devices can be negatively impacted by changes in the eyelid such as drape. Drape is the natural conjunctiva sac space of an eyelid where a portion of the ocular device may reside. The ocular device 126 is adaptive and can engage with eyelids that are of increased size or that are floppy or draped. Typically, eyelids of the over 50 years of age population group, which is most impacted by ocular disease, may have a larger conjunctiva sac for ocular device placement. The ocular device shown in FIG. 7A has degrees of freedom that enable the device to adjust and adapt to and fit within surrounding ocular surfaces. A portion of the elongated support member is visible as a result of the eyelid cutaway spanning the width of an ocular device configuration width to illustrate an example of placement of the ocular device with the elongated support member oriented toward the fornix of the eye.

Plates 511, 521, which are positioned adjacent to the canthi of the eye 120 and linked to the elongated support member 301, have each adapted by rotation to fit to both the eyelid 118 spanning across the eyelid interacting surface (partially cut away) and the local sclera surface 102. Plates 531, 541, and 551, which are linked to the elongated support member 301, have adapted by rotation(s) to fit to both the eyelid 118 spanning across the eyelid interacting surface (cut away) and the local sclera surface 102. Open space 250, shown in FIG. 7A within the confines of the ocular device and bound by the eyelid and sclera surfaces, provides additional space to retain tear fluid, assisting in achieving larger tear fluid volume.

The plates function to direct the natural eyelid forces and eyelid tension through the ocular device in a balanced manner to keep the device located under an eyelid with minimal surface contact area to the saccadic surface kinetic influence.

Plates 531, 541, and 551, as examples, have sufficient mass and height as related to plates 511 and 521, which are configured to be positioned adjacent to the canthi of the eye, to interact with the eyelid along its span correctly. The arrangement causes the device to behave as if it were monolithic, resulting in a device that is comfortable in the eye and capable of accommodating the natural reduction of eyelid tension due to tissue elasticity and distance from the canthi.

Figure 7B:
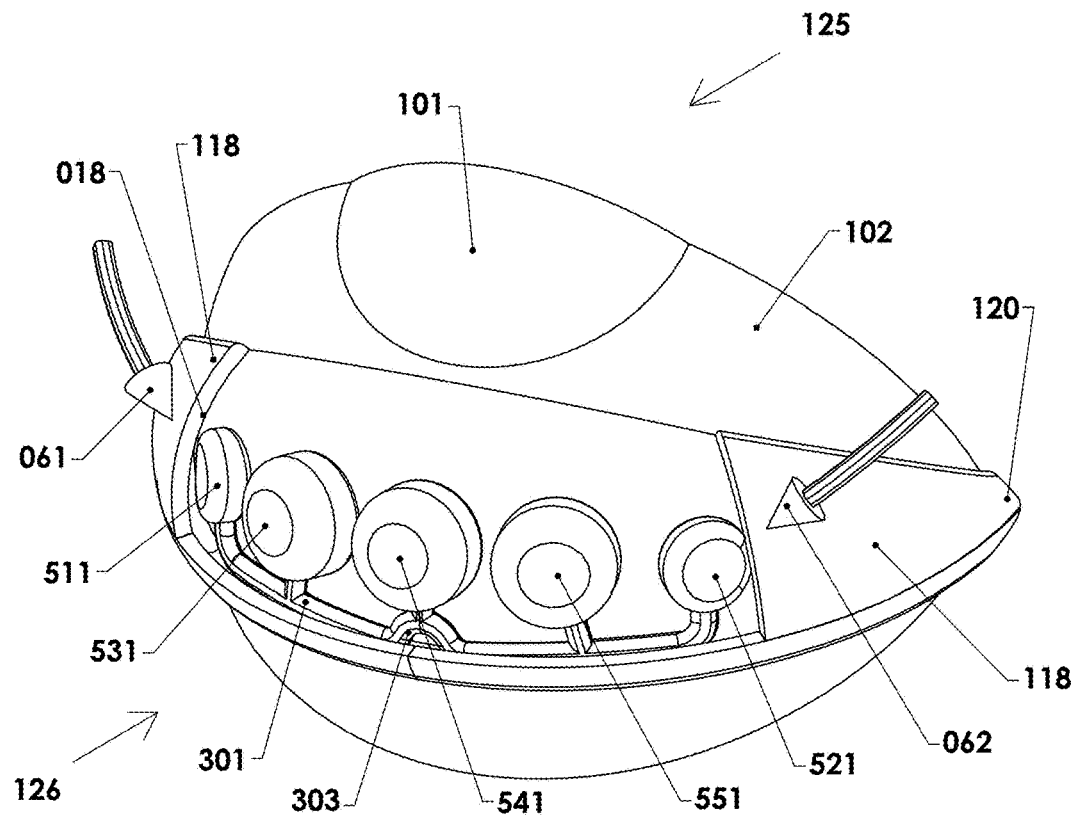
FIG. 7B is an isometric view of the eye and ocular device of FIG. 7A, indicating eyelid force vectors that position and retain the device.

In FIG. 7B, eyeball 125 and ocular device 126 (see FIG. 7A) are shown in isometric view including cornea 101, sclera 102, lower eyelid 118, and canthi 120. Lower eyelid 118 is cut away centrally to reveal ocular device 126. Elongated support member 301 is shown adapted adjacent to the fornix. Arch 303 rises upward from the fornix along the surface of sclera 102 adapting to optical anatomy in and around arch 303. Plates 511, 521 adjacent to the canthi of the eye 120 moved and rotated to fit to eyelid 118 and scleral surface 102. Plates 531, 541, 551, linked to the elongated support member 301 moved and rotated to fit to both the eyelid 118 spanning across surface of the eyelid (cut away in FIG. 7B) and scleral surface 102. Eyelid force direction vector arrow 062 is indicating a down and central application of under-the-eyelid force on plate 521. Eyelid force direction vector arrow 061 is also indicating a down and central application of under-the-eyelid force on plate 511. Eyelid pressure force on each plate adjacent to a canthus (511 and 521), generally directed toward the vertical meridian and the conjunctival fornix, results in a self-centering capability within the central conjunctival sac of an eyelid. FIG. 7B shows eyelid force direction vector arrow 061 indicates a down and central application of under-the-eyelid force on plate 511 toward the fornix and toward the vertical meridian anatomy. Applied forces to the ocular device 126 are a result of volume and eyelid tension of the canthi to the plate 511 eyelid span section of eyelid 118 including a conjunctival sac eyelid "drape" effect of the eyelid inner surface 018 engagement with plate 511 with the section cut extended toward the vertical meridian (the eyelid extension is not shown). Eyelid force direction vector arrow 062, as seen in FIG. 7B, indicates the down and central application of under-the-eyelid force on plate 521 toward the fornix and also toward the vertical meridian anatomy as applied forces to the ocular device 126. The applied forces are the result of the volume and eyelid tension of the canthi 120 to the plate 521 eyelid span section 118 including the eyelid "drape" effect of an eyelid inner surface engagement to the plate 521. Eyelid pressure force on plate(s) closest to the vertical meridian (see FIG. 7C), caused by central eyelid drape and generally directed toward the conjunctival fornix, results in a retention capability, resistant to ejection from saccadic eye motion.

Figure 7C:
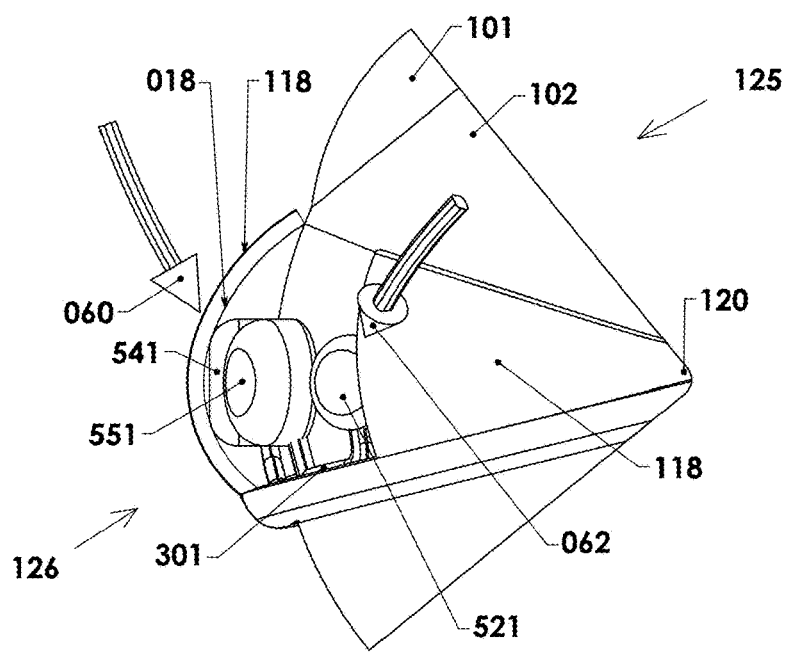
FIG. 7C is a side view of the eye and ocular device of FIG. 7A, with force vector(s) that show forces that retain the device under the eyelid.

FIG. 7C depicts the span of the eyelid over the center portion of device 126 and the under the eyelid sac 018 in contact with the device and the pressure of the eyelid sac tissue on the device underneath. Eyelid force direction vector arrow 060 in FIG. 7C indicates the down and central application of the eyelid force on plate 541 and arch 303 (FIG. 7B) as the eyelid inner surface 018 accommodates the plate 541 (and all other plates) within the "conjunctival sac." The eyelid 118 is illustrated as a section view at the central meridian of the most central plate 541 of the ocular device. In FIG. 7C, eyeball 125 and ocular device 126 of FIG. 7B are shown in a right, side view including cornea 101, sclera 102, a lower eyelid 118, and canthi 120. Lower eyelid 118 is cut away centrally to reveal a placed and adapted ocular device 126. Elongated support member 301 is shown nesting and adapting under the eyelid, oriented toward the fornix.

Figure 7D:
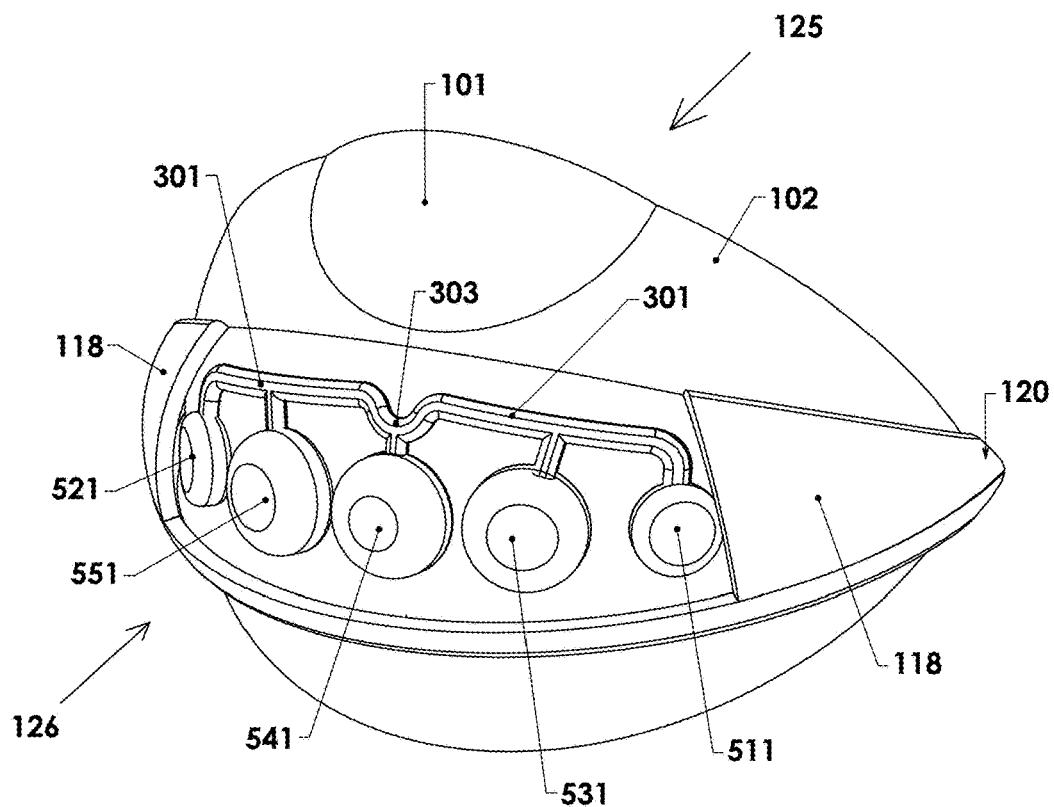
FIG. 7D is an isometric view a portion of an eye, with the lower eyelid partially cut away to reveal the ocular device of FIG. 7A placed and seated in the eye.

FIG. 7D is an isometric view a portion of an eye, with the lower lid partially cut away to reveal the ocular device of FIG. 7A placed and seated in the eye. In FIG. 7D, the ocular device is oriented with the plates toward the fornix of the eye.

Figure 7E:
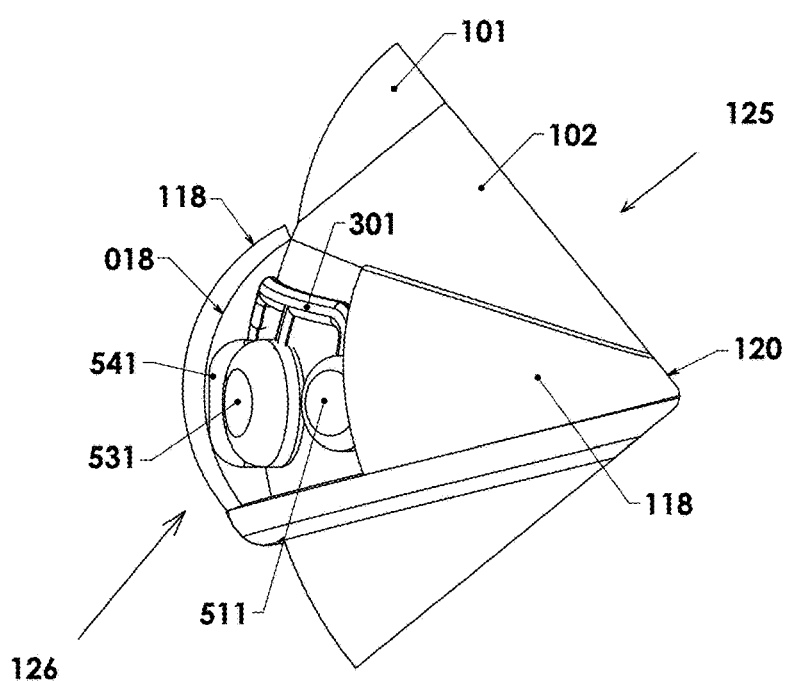
FIG. 7E is a side view of the eye and ocular device shown in FIG. 7D.

FIG. 7E is a side view of the eye and ocular device shown in FIG. 7D.

Figure 7F:
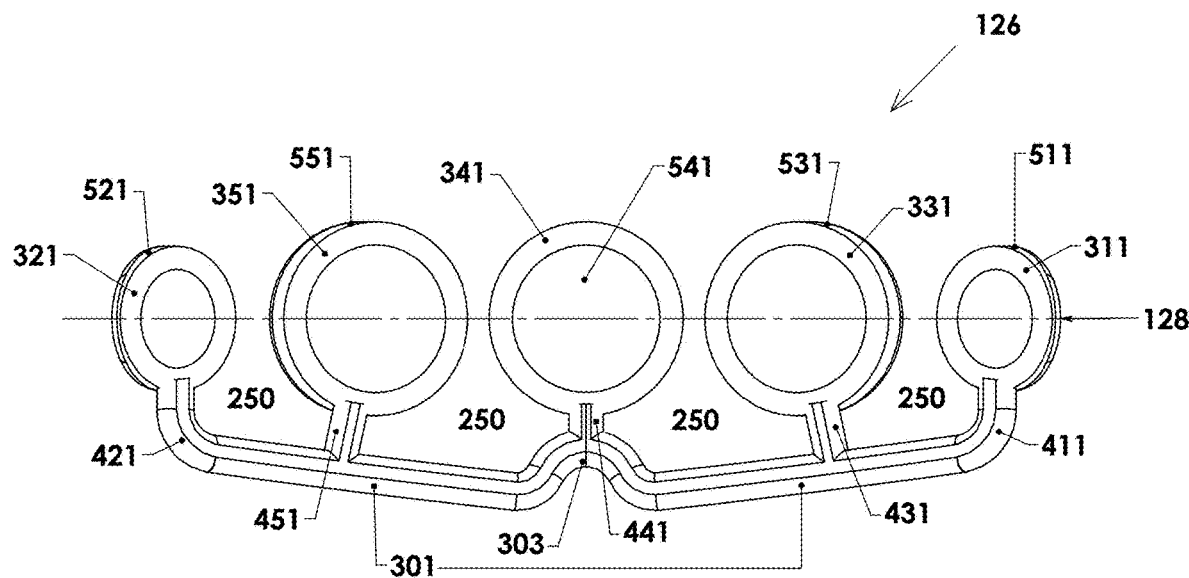
FIG. 7F is the back view of the device of FIG. 7A.

In FIG. 7F, ocular device 126 is shown as viewed from the back of the eye. All elements are adaptive with "degrees of freedom" capability that appear in FIGS. 7A to 7C, and open space 250 allows movement of features of ocular device 126. Attached to the elongated support member are plates 511, 521 adjacent to the canthi of the eye, linked to the elongated support member 301 by flexible connectors 411, 421 and plates 531, 541, 551 linked to the elongated support member 301 by flexible connectors 431, 441, 451, respectively. Plate 541 and flexible connector 441 link in the example in FIG. 7F to the elongated support member 301 at arch 303 in ocular device 126. Plates 511, 521, 531, 541, and 551 have anatomy adaptive torus style protrusions 311, 321, 331, 341, 351 projecting from the back planar sclera-adjacent surfaces of plates 511, 521, 531, 541, and 551, respectively. The elongated support member, flexible connectors, and protrusions provide surfaces for contacting the sclera. The remaining space comprises open space 250 providing empty space between and among features of ocular device 126 for independent and in-concert feature adaptability and degrees of freedom. The lower eyelid placement of the device, as illustrated, further provides an opportunity to retain generated tear fluid for a longer residence time within the ocular space within open space 250. The ocular device can instead be placed under the upper eyelid (not shown). Protrusions 311, 321, 331, 341, 351 project from the back surfaces of the plates, illustrating the surface interaction and relationship of protrusions that have a torus geometry. Protrusions have contact surfaces and can be of varied geometries, in addition to a torus or annulus. Protrusions can be bumps and other shapes that have a contact surface. The contact surface of the protrusions can be convex.

Figure 7G:
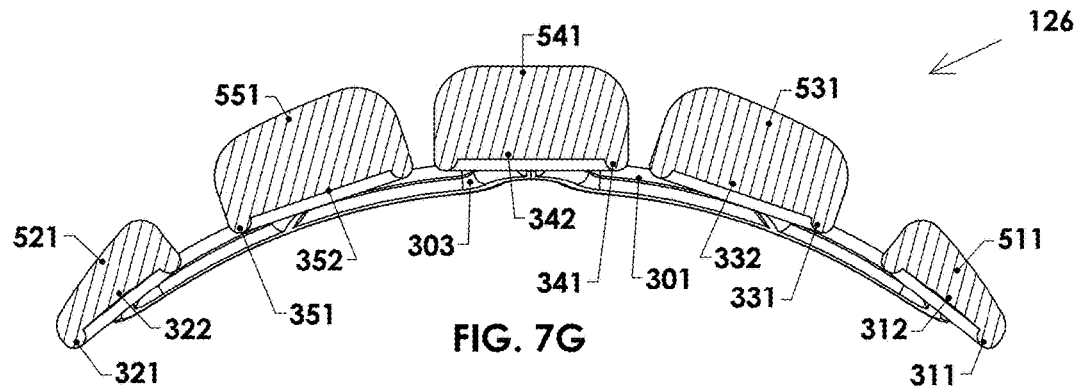
FIG. 7G is a top view of the ocular device shown in FIG. 7A, in cross-section on a horizontal plane.

In FIGS. 7F-7G, device 126 has plates 521, 551, 541, 531, and 511. FIG. 7F shows the back surfaces of the plates, which are configured to contact the sclera of the eye. Specifically, ocular device 126 has plates 521, 551, 541, 531, and 511 with back surfaces 322, 352, 342, 332, and 312 (shown in FIG. 7G), respectively, and the back surfaces have at least one protrusion, 321, 351, 341, 331, and 311, the protrusions having a convex contact surface to contact the sclera of the eye and to provide an offset space between the sclera and the back surface of the plate. The protrusion(s) can define a perimeter around offset space. The presence of offset space between the sclera and the back surface of the plate provides further adaptability to ocular anatomy, allowing for the formation of a tear fluid between the sclera and the ocular device. The protrusions in the example in FIG. 7F are toroidal, forming a complete annulus, as one example of protrusions on the back surface of an ocular device.

FIG. 7G is a horizontal cross-section through line 128 of ocular device 126, shown in FIG. 7F. The elongated support member 301 and arch 303 are shown as viewed from the top of the ocular device. Plates 521, 551, 541, 531, and 511 have protrusions 321, 351, 341, 331, and 311 respectively projecting from back surfaces 322, 352, 342, 332, and 312, respectively.

The ocular device torus feature as shown by FIG. 7F and FIG. 7G provides an ocular device that is atraumatic, with minimal surface contact. In FIG. 7G, back surfaces 322, 352, 342, 332, and 312 can be spaced apart from the surface of the sclera by protrusions so that tear fluid may collect in an offset space of the ocular device 126, providing the opportunity for increased tear fluid lubricity.

Interactions between protrusions on plates and an eyeball can be described by reference to a ring, which is similar to a protrusion that is a torus or an annulus, and a sphere, which is like an eyeball. For purposes of simplification, reference is made initially to rings and spheres as proxies for protrusions and eyeballs.

A ring of a set diameter less than the diameter of a sphere can seat itself on a sphere, regardless of the size of the sphere. The ring will find the correct circular surface on the sphere against which to seat itself, regardless of the orientation of the ring. Other geometric surfaces can also mate with each other on round surfaces, including, for example, the mating of convex and conical surfaces.

Applying these geometric principles to an ocular device, a protrusion, such as an annulus or torus, will interact with an eyeball so that the protrusion can seat itself on an eyeball regardless of the size of the eyeball or the location of the protrusion on the ocular device, providing adaptability to eyeballs of varying sizes.

The presence of at least one protrusion having a convex contact surface to contact the sclera of the eye and to provide an offset space between the sclera and the back surface of the plate decreases the surface area of the plate that is in direct contact with the eyeball. That is, the convex contact surfaces of the protrusion(s) are in contact with the sclera of the eyeball, and the surface area of the convex contact surface will generally be smaller than the surface area of the back surface of the plate. The application of this surface interaction geometric principle provides an ocular device with decreased stiction to adjacent surfaces.

It is advantageous to have an ocular device that manages surface displacements of rapid saccadic events and eye blinks with decreased impact to eye anatomy and increased patient comfort. An ocular device that is adaptive, provides an offset space, has decreased contact surface area, and is capable of accumulating tear fluid within its geometry provides a user a wearable device that is comfortable, with high lubricity, and allows for adaptation of the ocular device to a person's changing ocular anatomy and the variations of ocular anatomy in populations.

A device with protrusions in contact with an eyeball positioned under an eyelid of an eye that has rapid eye motion presents smooth blended atraumatic surfaces and minimal stiction in proximity to scleral and eyelid anatomy to minimize traumatic device interface during ocular saccadic motion. The result can be achieved without suturing a device to the eye. As more fully discussed hereinbelow, a device of this type can be used, for example, to deliver material to the eye.

Figure 7H:
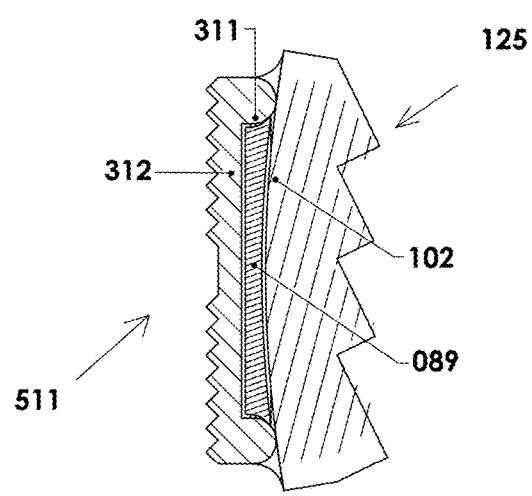
FIG. 7H is a cross-section exploded view of a plate of the device of FIG. 7A in contact with the sclera of a cutaway of an eyeball.

FIG. 7H illustrates a right, side section exploded cut view of plate 511 of the ocular device shown in FIG. 7G, as it would interact with sclera 102 of an eyeball to form offset space 089, with a tear fluid in the offset space. As shown in FIG. 7H, the design of example plate 511 allows the kinetically active translating sclera surface to be advantageously offset from plate 511 and in contact with a tear fluid. A tear fluid provides lubricity, which increases user comfort. The elongated support member, flexible connectors, and protrusions contact the sclera while maintaining offset space 089, retaining tear fluid in the offset space. The ocular device retains additional tear fluid in the ocular space for a longer residence time when placed under an eyelid, as illustrated, a result of features of the ocular device and surrounding open space 250 (see FIG. 7F). When the ocular device is inserted under the eyelid of the eye, the pharmaceutically active agent can be delivered to the eye by the tear fluid.

A 100-millisecond saccade duration for a 40-degree angular shift, providing 8+ mm surface translation (Table 3, FIG. 4A) is a significant surface translation distance relative to the eyelid. It is advantageous that an ocular device resident under an eyelid not adversely affect ocular anatomy during these events. The design intent of disclosed ocular devices is to generate a collected tear mass adjacent to the sclera to mitigate or minimize surface-to-surface contact between the ocular device and the sclera. A natural tear fluid may be retained by the ocular device or portion thereof, including a protrusion, as a result of its geometry. The ocular device, when in place in an eye, can "float" during saccadic translations as a result of the mass of tears accelerated by the surface translation kinetic motions, providing little resistance and reduced contact during these ocular motion events. Natural adaptations of the ocular device, including plates and protrusions from plates, to variation in ocular anatomy enable generation and retention of a tear fluid sufficient for this purpose.

In FIG. 7H, sclera surface 102 and plate 511 of FIG. 7G are shown in a sagittal plane section cut with additional material removed for clarity. Convex torus feature 311 of plate 511 is shown with the plate 511 fully adapted and in contact with the sclera surface 102 via the convex geometry 311. The bounds of the scleral surface 102, protrusion 311, and back surface 312 of plate 511, provide offset space 089 where a tear can form. Scleral motion in any direction will draw the tear fluid with it providing an ability to displace the plate 511 from scleral contact, thus increasing available tear volume and lubricity across scleral surface contact zones and to protrusions within the device perimeter.

Drug Delivery.

Described ocular devices can adapt to ocular anatomy. It is advantageous that these devices be comfortable within the ocular space, have decreased impact on patient vision, remain stable in placement and retention, and resist dynamic kinetic motions and forces of vision.

Ocular devices can be made to be capable of holding and delivering material such as a medication, pharmaceutically active agent, or drug or combinations of medications, pharmaceutically active agent or drugs (collectively referred to as "pharmaceutically active agent" or "drug") to the user. The drug can be in the ocular device itself, in a drug insert, or both. For example, a drug can be in a plate of an ocular device. A drug may also be applied through a port to the device while the device is in a delivery system, for example as part of an insertion protocol. The drug may be singular or multiple within a plate or across multiple plates or as applied to the device through a delivery system port. For example, a plate can comprise a pocket and a drug can be in the pocket of the plate. Delivery of the drug can be achieved by transporting the drug to the ocular anatomy by varied transport mechanisms. It is advantageous that ocular devices and transport mechanisms be comfortable to the user and compatible with ocular anatomy and that the ocular device and transport mechanism be of a composition that will deliver the drug to the ocular anatomy at a prescribed dose rate and total dose amount for a known period of time. It is further advantageous to avoid process loss of drug in view of cost.

As an option, a drug insert (also referred to as "insert") can be used with an ocular device, with material, such as medicine, drug, or pharmaceutically active agent, in the drug insert, with the drug insert serving as a transport mechanism or as part of a method of delivery of a drug to an eye. The drug insert can be placed in the ocular device, for example in the plate of the ocular device. The drug insert can be placed in an insert pocket in the plate of the ocular device.

By way of example, a therapeutic medication or drug could be delivered to the eye of a user by combining ocular device 299 shown in FIG. 5A with a drug insert to provide a user with an adaptive ocular device for drug delivery.

FIG. 8A is a flowchart illustrating an example of a manufacturing process for clinical use device(s) according to an example embodiment.

FIG. 8B is a diagram illustrating performance attribute contributions of ocular device(s) and inserts (the drug delivery component) and the ocular device and inserts combined, using a Venn diagram illustrating singular and combined performance attributes. Drugs can be transported by tear fluid from an ocular device or from an ocular device with an insert. The tear fluid is a transport mechanism to deliver medication or drugs to both the eye and mucosal membrane absorption tissues. Medication transport occurs across and through the ocular anatomy in local proximity to an ocular device and can use a tear fluid to therapeutically target the ocular anatomy.

Figure 9B:
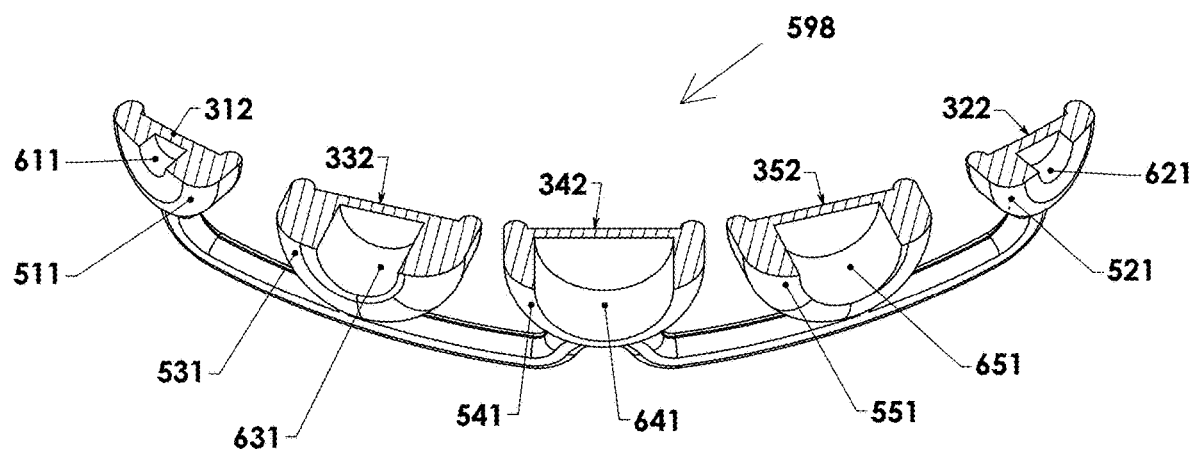
FIG. 9B is a front view of the device of FIG. 9A2 with inserts inserted in the plates.
Figure 9B:
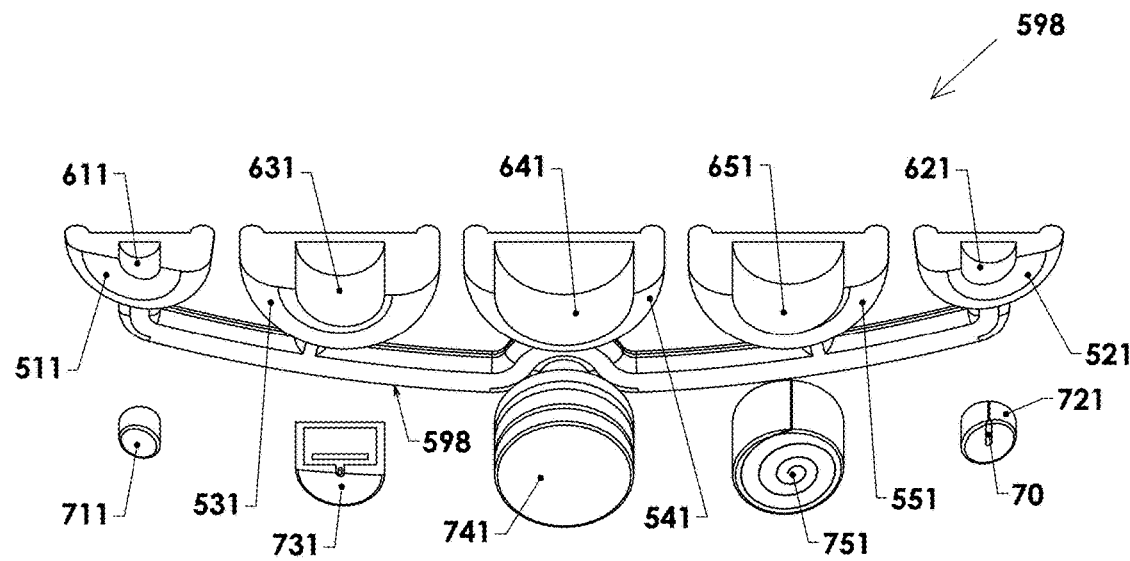
Figure 9B:
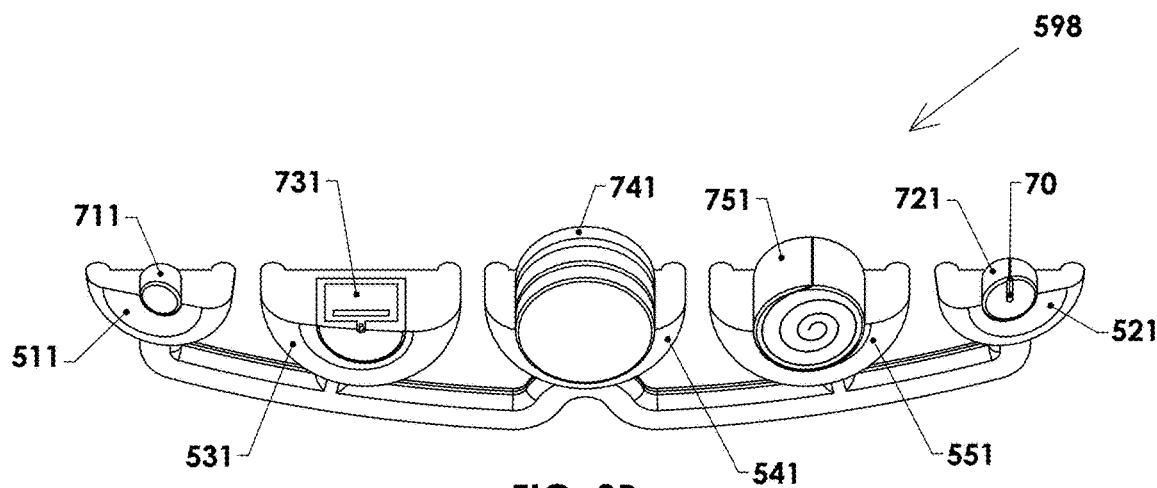

FIGS. 9A1, 9A2 and 9B illustrate an ocular device 598 that can be used for the delivery of material including drugs to an eye. FIG. 9A1 is a front view cross-section view of ocular device 598 with pockets. FIG. 9A2 is a front view of the device of FIG. 9A1 with inserts aligned to be inserted into the pockets in the plates. FIG. 9B is a front view of the device of FIG. 9A2 with the inserts inserted in the plates.

It is noteworthy that there is no constraint with regard to the method of placement of an insert in an ocular device or the method of delivery of drugs from an ocular device such as the ocular device shown in FIGS. 9A1, 9A2, and 9B. For example, the insert may be placed in an ocular device mechanically. As an illustration and not as a limitation, an insert can be placed mechanically in a pocket of a plate of an ocular device. As a further example, an insert can be generated in-situ by a polymerization. As an illustration and not as a limitation, silicone can be polymerized with a drug in a pocket of a plate of an ocular device. There is also no constraint on the method of delivery of a drug from an ocular device such as a device shown in FIGS. 9A1, 9A2, and 9B. For example, known methods of delivery of drugs may be used. Delivery of drug can be by a controlling flow membrane producing singular, multiple, or gradient medication delivery curve, and/or be driven by charged, non-charged or osmotic dose driving processes.

The design focus of the insert can be to achieve the dose-rate-time goal for any therapeutic medication agent(s), biologic agent(s), drug, medication, genetic interacting agent(s) ("gene therapy"), and/or delivery method.

Illustrations of configuration arrangements for ocular devices and inserts provide more detail and are not intended as limitations on the ocular devices and the inserts, alone or in combination.

FIG. 9A1 is a front view of ocular device 598 with the plates cut on a horizontal plane to reveal pockets. Ocular device 598 includes plates 511, 531, 541, 551, and 521, which comprise insert pockets 611, 631, 641, 651, and 621.

As a frame of reference, FIG. 9A1 identifies back surfaces 312, 332, 342, 352, and 322. Ocular device 598 is shown curved in FIG. 9A1 to illustrate it is able to adapt to the surface of an eyeball.

FIG. 9A2 is a front view of ocular device 598 of FIG. 9A1, with inserts 711, 731, 741, 751, and 721 aligned to be inserted into the pockets in the plates. A section view of insert 731 appears in FIG. 9A2, revealing a no material chamber with an orifice or hole to the chamber within. Insert 721 in FIG. 9A2 has a through hole to show a tubular or cylindrical style insert design.

To assemble the ocular device 598 and the inserts, insert 711 is placed and secured into pocket 611, within plate 511; insert 731 is placed and secured into pocket 631, within plate 531; insert 741 is placed and secured into pocket 641, within plate 541; insert 751 is placed and secured into pocket 651, within plate 551; and insert 721 is placed and secured into pocket 621, within plate 521.

The inserts shown in FIGS. 9A2 and 9B are configured to be assembled into the front side of the ocular device's plates.

FIG. 9B is a front view of ocular device 598 of FIG. 9A2, with inserts inserted in pockets in the plates.

Figure 10A:
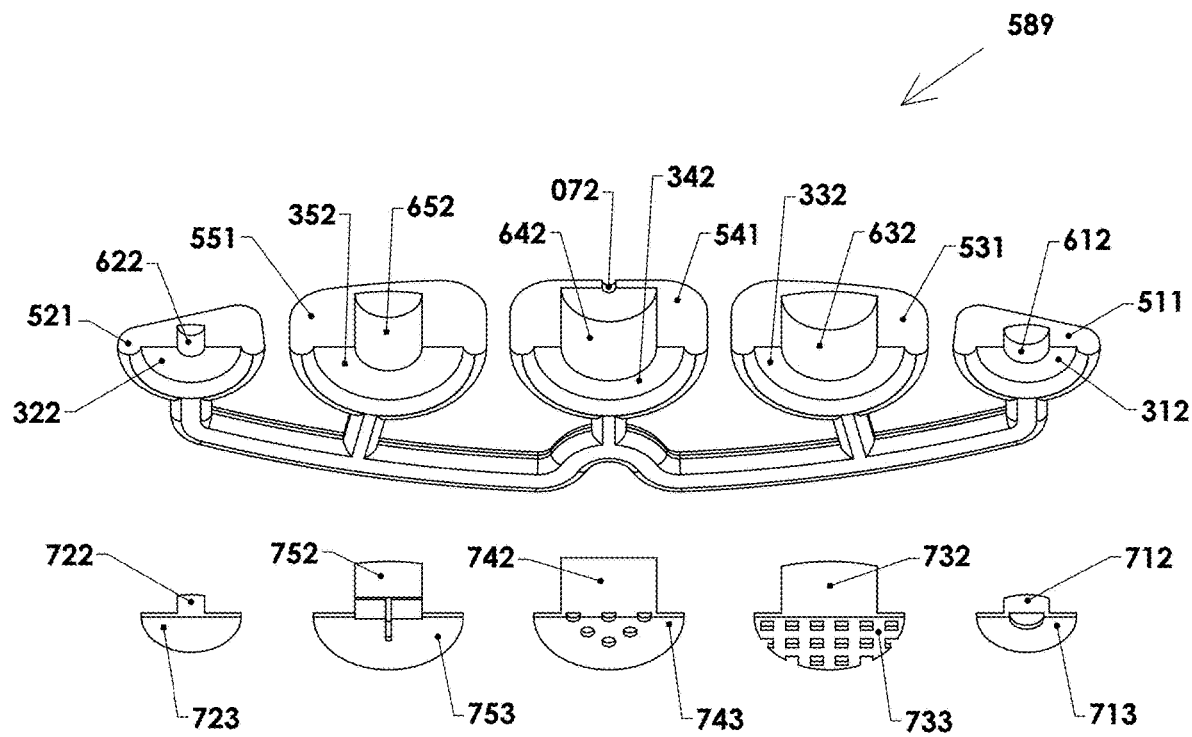
FIG. 10A is a front view of an ocular device with plates cut on a horizontal plane to reveal pockets in the plates, with different inserts aligned to be inserted into the pockets in each of the plates.
Figure 10B:
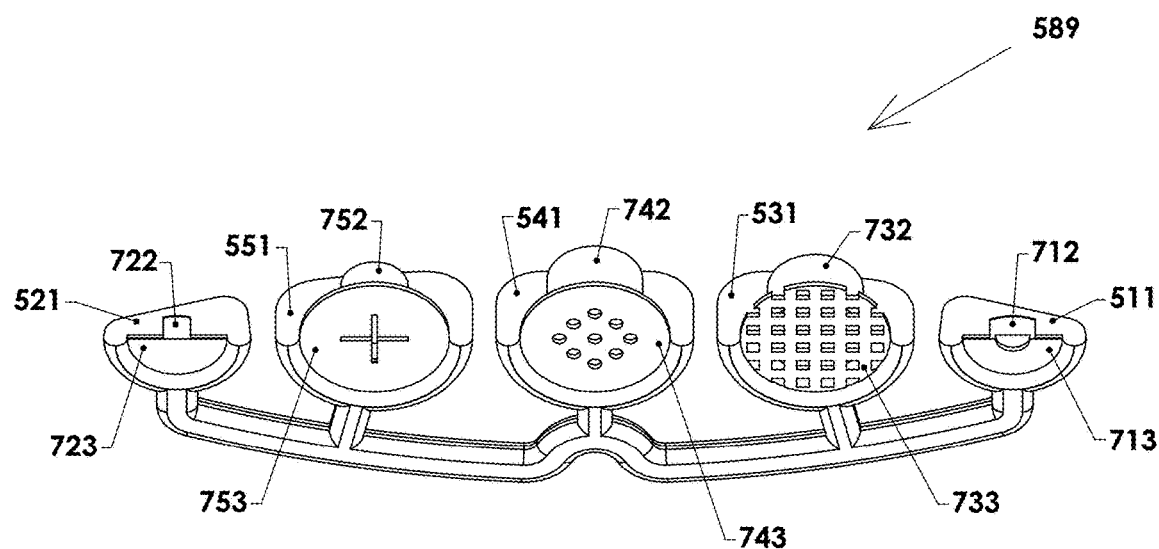
FIG. 10B is a front view of the ocular device of FIG. 10A with the inserts inserted in the plates.

FIGS. 10A and 10B illustrate ocular device 589. FIG. 10A is a front view of ocular device 589 with plates cut on a horizontal plane to reveal pockets in the plates. FIG. 10A is a front view showing ocular device 589 and different inserts aligned to be inserted into pockets in each of the plates. The inserts in FIG. 10A, have sealing membranes. Insert 712 has sealing membrane 713, insert 722 has sealing membrane 723, insert 732 has sealing membrane 733, insert 742 has sealing membrane 743, and insert 752 has sealing membrane 753. As an example, insert 712, with sealing membrane 713, is placed into pocket 612, and the membrane 713 is sealed to back surface 312 of plate 511. Insert 721 shown in FIG. 9A2 also has eyelid drug release orifice 70, providing a dual direction delivery system when used in combination with plate 541, with hole 072, of ocular device 589 illustrated by FIG. 10A. Insert 721 is an example of a cored insert with a hole through it.

FIG. 10B is a front view of the ocular device 589 of FIG. 10A, with the inserts inserted in the plates.

Therapeutic drugs may be delivered together or in sequence, using singular or multiple inserts and drug delivery techniques (see FIG. 9A2 insert 741).

Inserts and sealing membranes may be made using any volumetric shape as appropriate for the insert and sealing membrane design and function that will provide volume, including but not limited to: square, rectangular, triangular, polygon, circle, ellipse, sphere, spline surfaces, thin film, and combinations thereof, as appropriate. Such geometries would then also generate open space for an insert geometry to reside within and be retained.

The sealing membrane composition and design(s) that may be applied singularly or in combination with the inserts may be any suitable drug transport material and/or system, for example: porous materials, foams, grids, slit, orifices, woven, non-woven, permeable films, polymer films, layered, composites, laminates, metallic constructs, polar and non-polar properties, all useful examples of controlled release barriers which represent just a few of many possibilities in composition and construct.

Examples illustrate ocular devices to locate and retain inserts within the ocular anatomy, providing a comfortable adaptive ocular drug delivery system, which may contain inserts, to provide therapeutic clinical effects. The examples illustrate the depth, breadth, and versatility of disclosed ocular devices, across multiple possible drug delivery regimens.

Figure 11A:
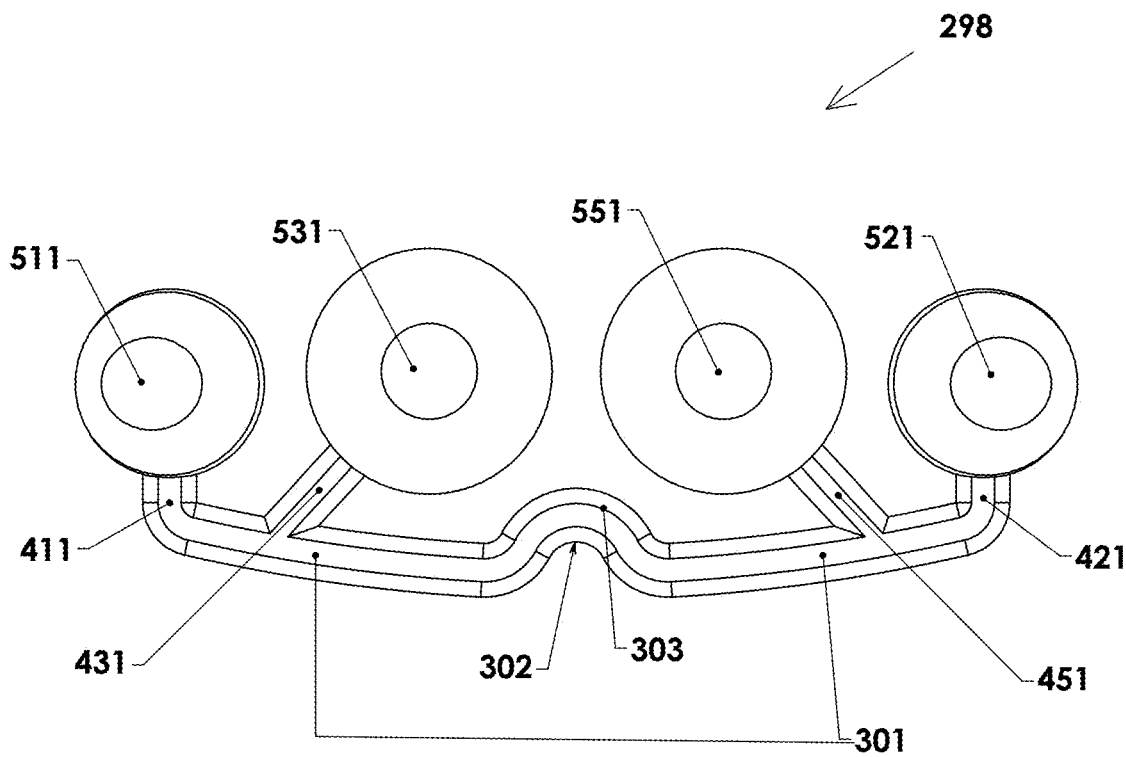
FIG. 11A is a front view of an ocular drug delivery system illustrating its component elements.
Figure 11B:
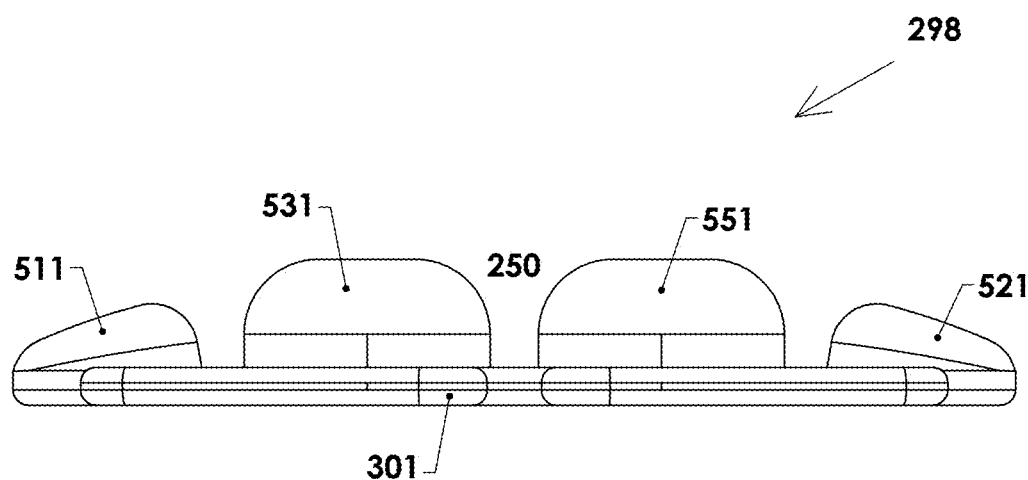
FIG. 11B is a bottom view of the system of FIG. 11A.

FIG. 11A shows a drug delivery system, with a front view of ocular device 298, and FIG. 11B is a bottom view of the system of FIG. 11A. Ocular device 298 comprises elongated support member 301, which has arch 303, is insertable under an eyelid where it can position itself to adapt to the anatomy and can rotate about its horizontal axis. When the ocular device is in place, elongated support member 301 extends toward each canthus of the eye, and plates 511 and 521 are connected at each end of elongated support member 301 by flexible connectors 411, 421. Between plates 511 and 521, plates 531, 551, which will adapt to ocular anatomy, are connected to the elongated support member 301 by flexible connectors 431 and 451. Open space 250 (shown for example in FIG. 11B) provides empty space between and among features of the ocular device 298, providing unoccupied volume for tear fluid retention within the confines of the ocular device and for independent and in concert adaptability of features of the ocular device. Plates 511, 531, 551, and 521, flexible connectors 411, 431, 451, and 421, and elongated support member 301, with arch 303, are adaptive, individually and in concert, to the ocular anatomy and provide an ocular device under an eyelid that can deliver medication or drugs to the eye.

Pockets within plates 511, 531, 551, and 521 allow for the placement and retention of medication or drugs to deliver a desired therapeutic effect.

Figure 12A:
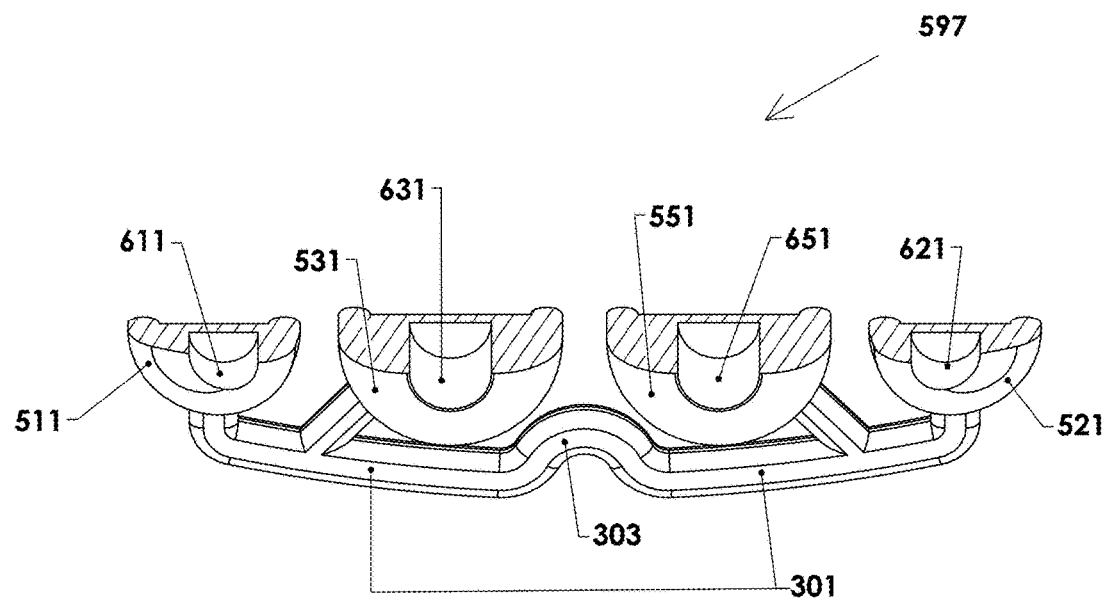
FIG. 12A is a front view of an ocular drug delivery system with plates cut on a horizontal plane to reveal pockets in the plates.

FIG. 12A depicts ocular device 597 illustrating elongated support member 301 with arch 303 shown connected to plates 511, 531, 551, and 521, which are cut on a horizontal plane to reveal pockets 611, 631, 651, and 621 in the plates, respectively.

The pocket is configured to hold an insert in a plate of the ocular device. The drug delivery rate over time can be controlled by adjusting a small diameter lip opening into which the insert is pressed, providing a mechanical retention system for an eroding or non-eroding insert.

Figure 12B:
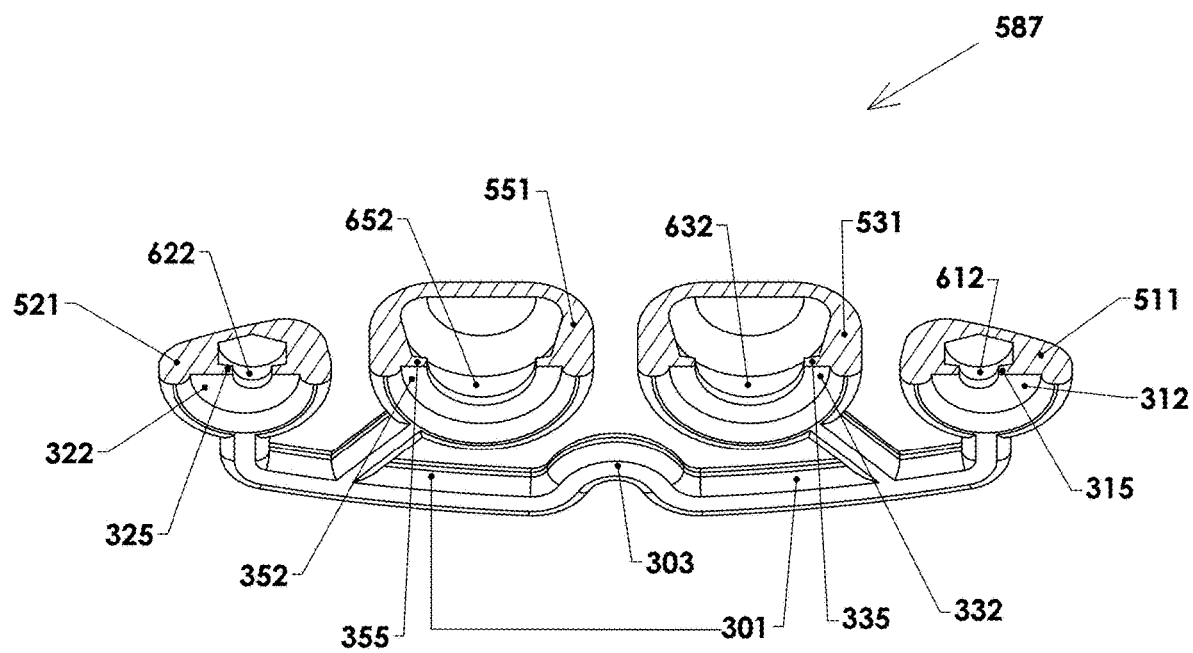
FIG. 12B is a back view of the ocular drug delivery system of FIG. 12A with plates cut on a horizontal plane to reveal pockets in the plates.

FIG. 12B illustrates ocular device 587. In addition to a membrane seal as previously described, ocular device 587 includes features for securing an insert so that the insert is designed to fit pockets 622, 652, 632, and 612, placed within the pockets is retained mechanically by retention features illustrated by 325, 355, 335, and 315, respectively. As shown, mechanical retention is achieved by a retention lip. There is no directional restriction for the addition of this feature, which may be included in the FIG. 12A ocular device as well.

Elongated support member 301 with arch 303 is shown connected to cross section views of plates 521, 551, 531, and 511 containing pockets 622, 652, 632, and 612 with back surfaces 322, 352, 332, and 312 are available for additional ease of membrane element sealing. Plates 551 and 531 are illustrated containing large volume pockets 632, 652, and optional membrane planar sealing features 332, 352 respectively.

Ocular device 587 may retain inserts. Features 315, 325, 335, and 355, can be configured to control drug delivery rate by controlling orifice size, while features 612, 622, 632, and 652, present the opportunity for delivery of a significant volume of drug, which can be sustained for a longer time duration by design and composition of the insert itself.

Figure 13A:
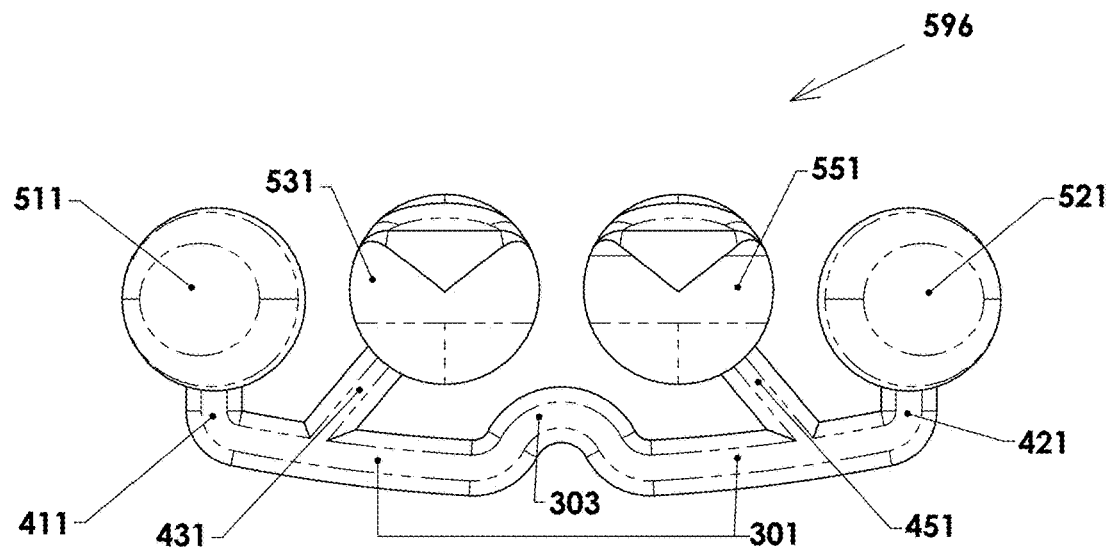
FIG. 13A is a front view of an ocular device.
Figure 13B:
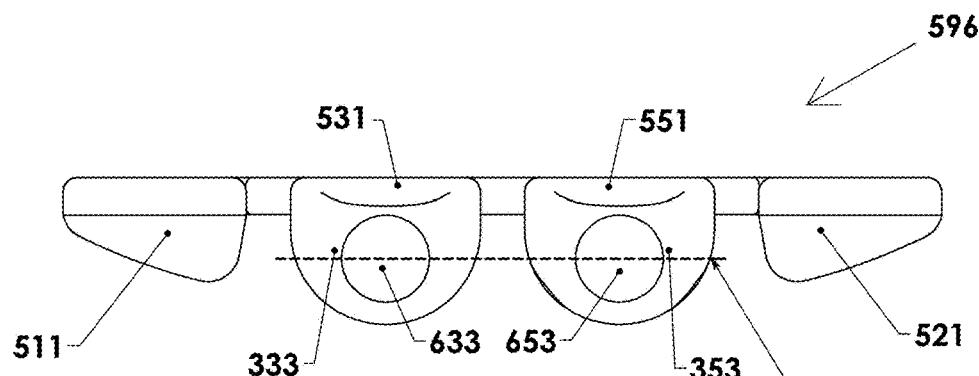
FIG. 13B is a top view of the device of FIG. 13A, showing pockets of plates and showing membrane sealing surfaces.
Figure 13C:
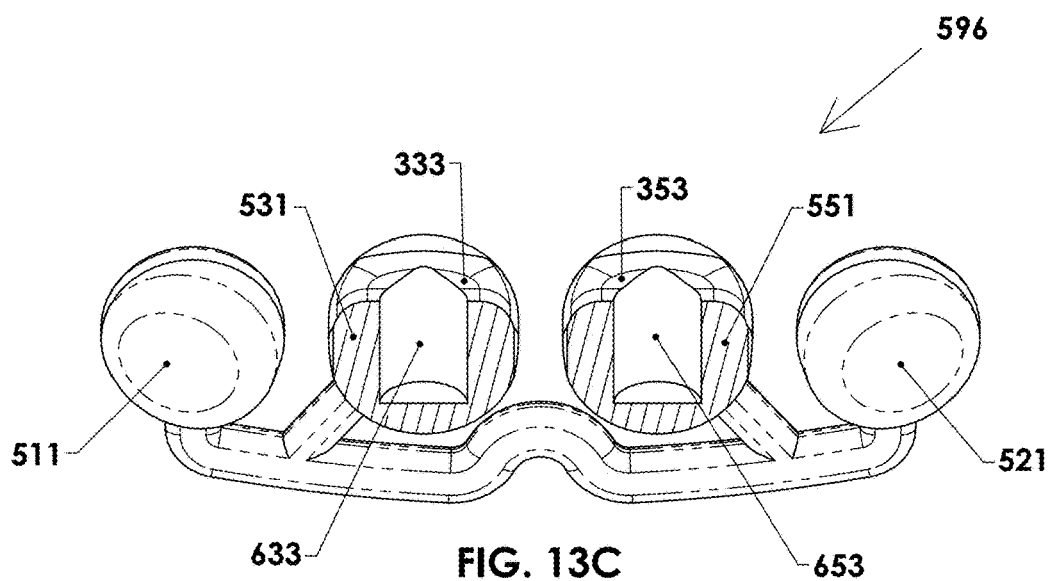
FIG. 13C is an illustration of the front view of the device of FIG. 13B, with plates cut open to reveal the inside of pockets.

FIGS. 13A, 13B, and 13C, illustrate ocular device 596, which is another example of an ocular device.

As illustrated in FIG. 13A, ocular device 596 is insertable under an eyelid and will adapt to variations ocular anatomy.

When the ocular device is in place, elongated support member 301 extends toward each canthus of the eye, and plates 511 and 521 are connected at each end of elongated support member 301 by flexible connectors 411, 421. Between plates 511 and 521, plates 531, 551, which will adapt to ocular anatomy, are connected to the elongated support member 301 by flexible connectors 431 and 451. Plates 511, 531, 551, and 521, flexible connectors 411, 431, 451, and 421, and elongated support member 301, with arch 303, are adaptive, individually and in concert, to the ocular anatomy and provide an ocular device under an eyelid that can deliver medication or drugs to the eye.

FIG. 13B is an illustration of the top view of ocular device 596. In FIG. 13B, plate 531 shows pocket 633 and sealing membrane 333. Plate 551 shows pocket 653 and a sealing membrane 353.

FIG. 13C is an illustration of the front view of ocular device 596 with plates 531 and 551 cut open to reveal the inside of pockets 633 and 653.

Figure 14A:
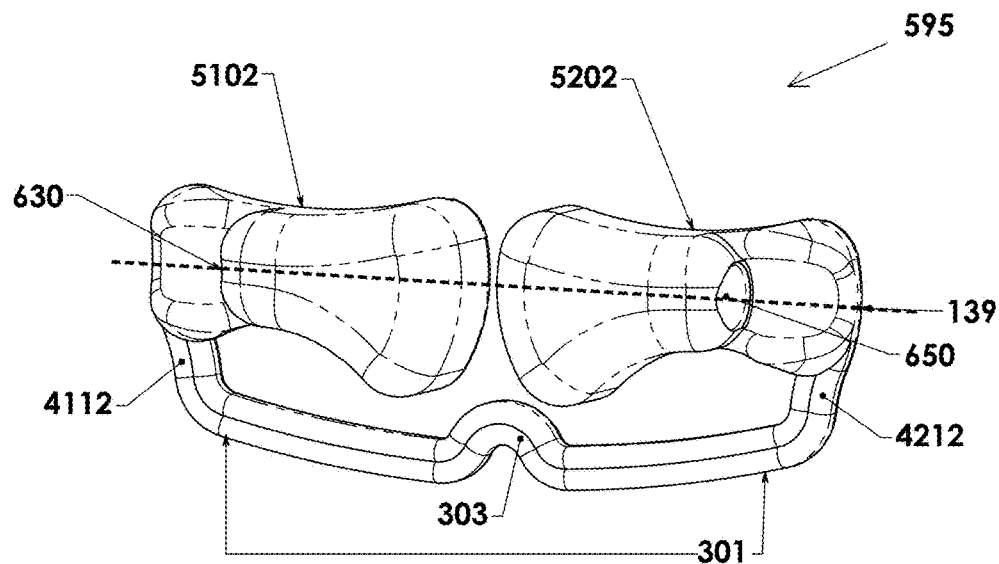
FIG. 14A is a front view of an ocular device.
Figure 14B:
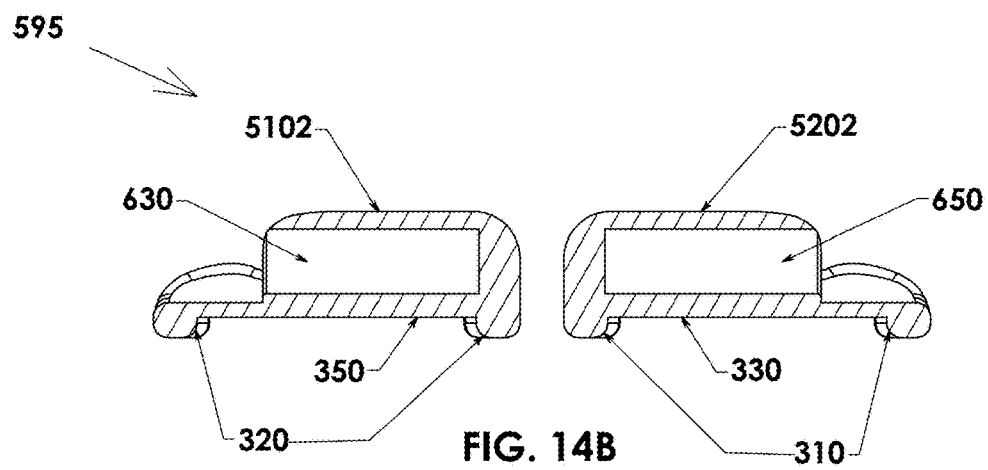
FIG. 14B is a bottom view of the ocular device of FIG. 14A, in cross section on a horizontal plane.
Figure 14C:
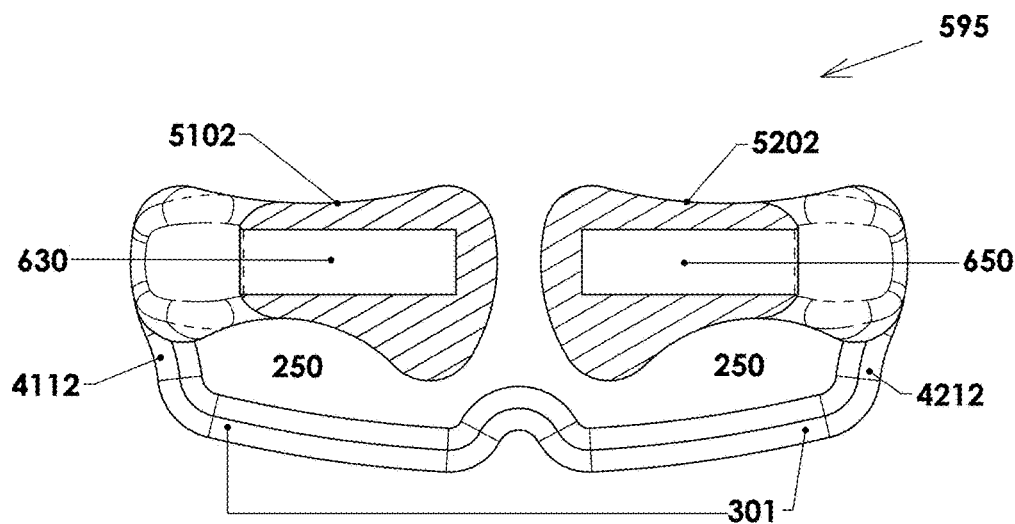
FIG. 14C is a front view of the ocular device of FIG. 14A, in cross section on a vertical plane.

FIGS. 14A, 14B, and 14C illustrate ocular device 595, which is another example of an ocular device. Ocular device 595 has plates with pockets that are of a larger volume.

FIG. 14A is a front view of ocular device 595. As illustrated in FIG. 14A, ocular device 595 includes elongated support member 301 with arch 303 and plates 5102 and 5202, which can be placed adjacent to the canthi of the eye, connected to the elongated support member 301 by flexible connectors 4112 and 4212, respectively. Plate 5102 has pocket 630 and plate 5202 has pocket 650. Pockets 630 and 650 can receive a substance, such as a drug for delivery to an eye.

FIG. 14B is a horizontal cross-section through line 139 of ocular device 595, shown in FIG. 14A. The figure shows a cross section of plate 5102 with pocket 630, protrusions 320, and back surface 350, and a cross section of plate 5202 with pocket 650, protrusions 310, and back surface 330.

FIG. 14C is a front view of ocular device 595 of FIG. 14A, in cross section on a vertical plane to reveal pockets 630 and 650.

Figure 15A:
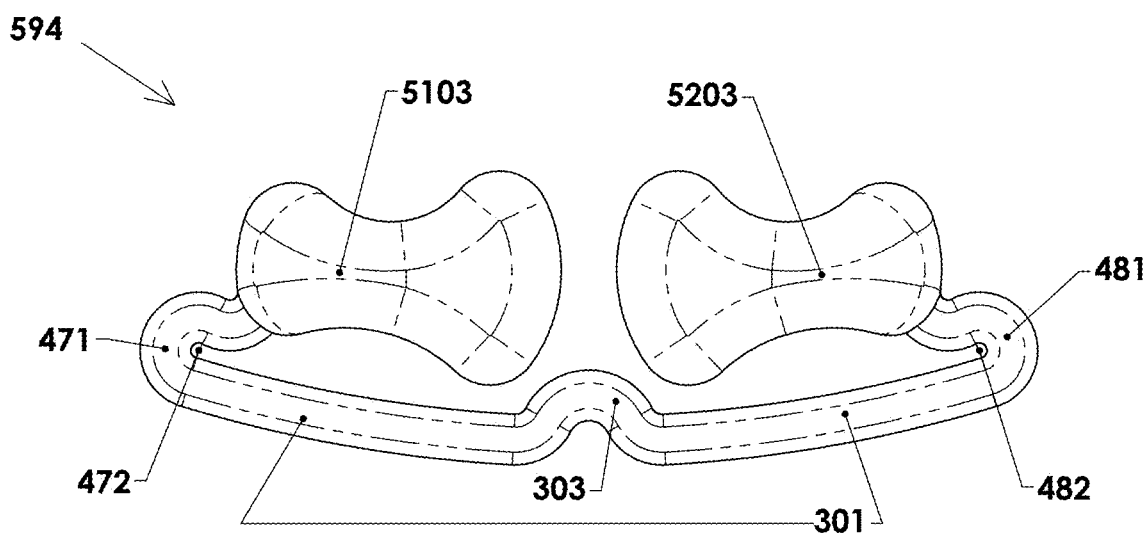
FIG. 15A is a front view of an ocular device.
Figure 15B:
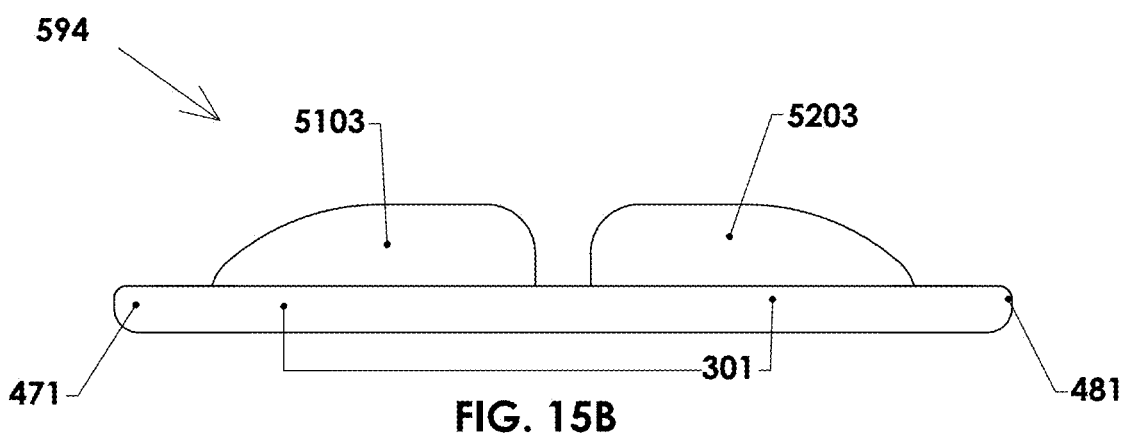
FIG. 15B is a bottom view of the ocular device of FIG. 15A.
Figure 15C:
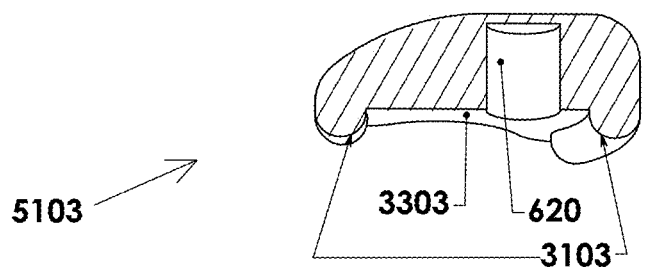
FIG. 15C is a partial cross section of a plate of the ocular device of FIG. 15A, showing a pocket opening on the back of the plate.

FIGS. 15A, 15B, and 15C illustrate ocular device 594, which is another example of an ocular device. Ocular device 594 has plates 5103 and 5203.

Ocular device 594 has a diminished conjunctival sac width and vertical height. As a result, ocular device 594 is advantageous for a user with an ocular anatomy that has a less voluminous conjunctival sac, for example, a user with a narrow palpebral fissure width, and decreased fornix depths.

As shown in FIG. 15A, the front side of ocular device 594 includes a segmented torus (see FIG. 22B) circumscribing the width of the plates 5103 and 5203. The elongated support member 301, when in an eye, extends toward each canthus of the eye. Flexible connectors 471 and 481 are configured to be located, when inserted in a user's eye, to be more distal toward the canthi while plates 5103 and 5203, adjacent to the canthi, are configured to be more central within the conjunctival sac eye anatomy. As a result, flexible connectors 471 and 481 project beyond the plates, positioning the plates so that when ocular device 594 is in an eye, the plates are toward the ocular vertical midline. As a result, ocular device 594 has a reduced width in the area of the plates for insertion within the conjunctival sac and a wider elongated support member.

Flexible connectors 471 and 481 curve vertically from the elongated support member 301, articulating around local origin pivots 472 and 482, to connect to the plates 5103 and 5203, respectively, in a spring loop like fashion. Ocular device 594 is capable of adjusting to anatomical forces, with the inclusion of spring like features, and the ocular device will retain a general controlled predictable shape outside the ocular space. A user is likely to be inclined to handle the insertion and removal of a device presenting a predictable shape, which provides features that have some similarity to a contact lens. Softer flexible adaptive material compositions may also be employed, without a loss of the desirable ease of user handling.

FIG. 15B illustrates a bottom view of ocular device 594 as shown in FIG. 15A.

FIG. 15C illustrates a partial section bottom view of plate 5103 of ocular device 594. Plate 5103 appears in FIG. 15C with an optional pocket 620 and protrusion 3103, which is torus-like and segmented (see FIG. 22B). Pocket 620 opens to the back surface 3303 of plate 5103 and is positioned so that when it is in an eye the pocket is adjacent to the sclera and offset from the surface of the sclera by protrusions 3103.

Figure 16A:
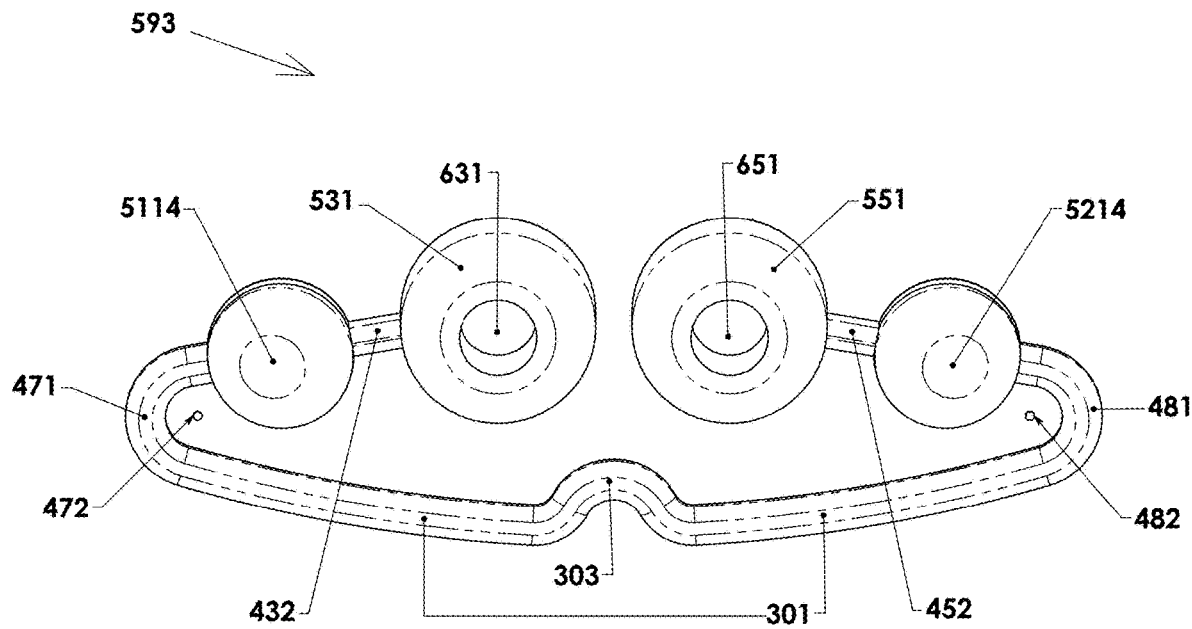
FIG. 16A is a front view of an ocular device.
Figure 16B:
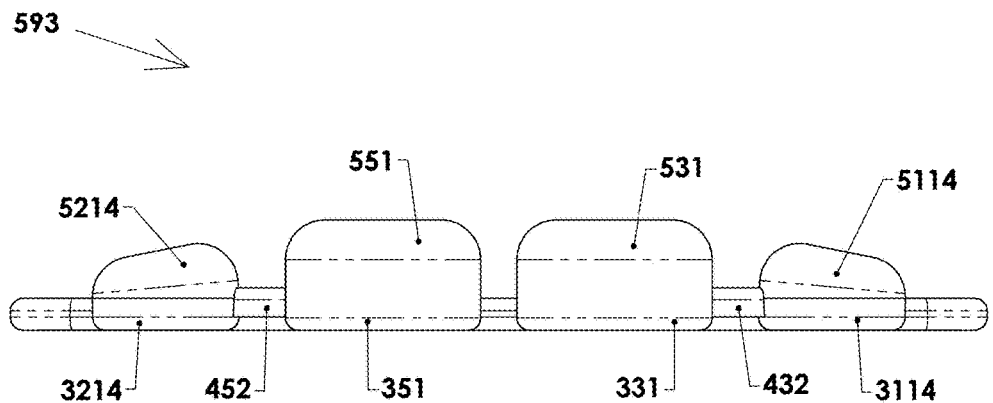
FIG. 16B is a top view of the ocular device of FIG. 16A, rotated 180°.

FIGS. 16A and 16B illustrate ocular device 593. In ocular device 593, the elongated support member 301 and flexible connectors curve around points 472 and 482 to connect with plates 5114 and 5214 and these plates connect to plates 531 and 551, respectively.

FIG. 16A is a front view of ocular device 593. In ocular device 593, there are four plates 5114, 531, 551, and 5214. Plates 531 and 551 have pockets 631 and 651, respectively. Plate 5114 is connected to elongated support member 301 by flexible connector 471 and to plate 531 by plate connector 432. Similarly, plate 5214 is connected to elongated support member 301 by flexible connector 481 and to plate 551 by plate connector 452.

Flexible connectors 471 and 481 connect to elongated support member 301 and curve around points 472 and 482 and connect to plates 5114 and 5214. The flexible connectors are configured to be located, when inserted in a user's eye, to be more distal toward the canthi, while plates 531 and 551 are configured to be more central within the eye anatomy.

As an alternative, the connection of plates 551, 5214, 5114, and 531 in FIG. 16A can be achieved by a support 452/481/301/471/432 that is imbedded in or travels through the plates as shown in FIG. 16A.

FIG. 16B is a top view of ocular device 593 shown in FIG. 16A, rotated 180° to show the link of plate 5114 to plate 531 by connector 432 and to show the link of plate 5214 to plate 551 by connector 452. As shown in FIG. 16B, connectors 432 and 452 can be offset from back surfaces 3114, 3214, 331, and 351, decreasing constraints on movement of plate connectors 432 and 452 that could be caused by eye anatomy surfaces.

Figure 17A:
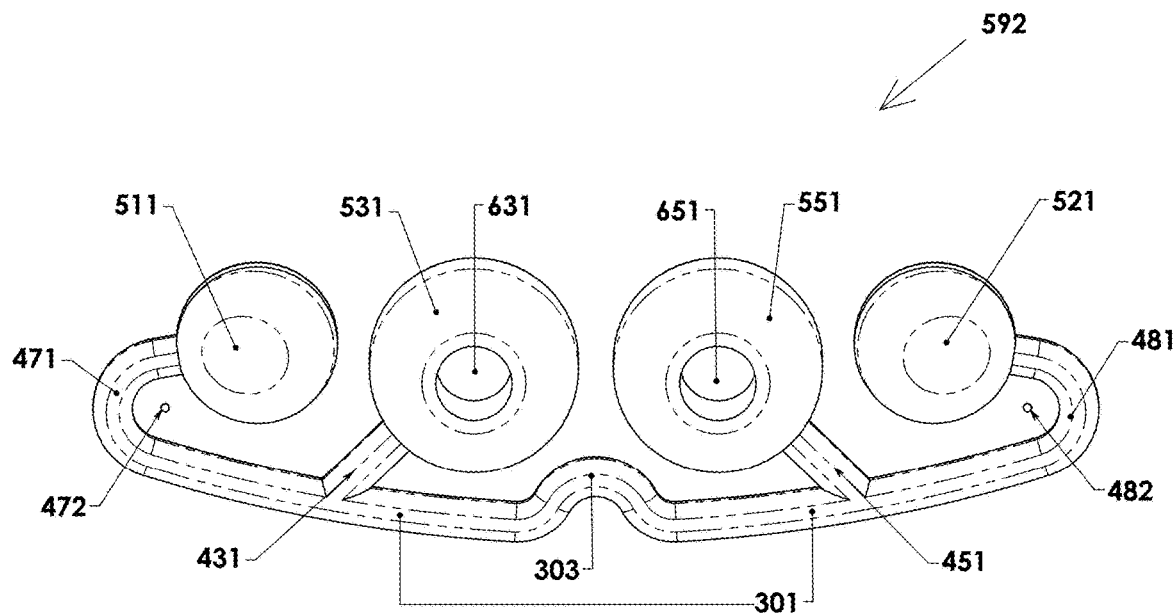
FIG. 17A is a front view of an ocular device.
Figure 17B:
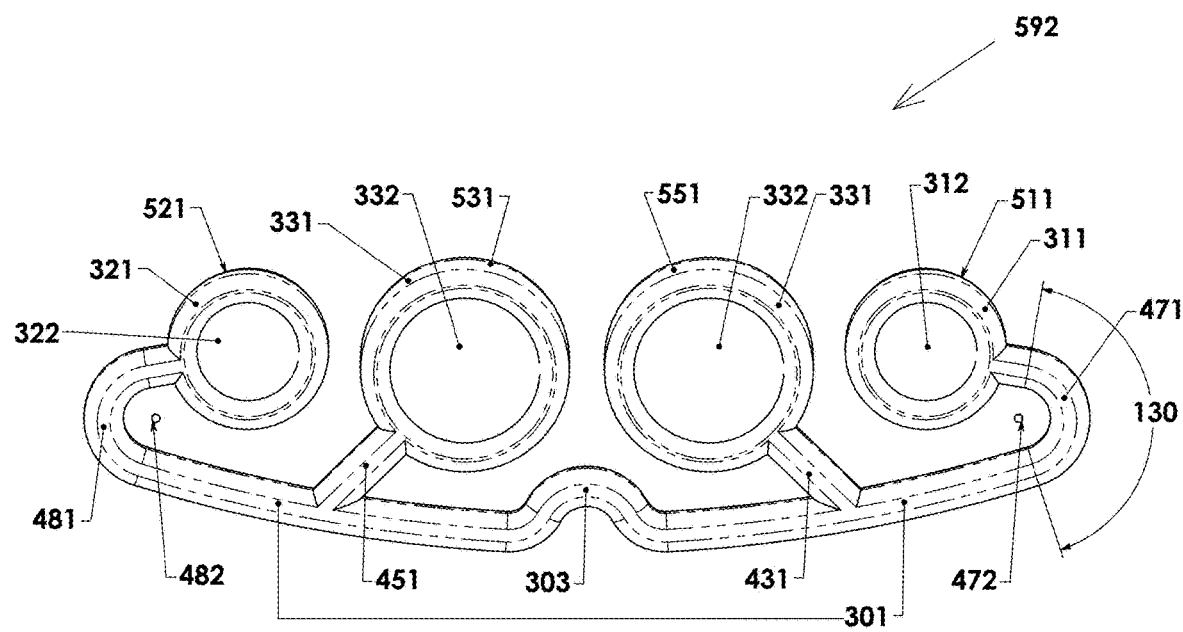
FIG. 17B is a back view of the ocular device of FIG. 17A.

FIGS. 17A and 17B illustrate ocular device 592. FIG. 17A illustrates a front view of ocular device 592, and FIG. 17B illustrates a back view of ocular device 592. Ocular device 592 is more compact than ocular devices 597 and 587 shown in FIG. 12A and FIG. 12B. In ocular device 592, each plate is connected to elongated support member 301 without an intervening plate.

FIG. 17B shows that flexible connectors 471 and 481 also curve around points 472 and 482 to form an outer angle 130. Outer angle 130 is obtuse. Further flexibility in providing devices that are adaptive to particular users can be achieved by providing devices with obtuse angles, acute angles, or a combination of obtuse and acute angles. Additional options are also available in the angle formed at the connection between each plate of an ocular device disclosed herein to the elongated support member in each disclosed ocular device. For example, in FIG. 11A, the angle formed between flexible connector 431 and elongated support member 301 to the left of the flexible connector is obtuse. In a particular device, the angle at which plates and flexible connectors connect to elongated support member can be the same or different.

FIGS. 18A, 18B and 18C illustrate ocular device 591. FIG. 18A is a front view of an ocular device. Ocular device 591 can be oriented with the back or the front of the plates toward the sclera. The protrusions on the plates of ocular device 591 are capable of engaging and adapting to the sclera and to the eyelid, which have curved surfaces, regardless of curvature, direction, or magnitude. Flexibility in the direction for placement of ocular device 591 results in simplified user instruction, and user training is also simplified.

FIG. 18B is a top view of ocular device 591 of FIG. 18A. It can be appreciated from FIGS. 18A and 18B that each feature of ocular device 592 is free to translate horizontally and vertically and to rotate on insertion to fit to the ocular anatomy, and each plate and protrusion is also free to adapt directionally, providing a device that can be inserted in either direction.

FIG. 18C is a top view of ocular device 591 of FIG. 18A, with the top portion of the plates cut away. The device is shown twisted about arch 303 to deviate the plates from the midline of the device, with plates 511 and 531 twisted opposite to plates 551 and 521 to illustrate fronts and backs of plates simultaneously. Plates 511, 531, 551, and 521 have protrusions 311, 331, 351, and 321 and "back surfaces" 312, 332, 352, and 322. Plates 531 and 551 have pockets 631 and 651, respectively. "Back surface" appears in quotations because 312, 332, 352, and 322 appear on both sides of their respective plates to highlight that ocular device 591 can be inserted in an eye in either direction.

FIGS. 19A to 19H illustrate ocular device 800 and isolated views of features of ocular device 800. Ocular device 800 has a large volume and can be inserted under an eyelid.

Figure 19A:
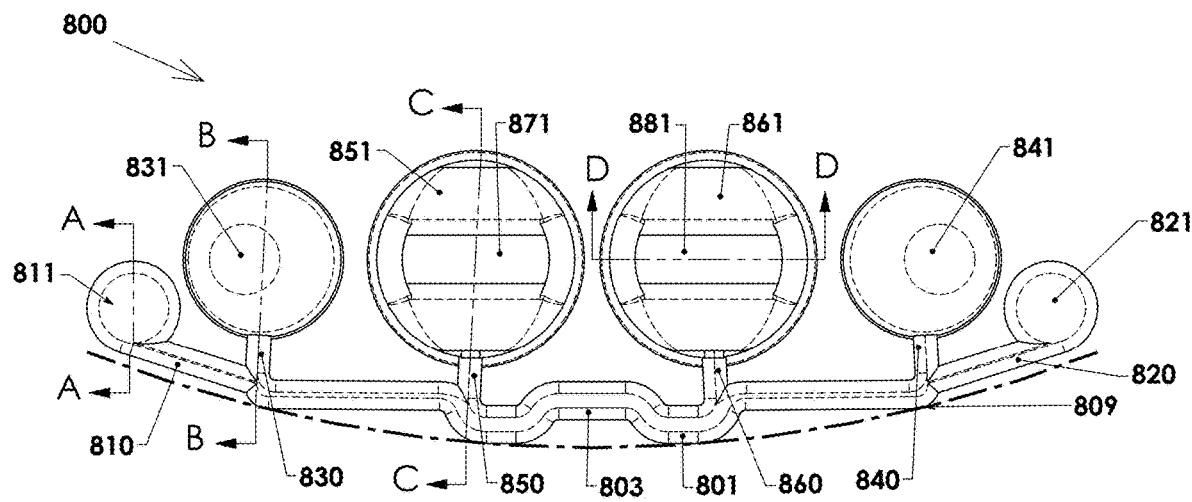
FIGS. 19A, 19B, and 19C are front, top, and back views, respectively, of an ocular device. The successive figures illustrate the device as it is rotated about the elongated support member toward the viewer in 90° rotational increments, while maintaining the left to right orientation.
Figure 19B:
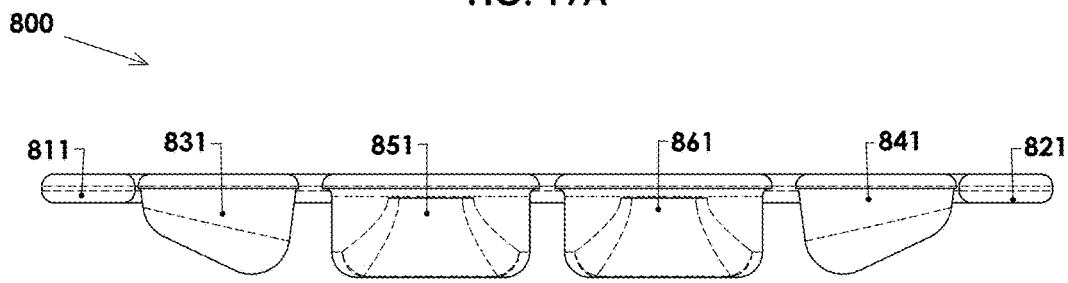
Figure 19C:
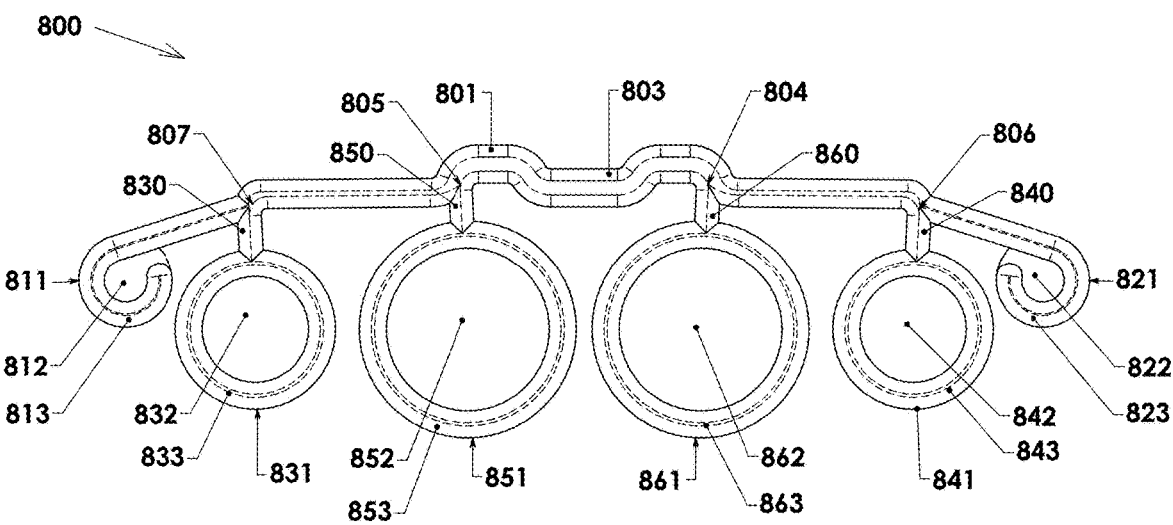

FIGS. 19A, 19B, and 19C are front, top, and back views, respectively, of ocular device 800. The successive figures illustrate the device as it is rotated about the support member toward the viewer in 90° rotational increments, while maintaining the left to right orientation.

As can be seen in FIG. 19A and FIG. 19C, elongated support member 801 is segmented, with variable cross-section, from a centered arch. The design of ocular device 800 can be advantageous for a thermoplastic injection molding manufacturing process, taking into account distribution of the flow of material. It can be appreciated from FIGS. 19A to 19C that ocular device 800 incorporates and adjusts features more fully described with reference to other ocular devices exemplified herein. Ocular device 800 allows for predictable adjustment of features and connectivity to accommodate numerous polymeric compositions, each with its own process and thermal dimensional characteristics.

The pockets in the plates present a large volume cylindrical pocket for drugs, or an insert containing drugs, that is compatible with well-known tablet manufacturing technology and assembled by snap-in mechanical assembly. Further sealing membranes as previously illustrated may be applied. The insert dimensions provide a pocket that has a large volume, advantageously providing a high drug weight to carrier weight ratio.

As shown in FIG. 19C, plates 812, 822, 832, 842, 852, and 862 are arrayed and span from canthus to canthus, generally. Protrusions 813, 823, 833, 843, 853, and 863 reside on plates 812, 822, 832, 842, 852, and 862, respectively, and have convex contact surfaces to contact the sclera of the eye and provide an offset space between the sclera and the back surfaces of the plates.

Flexible connectors 810, 820, 830, 840, 850, and 860 connect plates to elongated support member 801 (FIGS. 19A and 19C). Plates 812, 822, 832, 842, 852, and 862, which are flexibly connected along elongated support member 801, further comprise features 811, 821, 831, 841, 851, and 861, which are material on the front side of the plates that project toward and are in contact with the eyelid.

FIGS. 19D, 19E, 19F, and 19H are section views along lines A-A, B-B, C-C, and D-D, respectively, of the device of FIG. 19A.

Figure 19D:
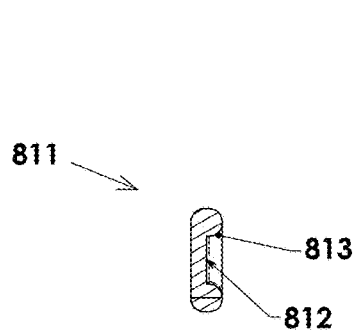
FIGS. 19D, 19E, 19F, and 19H are section views along lines A-A, B-B, C-C, and D-D, respectively, of the device of FIG. 19A.

As illustrated in FIG. 19D, plate 811 includes back surface 812 and protrusion 813, which has a convex contact surface to contact the sclera of the eye and to provide an offset space between the back surface and the sclera.

Figure 19E:
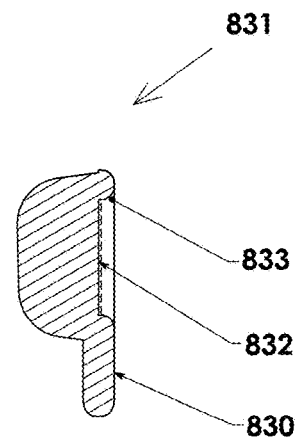

FIG. 19E illustrates plate 831 cut open, showing back surface 832 and protrusion 833, with an offset space between the sclera and back surface 832 of plate 831, and flexible connector 830.

Figure 19F:
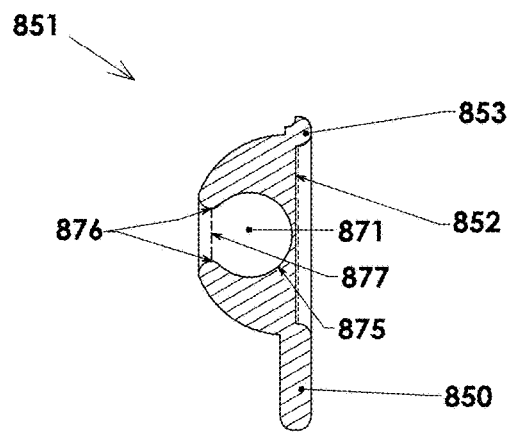

FIG. 19F illustrates plate 851 with pocket 871 and retention elements 875, 876 and 877 capable of retaining an insert. Pocket 871 is an example of a pocket that can accept a cylindrical insert, which can, for example, have radius 875 and a width (not shown) to be pushed by retaining lips 876 to reside and be secured within plate 851. The distance between retention lips 876 provides an orifice to pocket 871, seen in section view in FIGS. 19F and 19H and shown in front view in FIG. 19A.

Figure 19G:
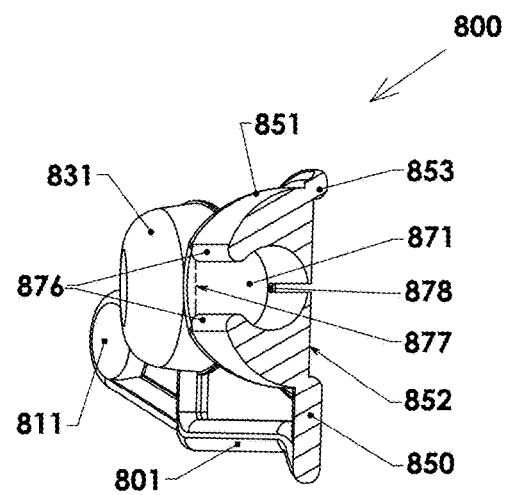
FIG. 19G is an isometric view of a portion of the ocular device of FIG. 19A, with a plate cut to show a pocket in the plate.

FIG. 19G is an isometric view of a portion ocular device 800 of FIG. 19, with a plate cut to reveal a pocket in the plate. FIG. 19G illustrates an alternative pocket, demonstrating optional eyelid and optional sclera controllable drug delivery ports. FIG. 19G shows further variation of the pocket arrangement in ocular device 800. Visible in FIG. 19G are elongated support member 801, plates 811, 831, and section cut of plate 851, with modified drug insert pocket 871. A pocket can be designed for delivery of a drug in more than one direction, such as a plate that provides for two directional delivery of medication. For example, pocket 871 shown in FIG. 19G has features shown in FIG. 19F, with the addition of orifice 878 through plate 851, providing a secondary delivery path for medication directly to the sclera through orifice 878.

Figure 19H:
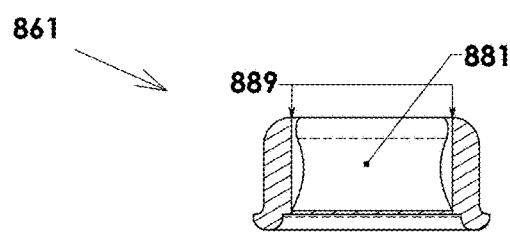

FIG. 19H shows plate 861 with pocket 881 and a transverse width 889. A cylindrical or rod shaped insert that holds a greater volume can be inserted transverse to plate 861. A cylindrical or rod shaped insert can be made with a greater volume of drug or other material to be delivered to an eye. A pocket can be of any geometric arrangement that secures an insert and exposes at least a portion of the surface of the insert to tears. Geometric features of an ocular device can be used to retain an insert, particularly within a pocket of an ocular device. As an example, and not as a limitation, an insert can be retained within the pocket of ocular device 800 by feature 876 shown in FIG. 19F and in FIG. 19G.

Figure 19I:
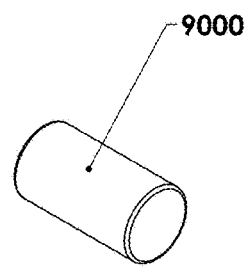
FIG. 19I is an isometric view of an example of an insert (or drug insert) that can be placed into an ocular device, including the ocular device of FIGS. 19A to 19H.

FIG. 19I is an isometric view of an example of a drug insert, or insert, that can be inserted in an ocular device, including the ocular device of FIGS. 19A to 19H. The insert in FIG. 19I is rod-shaped, which one example and not a limitation on the shape or size of an insert to be inserted in ocular device 800 or other ocular devices.

FIGS. 20A to 20G show an example of an orientation of pockets for drug inserts, shown along a generally transverse (horizontal) plane, to show pocket features. This illustration is not a limiting or restrictive "orientation" of any drug insert pocket. As nonexhaustive alternative examples, it may be compatible with manufacturing processing methods for a pocket to be aligned with flexible connectors or perpendicular to them.

FIG. 20A is a front view of ocular device 1008. In addition to ocular device features previously described that can also be seen in FIG. 20A, ocular device 1008 comprises support curves 1301 and 1304, which are separate from each other. It should be appreciated that pockets 1631 and 1651 in plates 1531 and 1551 can be transverse, as shown, or in another orientation.

Spanning the inside of arch 1303 is a horizontal surface 1302, providing an anchor about which other features may exercise their degrees of freedom. Horizontal surface 1302 also provides an attachment location for a manufacturing aid. See FIG. 6B and discussion hereinabove of underside 302 of arch 303.

FIG. 20B is a section view along line B-B of the ocular device of FIG. 20A, and FIG. 20C is a section view along line A-A of the ocular device of FIG. 20A. Ocular device 1008 has plates 1511, 1531, 1551, and 1521 that are further described, for example, in discussion of FIG. 20C. Protrusions 1311 and 1331 shown in FIG. 20B, are similar to features further shown and described, for example, in discussion of FIG. 21A to FIG. 21L. Pocket 1631 is similar to pockets further shown and described, for example, in FIGS. 19A to 19H.

FIG. 20C shows a cross section of plate 1531, with the back surface 1332 toward the right. As can be seen in FIG. 20C, pocket 1631 in plate 1531 has an elliptical perimeter cross-section of surface 1871. Pocket 1631 can trap an insert securely and provide sufficient "side-gap" and "end gap" for tear fluid access to the surface of an insert within the pocket. Retaining lip 1876 shown in FIG. 20C need not be a continuous feature across its span 1889 as shown in FIG. 20B; rather, retaining lip 1876 may be one or more "finger like" geometries, with material reliefs in and between them, for the passage of tear fluid into well 1631 and in contact with the insert surface 1900 as the insert resides within ocular device 1008. Insert 1900 is shown in FIG. 20C in dotted lines within pocket 1631. Insert 1900 fits within pocket 1631, which has an elliptical cross-section. An example insert length compatible with span 1889 of pocket 1631 is shown in FIG. 20B.

A pocket in a plate may have tear fluid transport capability in two or more differing directions described above with reference to orifice or hole 072 on plate 541 in FIG. 10A. Similarly, a plate of ocular device 1008 shown in FIGS. 20A, 20B, and 20C can include a hole, orifice, or slit, allowing drug to exit the pocket of the plate from the sclera side to provide a tear pathway into the pocket from the sclera side of the plate.

It should also be appreciated that a plate can include one or more snap in features that can mechanically retain inserts.

It should also be understood that pocket 1631 may be any useful shape that can capture and retain an insert.

Figure 20D:
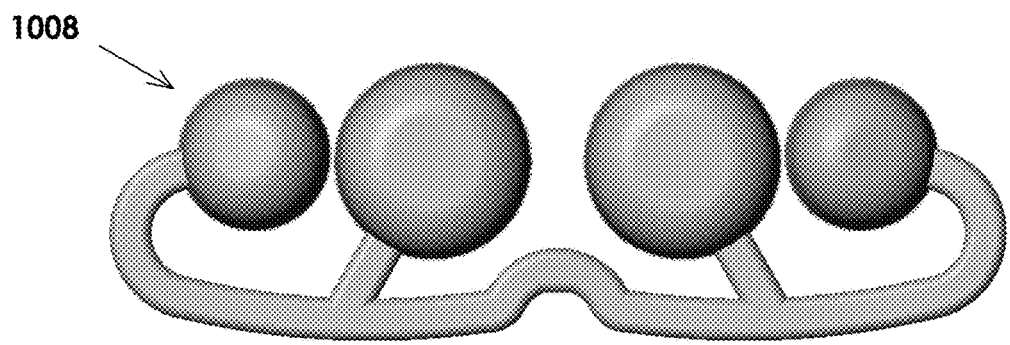
FIG. 20D is a front view of an ocular device of FIG. 20A simplified so that pockets do not appear in the plates.

FIG. 20D is a front view of an ocular device of FIG. 20A, simplified so that pockets do not appear in the plates.

Figure 20E:
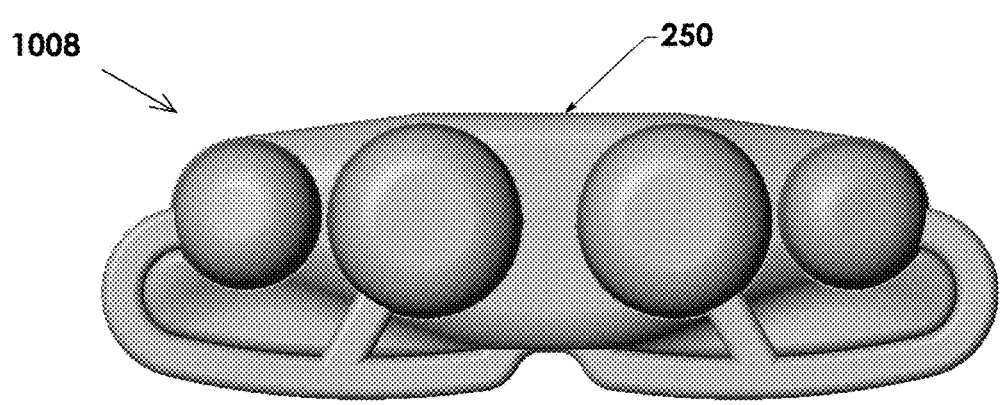
FIG. 20E is a front view of the ocular device as shown in FIG. 20D, with shading added to show open space 250 within the perimeter of the ocular device.

FIG. 20E is the ocular device as shown in FIG. 20D, with shading added to show open space 250 within the perimeter of the ocular device and bounded by the eyelid.

Figure 20F:
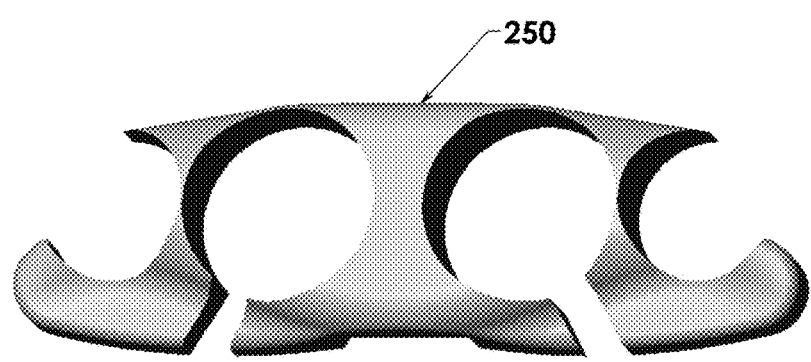
FIG. 20F is the open space of FIG. 20F with the ocular device removed.

FIG. 20F is the open space of FIG. 20E with the ocular device removed. When ocular device 1008 is inserted in an eye, tear fluid can fill the open space 250.

Figure 20G:
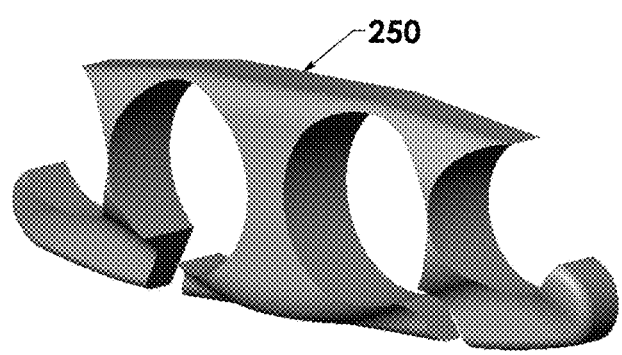
FIG. 20G is a view of the open space of FIG. 20F, turned 45 degrees.

FIG. 20G is a front view, at a 45-degree angle, of open space 250 of FIG. 20F. When in an eye, the eyelid drapes over the device to bound open space 250. See, for example, FIGS. 7A, 7B, and 7C.

In an ocular device, each plate with a pocket may contain an insert with a different pharmaceutically active agent. For example, 2 pockets with 2 different pharmaceutically active agents may reside within a single device. One pocket may have an insert with more than one active agent.

Human Ocular Compatibility and Comfort.

It is advantageous that an ocular device be compatible with human ocular anatomy and that the user find an ocular device to be comfortable. The following list provides features that can increase compatibility and comfort of an ocular device. The list is not a limitation on ocular devices disclosed herein.

Under the eyelid positioning.
Anchoring stabilizing geometry adjacent to the canthi maintains eyelid position and centration.
Minimal contact with sclera to decrease effect from eye saccadic motions.
Enhanced tear fluid volume retention and tear residence time for user comfort and consistent drug transport into ocular anatomy.
Optical quality polished surfaces to expand surface area, enhance tear fluid, and reduce eye motion friction factors.
Self-adaptability to a range of scleral and eyelid anatomy and local anatomical variance.
Total flexibility of therapeutic insert size, technique, composition and location.
Minimal ocular footprint configuration, compatible with smallest measures of ocular physiology.
Wide range of anatomical conjunctival sac width: fitting, configuration and design capability.
Hydrophilic ocular friendly carrier construct material compositions for patient comfort.

FIGS. 21A to 21L illustrate examples of plates and protrusions that may be an ocular device or be employed in ocular device(s), in varied configurations.

Figure 21A:
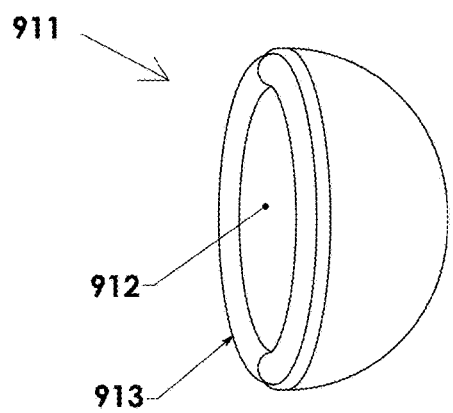
FIGS. 21A-21L illustrate examples of plates with protrusions.

FIG. 21A is a perspective view of an example plate 911 including back surface 912 with toroidal protrusion 913, which in this example forms a complete annulus.

Figure 21B:
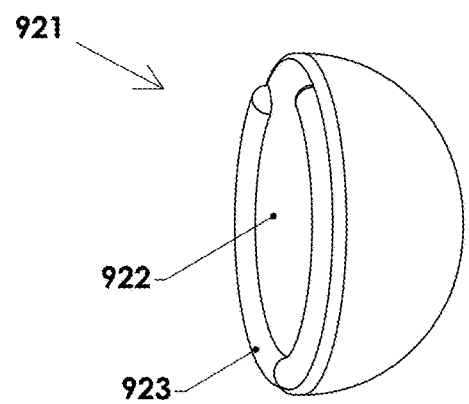

FIG. 21B is a perspective view of an example plate 921 including back surface 922 that includes protrusion 923, which in this example is an open segment of a torus.

Figure 21C:
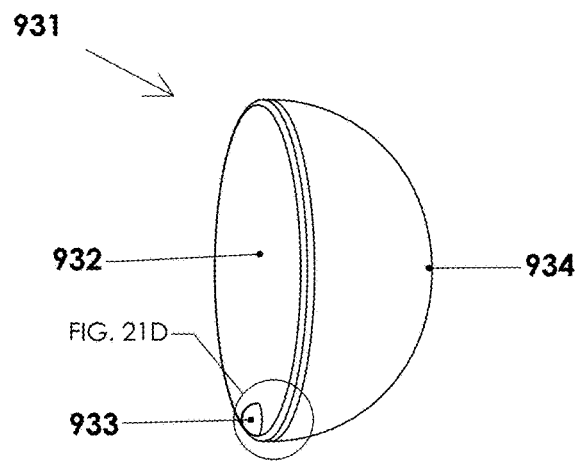
Figure 21D:
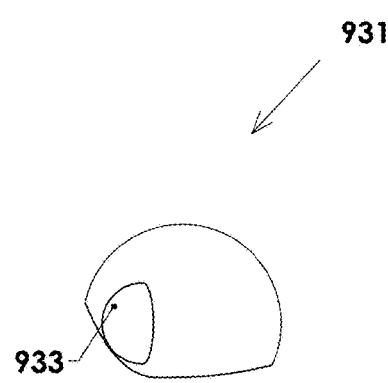

FIG. 21C is a perspective view of example plate 931 including back surface 932 that includes a single, dome-shaped protrusion 933 that is positioned off-center relative to the center of the plate 932. A magnified view of the small, off-center protrusion 933 is presented in FIG. 21D. FIG. 21C serves to illustrate that plate 931 can form a dome-shaped, curved surface 934, which projects in a direction opposite to that of protrusion 933. As can be seen in FIGS. 21A, 21B, and 21F, plates 911, 921, and 941 similarly form a dome-shaped, curved surface.

Figure 21E:
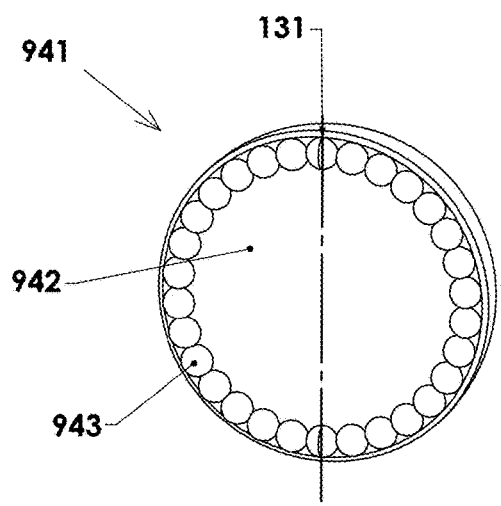
Figure 21F:
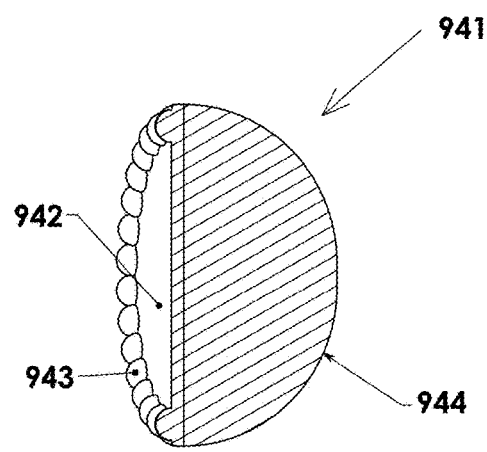

As illustrated by plate 941 of FIG. 21E, a plate can include a plurality of protrusions 943. As shown in FIG. 21E, the plurality of protrusions 943 can be arranged at the perimeter of the back surface 942. A front surface of plate 941, on the other side of the plate from back surface 942, forms dome-shaped, curved surface 944. As further illustrated in FIG. 21F, which is a section view of plate 941 of FIG. 21E, each protrusion 943 has a contact surface.

Figure 21G:
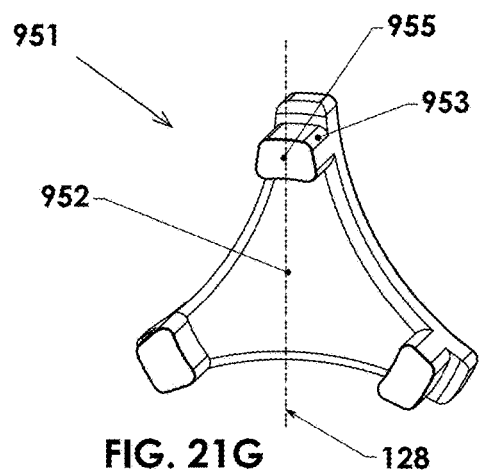

FIG. 21G is a perspective view of an example plate 951, including back surface 952 having protrusion 953 having contact surface 955.

Figure 21H:
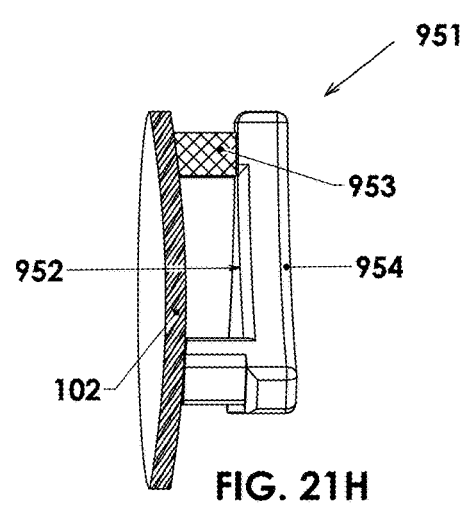

FIG. 21H is a left side section view of plate 951 of FIG. 21G, taken along line 128 in FIG. 21G, and a cutaway of sclera 102, showing contact between contact surface 955 of protrusion 953 and sclera 102. Plate 951 includes front surface 954, on the other side of the plate from back surface 952. When plate 951 is placed under an eyelid, contact surface 955 is in contact with sclera 102 and front surface 954 is in contact with the eyelid, not shown.

Figure 21I:
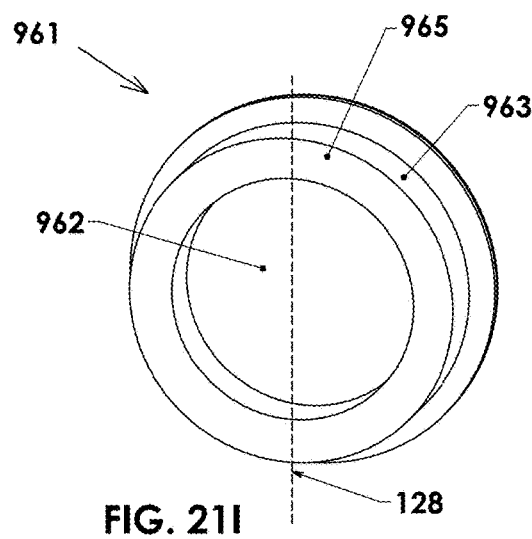

FIG. 21I is a perspective view of an example plate 961, including back surface 962 having protrusion 963 having contact surface 965.

Figure 21J:
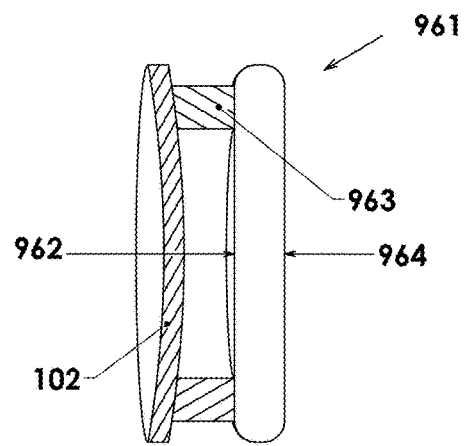

FIG. 21J is a left side section view of plate 961 of FIG. 21I taken along line 128 in FIG. 21I, and a cutaway of sclera 102, showing contact between contact surface 965 of protrusion 963 and sclera 102. The plate includes front surface 964, on the other side of the plate from back surface 962. When plate 961 is placed under an eyelid, contact surface 965 is in contact with sclera 102 and front surface 964 is in contact with the eyelid, not shown.

Figure 21K:
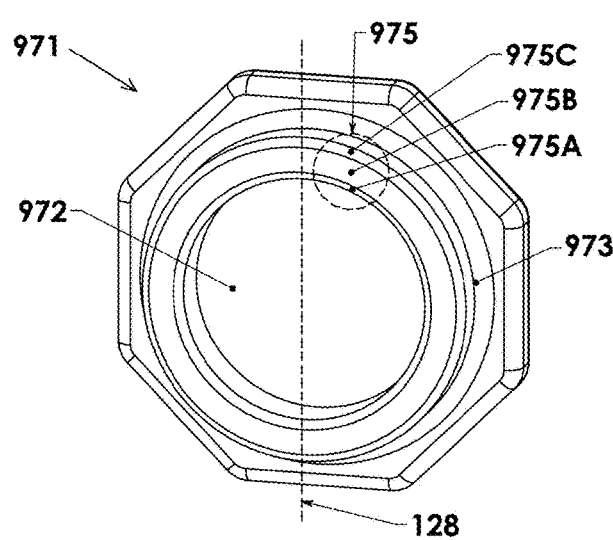

FIG. 21K is a perspective view of an example plate 971, including back surface 972 having protrusion 973 having contact surfaces 975, which is a combination of curved surface 975A, generally planar surface 975B, and curved surface 975C.

Figure 21L:
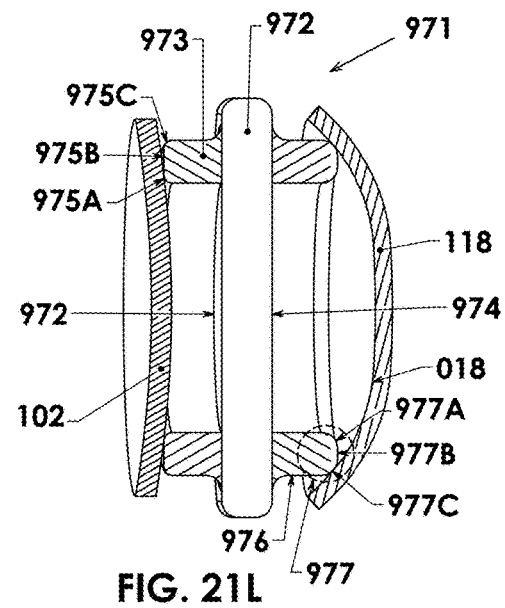

FIG. 21L is a left side section view of plate 971 of FIG. 21K taken along line 128 in FIG. 21K, and a cutaway of sclera 102. FIG. 21K shows contact between contact surface 975 and sclera 102. It should be appreciated that at any moment in time, any of 975A, 975B, and 975C of contact surface 975 could be in contact with sclera 102.

FIG. 21L further shows front surface 974, on the other side of the plate from back surface 972, front surface 974 having protrusion 976 having contact surface 977, which is a combination of 977A, 977B, and 978C. As shown in FIG. 21L, protrusion 977 is in contact with eyelid 118, which has eyelid drape 018. It should be understood, while not shown in FIG. 21K or 21L, that plate 971 could be placed under eyelid 118 with front surface 974 toward sclera 102, in which case contact surface 977 of protrusion 976 would be in contact with sclera 102. It should also be understood that plate 971, once placed under eyelid 118 with back surface 972 toward sclera 102, can rotate or move about so that front surface 974 is toward sclera 102. Thus, plate 971 with protrusions 973 and protrusions 976 can be under an eyelid with the back surface or the front surface toward sclera 102. This is the case whether plate 971 alone is placed under an eyelid as an ocular device, or plate 971 is part of an ocular device with other features, such as an elongated support member, and the ocular device of which plate 971 is a part is placed under an eyelid.

Figures and descriptions of plates and protrusions are provided as examples and not as limitations.

FIGS. 21A to 21L illustrate plates of varied shapes having protrusions arranged as shown. The plate shapes and protrusion arrangements are not limitations, and other shapes and arrangements are contemplated. As further examples, but not as limitations, FIGS. 22A-22E illustrate additional plate shapes and protrusion arrangements.

FIG. 22A is a frontal view of an adaptable non-directional ocular device 1000 without a central "arch" according to another example of an ocular device. Ocular device 1000 includes two combination elements 1011 and 1021 connected to elongated support member 1001. As demonstrated by the ocular device in FIG. 22A, an arch, shown in other ocular devices, need not be present. Ocular device 1000, which does not have an arch, can be inserted under an eyelid and deliver a drug to the eye. The ocular device shown in FIG. 22A illustrates an angular rotational extension of elongated support member 1001 to connect to plate 1021 with an angle 132 that is greater than 180 degrees, illustrating further flexibility of ocular devices disclosed herein.

FIGS. 22B-22E illustrate examples of convex, sclera-interacting features (e.g., protrusions) that may be used with embodiments of the invention. The protrusions provide convex contact surfaces to contact the sclera of the eye.

FIG. 22B illustrates plate 1011 of FIG. 22A, including a back surface 1030 with protrusions 1010 and 1013 having convex contact surfaces formed by two segments of a torus.

FIG. 22C illustrates an example plate 1021, including a back surface 1030 with protrusions 1013, 1023 having convex contact surfaces formed by two domes 1023 and a torus segment 1013.

FIG. 22D illustrates an example plate 1031, including a back surface 1030 with protrusions 1023, 1033, 1043 having convex contact surfaces formed by combinations of domes 1023 and torus sweep segments 1033, 1043.

FIG. 22E is a cross-section view of plate 1031 of FIG. 22D. The dome-shaped protrusions 1023 are shown in section. The front surface shown in FIG. 22E, which is on the opposite side of the plate from the back surface, can follow the plane curve 300, shown in FIG. 5B. An eyelid can drape on a surface of a plate that is shaped to follow the plane curve 300.

Figure 23A:
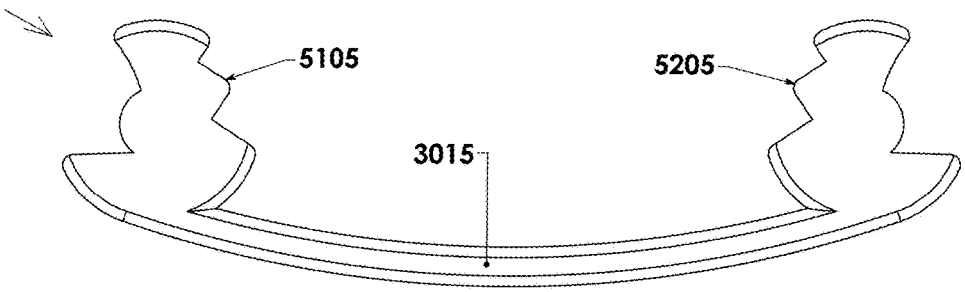
FIG. 23A is a front view of an example of an ocular device.
Figure 23B:
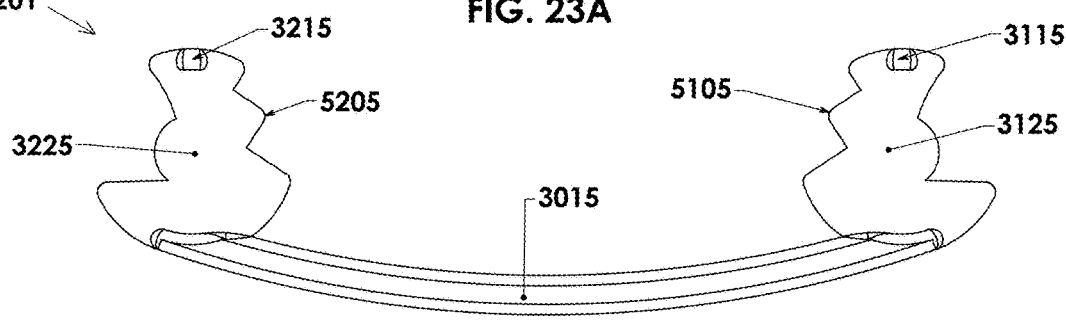
FIG. 23B is a back view of the ocular device of FIG. 23A.

FIG. 23A illustrates features of a front view and FIG. 23B illustrates features of a back view of ocular device 1201 for placement under an eyelid, provided to illustrate aspects of disclosed ocular devices. As shown in FIG. 23A, ocular device 1201 comprises an elongated support member 3015 of flexible material configured to be positioned under an eyelid of an eye (not shown), and a plate 5105, 5205 connected proximate to each end of the support member 3015 and substantially coplanar with the support member. As shown in FIG. 23B, each plate 5105, 5205 comprises a back surface 3125, 3225, the back surface having at least one protrusion 3115, 3215 having a convex contact surface to contact the sclera of the eye and to provide an offset space between the sclera and the back surface 3125, 3225 of the plate 5105, 5205.

Figure 23C:
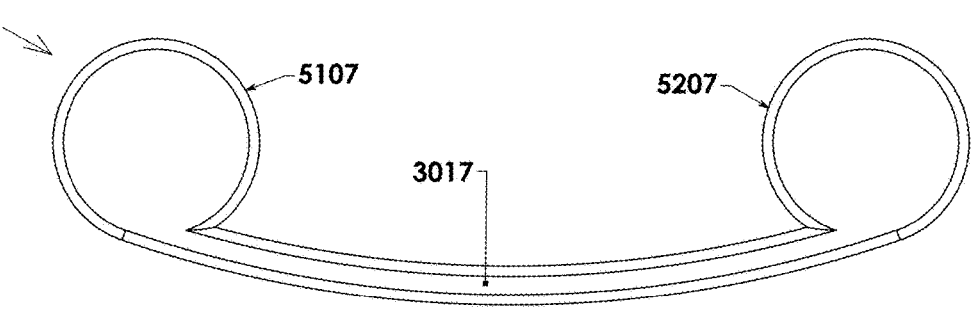
FIG. 23C is a front view of an example of an ocular device.
Figure 23D:
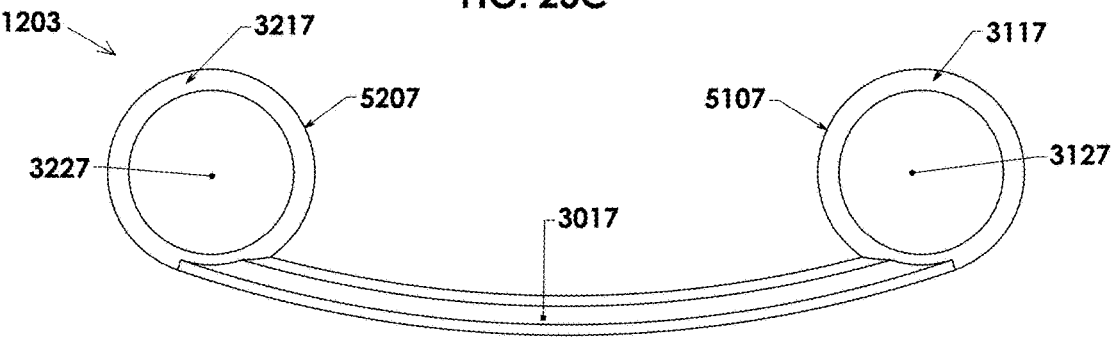
FIG. 23D is a back view of the ocular device of FIG. 23C.

FIG. 23C is a front view and FIG. 23D is a back view of ocular device 1203 for placement under an eyelid, provided to illustrate aspects of a disclosed ocular device. As shown in FIG. 23C, ocular device 1203 comprises an elongated support member 3017 of flexible material configured to be positioned under an eyelid of an eye (not shown) and a plate 5107, 5207 connected proximate to each end of elongated support member 3017 and substantially coplanar with the support member. As shown in FIG. 23D, each plate 5107, 5207 comprises a back surface 3127, 3227, the back surface having at least one protrusion 3117, 3217 having a convex contact surface to contact the sclera of the eye and to provide an offset space between the sclera and the back surface 3127, 3227 of the plate 5107, 5207, wherein at least one protrusion 3117, 3217 is toroidal.

Figure 23E:
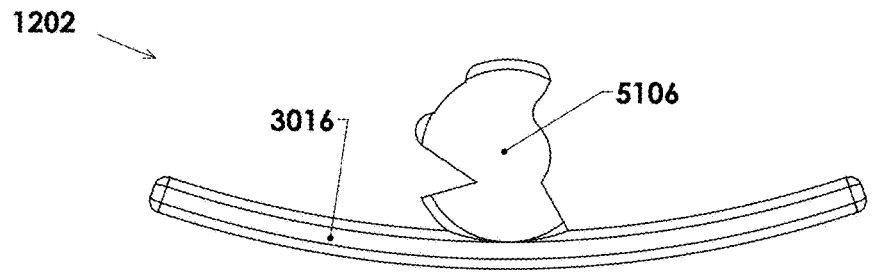
FIG. 23E is a front view of an example of an ocular device.
Figure 23F:
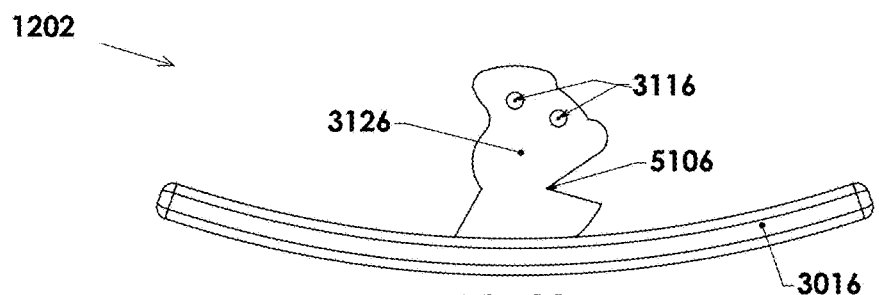
FIG. 23F is a back view of the ocular device of FIG. 23F.

FIG. 23E is a front view and FIG. 23F is the back view of ocular device 1202 for placement under an eyelid, provided as a further example of an ocular device. As shown in FIG. 23E, ocular device 1202 comprises an elongated support member 3016 of flexible material configured to be positioned under an eyelid of an eye, at least one plate 5106, connected to the support member 3016. As shown in FIG. 23F, plate 5106 comprises a back surface 3126, the back surface 3126 having at least one protrusion 3116 having a convex contact surface to contact the sclera of the eye and to provide an offset space between the sclera and back surface 3126 of plate 5106.

Figure 23G:
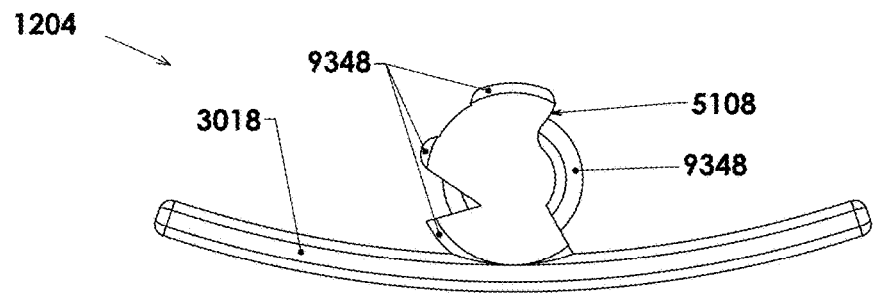
FIG. 23G is a front view of an example of an ocular device.
Figure 23I:
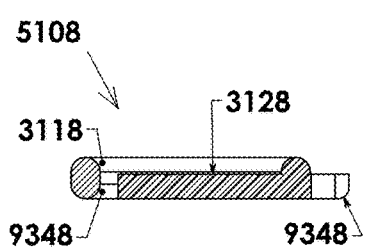
FIG. 23I is a cross section along A-A of the ocular device in FIG. 23H.
Figure 23H:
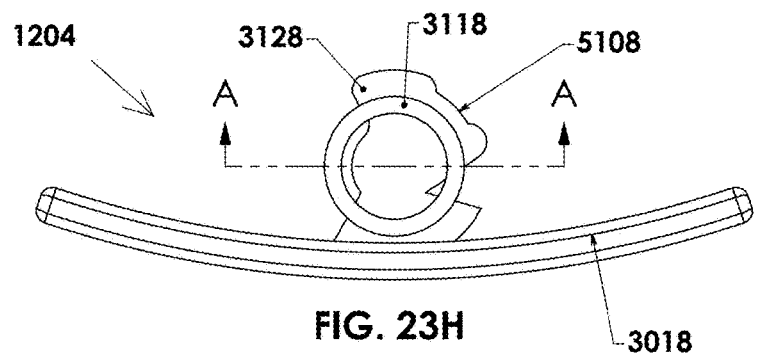
FIG. 23H is a back view of the ocular device of FIG. 23G.

FIG. 23G is a front view and FIG. 23H is a back view of ocular device 1204. FIG. 23I is a cross section of FIG. 23H, illustrating plate front convex protrusion surface 9348 (also seen in FIG. 23G). Protrusion 9348 is a further example of a convex front surface discussed above with respect to the example in FIG. 21F, a section view of FIG. 21E. As discussed, FIG. 21F provides an illustration of a front surface of a plate example with back surface 942, protrusions 943 projecting from back surface 942, and a front surface of convex shape 944. FIG. 23I is a section view along A to A of plate 5108 of ocular device 1204 in FIG. 23H, provided to illustrate a further example of a disclosed ocular device.

As shown in FIG. 23G, ocular device 1204 comprises an ocular device for placement under an eyelid, the ocular device comprising an elongated support member 3108 of flexible material configured to be positioned under an eyelid of an eye; and at least one plate 5108 connected to the support member 3108. As shown in FIG. 23H plate 5108 comprises back surface 3128 having at least one protrusion 3118, protrusion 3118 having a convex contact surface to contact the sclera of the eye and to provide an offset space between the sclera and back surface 3128 of plate 5108. Protrusion 3118 of ocular device 1204 is toroidal. As can be seen in FIG. 23G, protrusion 3118 has a surface 9348 on the front of plate 5108, and surface 9348 can contact the eyelid when ocular device 1204 is in an eye.

Further referring to FIG. 23G and FIG. 23I, a section view of FIG. 23H back protrusion toroidal sclera convex contact surface 3118 of FIG. 23H includes a front convex protrusion lid contact surface 9348 (also seen in FIG. 23G), which is a toroidal protrusion projecting towards front side of 1204 where the lid resides.

Plate 5108 is not constrained by the 3118, 9348 protrusion geometry perimeter, and back surface 3128 of plate 5108 does not fully occlude the 3118 back and 9348 front protrusion geometry features, resulting in a no material area, also referred to herein as open space, bound back and front by the sclera and the eyelid respectively, residing within the combined greatest perimeter of plate 5108 and back facing protrusion geometry 3118. The back surface 3128 of plate 5108 and the eyelid inner surface proximate to the no material area(s) can each be defined as remote surfaces to the sclera surface and protrusion 3118. Tear volume engaging the device as a result is substantial in comparison to other under the eyelid devices in the art.

Surface 3128 is at a different sclera offset height than the eyelid as defined by protrusion 3118. The eyelid is the most remote surface from the sclera.

Figure 24A:
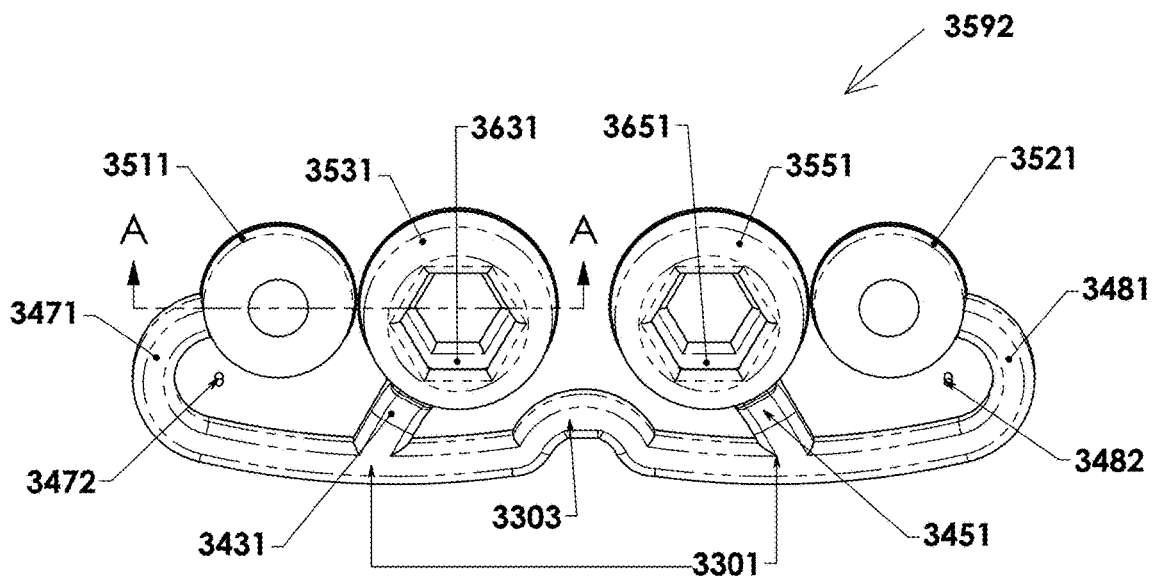
FIG. 24A is a front view of an ocular device.
Figure 24B:
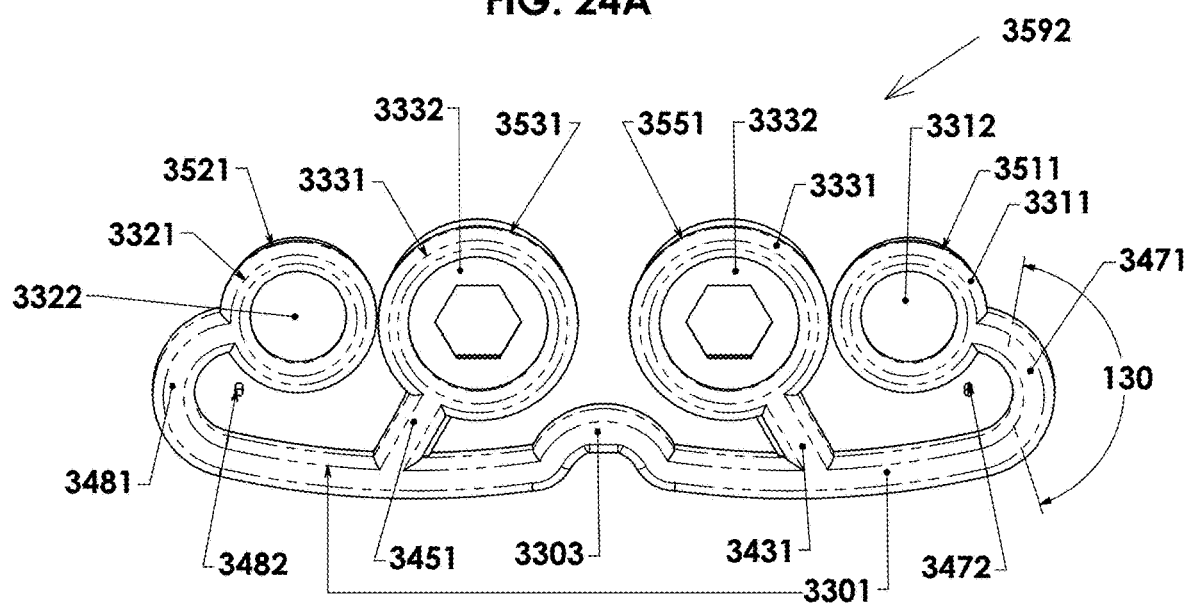
FIG. 24B is a back view of the ocular device of FIG. 24A.
Figure 24C:
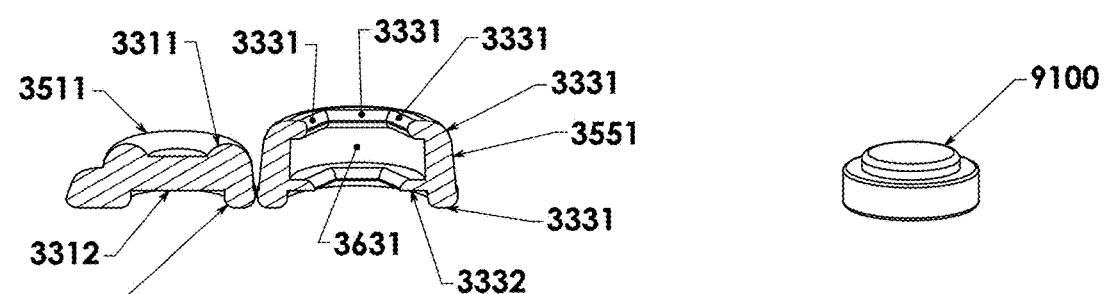
FIG. 24C is a section view along line A-A of the ocular device of FIG. 24A.

FIGS. 24A, 24B, and 24C illustrate ocular device 3592. FIG. 24A is a front view of ocular device 3592, FIG. 24B is a back view of ocular device 3592, and FIG. 24C is a section view along line A-A of the ocular device of FIG. 24A.

To facilitate orientation of ocular device 3592 in an eye with the back surface or the front surface of the plates toward the sclera, plates 3511 and 3521 have protrusions 3311 on both the back surface and the front surface, and plates 3531 and 3551 have protrusions 3331 on both the back surface and the front surface.

As can be seen in FIGS. 24A and 24C, plates 3531 and 3551 have pockets 3631 and 3651, which are open on both the front and the back surface. Ocular device 3592 illustrates the possibility that an ocular device can be made with polygonal, such as hexagonal, holes or openings to the pockets of the plates, and the openings can be of different sizes. As can be seen in FIG. 24C, an insert can be retained in a plate by retaining lip 3332.

Figure 24D:
FIG. 24D is an isometric view of an example of an insert (or drug insert) that can be placed into an ocular device, including the ocular device shown in FIGS. 24A to 24C.

FIG. 24D is an isometric view of an example of a drug insert, or insert, that can be inserted in an ocular device, including the ocular device shown in FIGS. 24A to 24C. It should be understood that a round insert 9100 is shown as an example to illustrate that the insert with that shape can be inserted into a hexagonal opening to pocket 3631 or 3651, with points of contact between the round insert and the hexagonal opening to the pocket. An insert of any shape that can be made and inserted in a pocket of a plate of an ocular device.

An ocular device can be inserted into the eye by the user. The user may employ a mechanism to store and deliver the device for insertion into the eye. The ocular device may be used with or without such a mechanism, and the ocular device is not limited to use with such a mechanism.

Case

Disclosed in this application is a case that can be used as a mechanism to store and deliver an ocular device for insertion into an eye. The case enables the user to remove an ocular device as delivered by the case, for grasping and ease of insertion in an eye. Described is a case for holding and dispensing an ocular device to be inserted and removed for insertion in the eye of a user, usually with a person's fingers. The person can be the user or another person, such as a doctor, other eye care professional, or a caregiver. The case presents the ocular device to be grasped by fingers with the ocular device oriented in the proper 3-dimensional orientation relative to the user, for placement in the eye of the user. The case and its components may have tactile features to allow one who is visually impaired to determine or confirm the orientation of the ocular device for placement in the eye, remove the ocular device from the case, and insert the ocular device knowing its orientation.

The case may provide a port for introducing a fluid to coat an ocular device in the case. Gas, including air, may also pass through the port. The fluid can be introduced without manipulating features of the case or an ocular device in the case.

The case can dispense an ocular device from either of two sides of the case, maintaining the orientation of the ocular device. For example, the case can have a receiver with a channel that is open on two sides of the receiver, the channel configured to enable the ocular device to be dispensed from either of the two sides of the receiver, without changing the orientation of the ocular device. As a result, the ocular device may be removed from the device using fingers of a left hand or of a right hand, without the need to reorient the case or to reposition the ocular device once removed from the case.

The case may be composed of a thermoplastic material, for example polypropylene thermoplastic material.

Figure 25A:
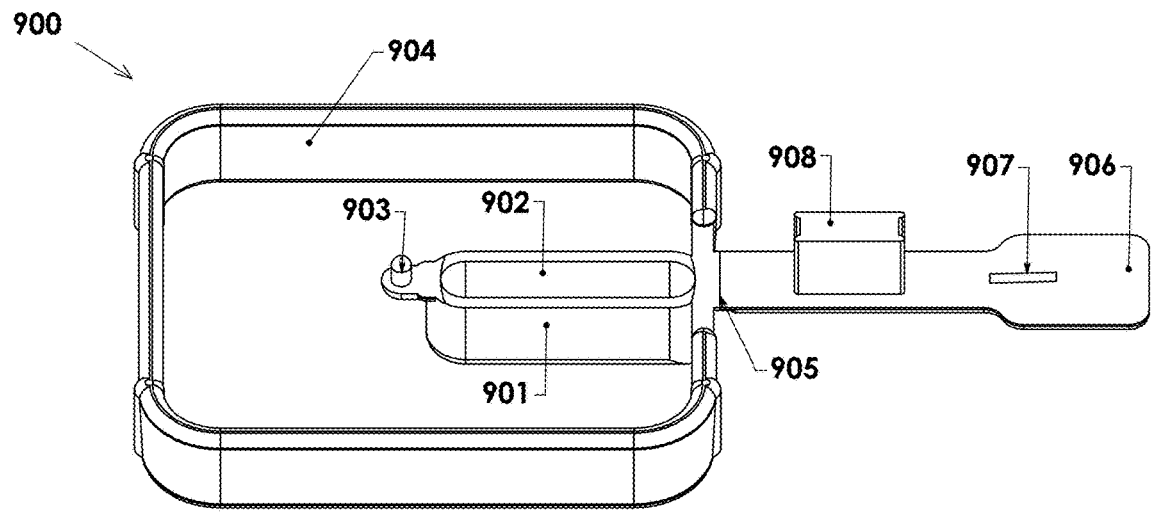
FIG. 25A is a perspective view of an open case.

FIG. 25A is a perspective view of case 900, which is in the open position. Case 900 includes well 901. Well 901 is configured to retain fluid within the interior of the well, which is shown in FIG. 25A as interior space 902. Well 901 is shown in FIG. 25A with an elongated oval shape. It should be appreciated that a well can be in a different shape from the shape shown in FIG. 25A, the shape depending on the shape of the ocular device to be held, the needs of the user, and the desired shape of the case 900. As shown in FIG. 25A, well 901 has an open top.

The case may be formed as a single piece of material. The case may be made from thermoplastic or thermoset polymers that demonstrate an ASTM D638 ISO 527-1 Tensile Test Method Elongation Percentage (%) at Yield in a range of about 6% to 250%. Features of the case may be interconnected. Each feature of the case can perform different functions. As an example and not as a limitation, one or more features of the case or the entire case may be made from polypropylene thermoplastic material.

The case may be manufactured using a relatively low cost injection molding process.

Well 901 is connected to stabilizer 904 at junction 905. Well 901 may be connected perpendicular to a side of stabilizer 904 at junction 905. The connection between well 901 and the side of stabilizer 904 at junction 905 may be achieved in many ways and is not limited to the connection shown in FIG. 25A. As shown in FIG. 25A, stabilizer 904 forms a ring that surrounds well 901, and well 901 protrudes into the interior of the ring so that well 901 is surrounded and protected by stabilizer 904.

Stabilizer 904 provides a location to grip case 900. When dispensing an ocular device, the case can be secured to a substantially flat location, for example by placing a hand or portion of a hand or finger(s) on stabilizer 904. Stabilizer 904 can stabilize case 900 on a substantially flat location, for example by preventing the case from tipping over. Stabilizer 904 may include features that visually, tactilely, or otherwise indicate an orientation of the case relative to a user of an ocular device to be dispensed from the case. For example, the stabilizer can be labeled with words, braille, or color, alone or in combination, communicating the message "place toward user."

Case 900 includes lid 906. Lid 906 is connected to well 901 and rotatable between a position covering the open top of the well so that the case is closed and a position with the well uncovered so that the case is open. The connection between lid 906 and well 901 may be a hinge. The hinge may be a living hinge where the material connecting well 901 and lid 906 is a single manufactured part that can flex back and forth. It should be understood that lid 906 and well 901 of the case may be connected directly or with intervening material, including for example a portion of the stabilizer 904.

As shown in FIG. 25A, lid 906 is a planar lid with a top and bottom. A lid for use in a case for an ocular device may be comprised of any combination of geometric shapes, provided that the lid can cover the top of a well when the lid is in the position covering the open top of the well. As depicted in FIG. 25A, lid 906 is generally comprised of two planar rectangles, which are of different dimensions to allow for easier identification and manipulation. The elongated planar rectangle, proximate to junction 905, is capable of covering the open top of well 901. When in the position covering the top of the well (see FIG. 25B), the planar rectangle distal to junction 905 extends past well 901, permitting a user to use the remote planar rectangle to remove lid 906 from the top of well 901 and rotate the lid around junction 905.

The case can further include a fastener for removably securing lid 906 in a position covering the open top of well 901. The fastener can, for example, be a latch or lock. As shown in FIG. 25A, the case includes latch 907/903 comprising key 907 on the lid and post 903 on a protrusion extending from well 903. Key 907 is depicted in FIG. 25A as a gap in lid 906. Key 907 may be formed in a shape that permits engagement with post 903 to removably secure lid 906 in a position covering the open top of well 901. As shown in FIG. 25A, post 903 is located on a protrusion from well 901 on the opposite end of the well from junction 905. Post 903 extends from the protrusion extending from well 901, perpendicular to the protrusion. Post 903 may be cylindrical. It should be understood that the fastener may be a latch, anchor, or other device that removably secures the lid to the well. The fastener may also be friction fit of the lid with the well, or features on the lid or the well or both. It should be further understood that components of the fastener may be any part of the case or added to any part of the case.

The case can further include a feature for holding and dispensing an ocular device. As shown in FIG. 25A, the case has a receiver 908, which projects from lid 906 and is configured to receive and hold an ocular device. Receiver 908 is positioned so that when lid 906 is in the closed position, receiver 908 is within interior space 902 of well 901 so that any fluid in the well, such as fluid transmitted through port 909, contacts the ocular device held in receiver 908 and the ocular device can be submerged in the fluid. Receiver 908 can be proximate to port 909 so that, when the lid is in the closed position, fluid entering port 909 flows past the ocular device. There is a channel through receiver 908, open on both sides of the receiver. The channel can hold an ocular device and is configured to enable the ocular device to be dispensed from either of the two sides of the receiver, without changing the orientation of the ocular device. As a result, the ocular device may be removed from the case using fingers of a hand to pull the ocular device from the receiver, without the need to reorient the case or to reposition the ocular device once removed from the case. As an option, on removing the ocular device with a pulling hand a pushing hand may be used to direct the ocular device toward the pulling hand.

The channel in receiver 908 may be of any three-dimensional shape that can receive an ocular device. One side of the channel is defined by the top surface of lid 906, and three sides are defined by the receiver. The channel is shown in FIG. 25A as open on two ends.

Figure 25B:
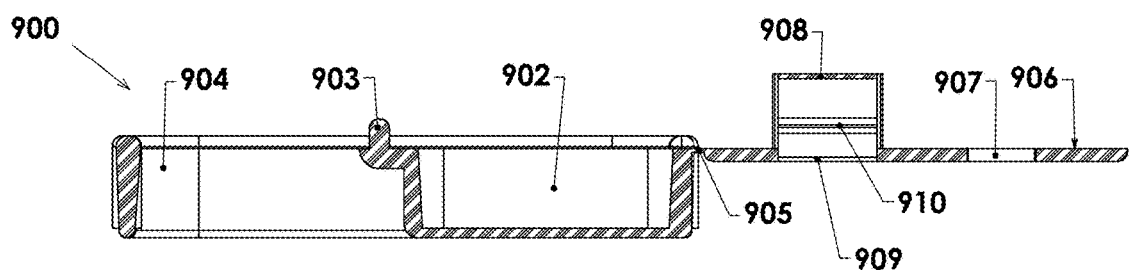
FIG. 25B is a side view cross-sectional view of the open case shown in FIG. 25A.

FIG. 25B is a side view of the case 900 shown in FIG. 25A, cut longitudinally through the center of the case. Lid 906 is in a position covering the open top of the well, so that the case is closed. Ridge 910, which can be seen in the cut open receiver in FIG. 25B, is a restraining element, configured to hold an ocular device. It should be understood that the restraining element may be a ridge or other element configured to hold an ocular device in a specific orientation or position and to allow the insertion and removal of the ocular device. It should be understood that receiver 908 may be any geometric shape that permits it to receive, hold, and dispense an ocular device.

Figure 25C:
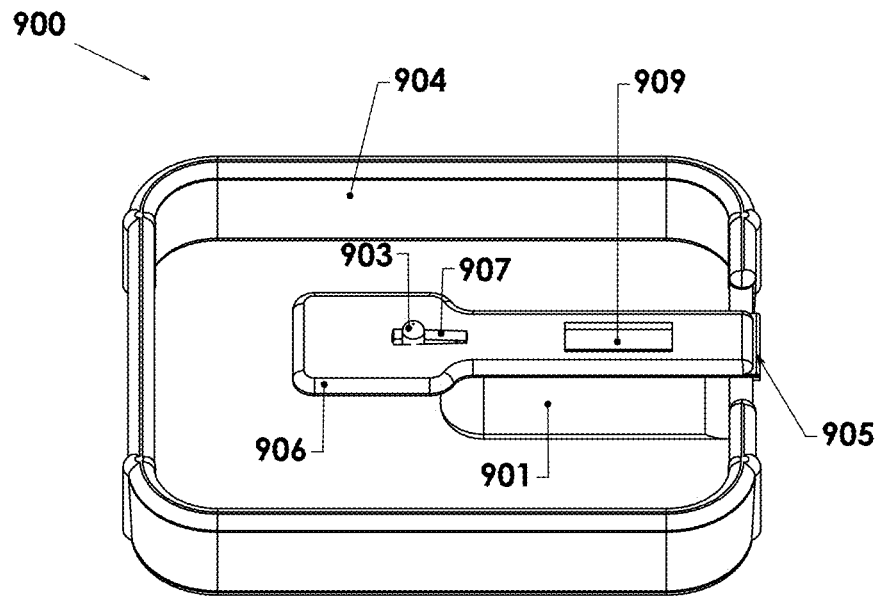
FIG. 25C is a perspective view of the case shown in FIG. 25A, with the lid in the closed position.

FIG. 25C is a perspective view of the case shown in FIG. 25A, with the lid in the closed position. As shown in FIG. 25C, post 903 is engaged with key 907, removably securing lid 906 in the closed position, preventing liquid from entering or exiting interior space 902 during manipulation of case 900, except through port 909. The latch can be a post and key of any shape provided that, when lid 906 is in the closed position, friction between post 903 and key 907 removably secures lid 906 in the closed position. The lid and well may include additional features to form a seal between the lid and the well.

Lid 901 is depicted in FIG. 25B with port 909. Port 909 is a gap in lid 906. When lid 906 is in the closed position, port 909 is in fluid communication with interior space 902 of well 901, permitting fluid, including liquid such as a solution, and gas, such as air, to enter or exit interior space 902 of well 901 through port 909. As an example, port 909 allows for solution to be added to the interior space 902 of well 901 of case 900 without the need to remove lid 906 from well 901 to expose interior space 902 or any device held in case 900. Port 909 can be of a length that is sufficient for the escape of gas, such as air, from and the entry of liquid into the interior space 902 of well 901. Liquid and gas can be exchanged through port 909 simultaneously.

Figure 25D:
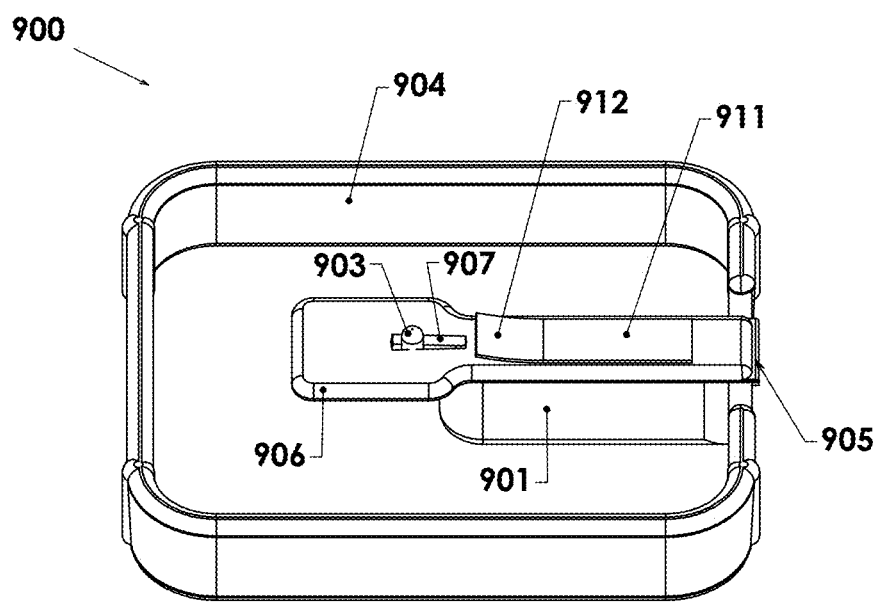
FIG. 25D is a perspective view of the case shown in FIG. 25C, a peel strip covering the port in the lid.

FIG. 25D is a perspective view of the case shown in FIG. 25C, with removable peel strip 911 covering the port in the lid. The peel strip seals port 909 of well 901. In FIG. 25D, a portion of the peel strip 911, labelled 912 in FIG. 25D, projects away from the lid surface to enable removal of the peel strip to reveal the port. The peel strip can be made from materials that provide a biological barrier for sterilization of the chamber. A sealed chamber is formed within well 901 in interior space 902 when the lid is in the closed position and the peel strip is in place. It should be understood that any method can be used for sterilization of the sealed chamber, including, but not limited to, gamma radiation, electron beam, steam, autoclave, and ethylene oxide (ETO). When the peel strip is removed and the lid is in the closed position, fluid can be added to the case through the port and, with an ocular device inside, fluid will flow past the ocular device.

Case 900 may include removable peel strip 911 covering port 909. Removable peel strip 909 protects interior space 902 and the content of receiver 910 from contamination and disruption. When a user needs to access port 909, removable peel strip 911 can be peeled off lid 906. Removable peel strip 911 may include tab 912 disconnected from lid 906. Tab 912 provides enables removal of peel strip 911 by grasping and removing peel strip 911. In addition to protecting interior space 902, the peel strip resists tampering and provides an alert to tampering that may have occurred. Other tamper resistant devices and alerts, such has a breakaway tape, can be adapted to the case.

An ocular device can be sterilized in the sealed chamber. It should be understood that any method can be used for sterilization of the ocular device in the sealed chamber, including, but not limited to, gamma radiation, electron beam, steam, autoclave, and ethylene oxide (ETO).

Figure 26A:
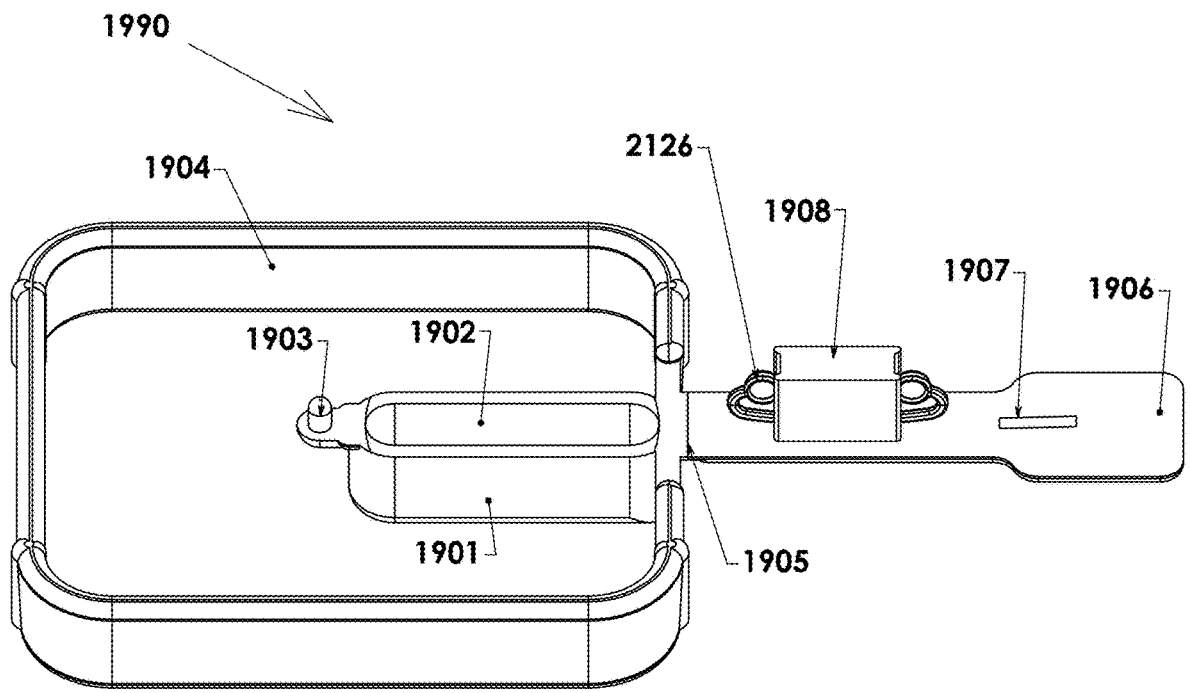
FIG. 26A is a perspective view of an open case holding an example of an ocular device.

FIG. 26A is a perspective view of case 1990 with lid 1906 in the open position, holding an example of an ocular device, labelled as 2126. It should be understood that case 1990 is not limited to use with the particular ocular device 2126 shown in FIG. 26A. A receiver may comprise a channel that is open on at least one side of the receiver. As shown in FIG. 26A, the channel in receiver 1908 is open on two sides of the receiver.

Figure 26B:
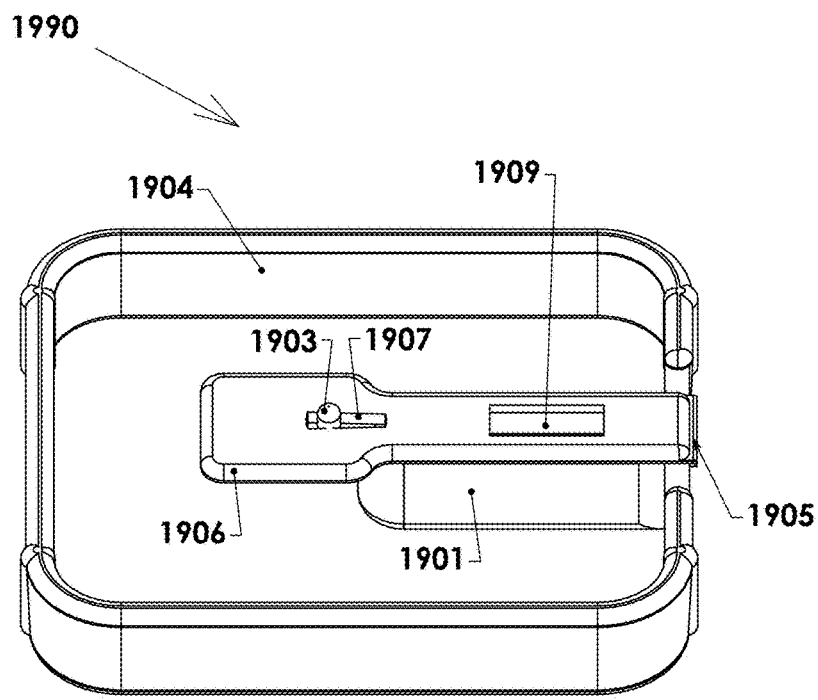
FIG. 26B is a perspective view of a closed case holding an example of an ocular device (not shown).

FIG. 26B is a perspective view of a closed case holding an example of an ocular device (not shown), with port 1909 uncovered for the introduction of fluid into the well past the ocular device.

Figure 26C:
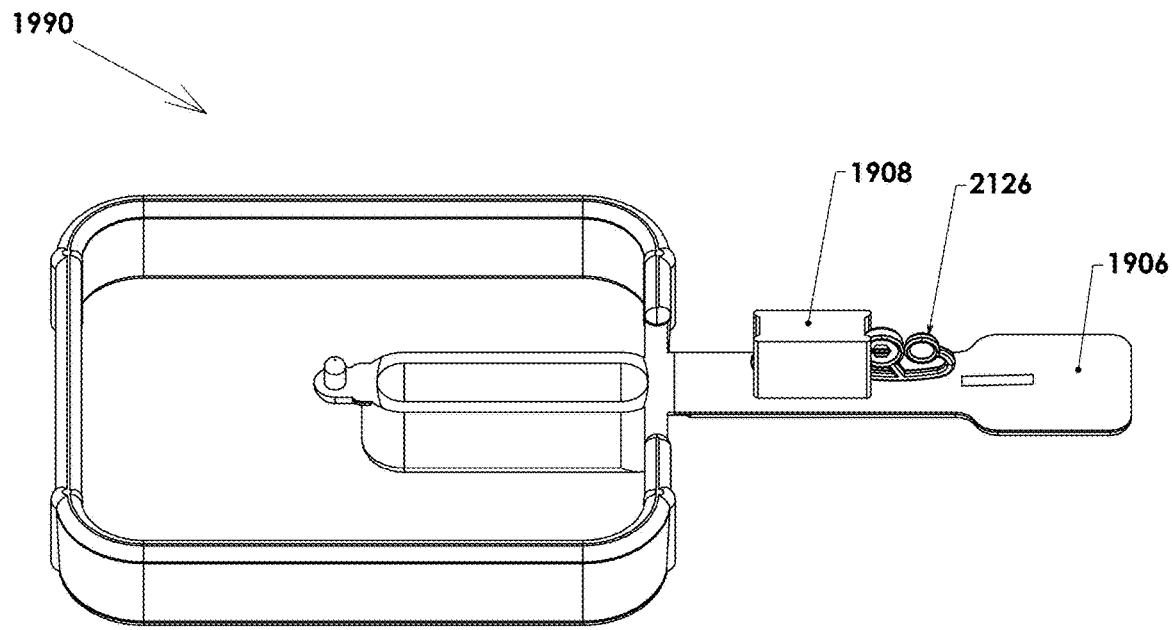
FIG. 26C is a perspective view of an open case holding an example of an ocular device protruding from a side of the receiver distal to a well.

FIG. 26C is a perspective view of an open case holding an example of an ocular device protruding from a side of the receiver distal to a well.

Figure 26D:
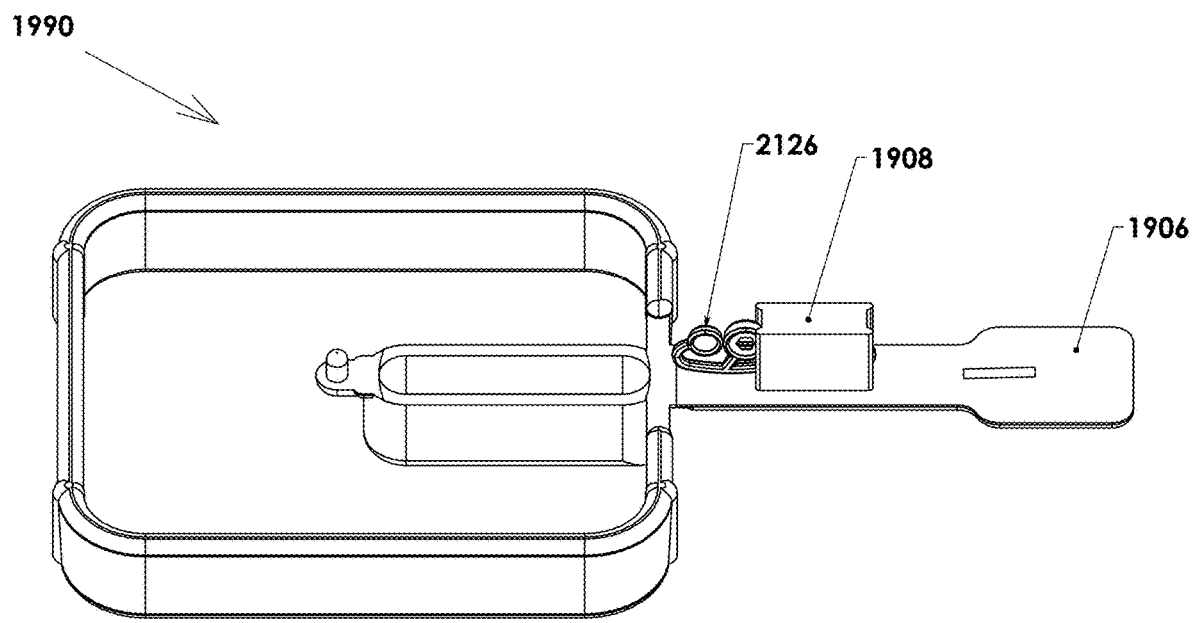
FIG. 26D is a perspective view of an open case holding an example of an ocular device protruding from the receiver proximate to a well.

FIG. 26D is a perspective view of an open case holding an example of an ocular device protruding from the receiver proximate to a well.

FIG. 26A is a schematic illustrating an example embodiment of a case 1990 in the open position holding an example embodiment of an ocular device 2126 and FIG. 26B is a schematic illustrating an example embodiment of a case 1990 in the closed position holding an example embodiment of an ocular device 2126. Case 1990 is positioned on a substantially flat location in front of the user with the surface of the ocular device 2126 to be in contact with the sclera of the eye toward the user. An embodiment of the invention allows case 1990 to have ocular device 2126 held by receiver 1908 within interior space 1902 when lid 1906 is the closed position covering well 1901, as shown in FIG. 26B. Post 1903 and key 1907 may be interconnected to secure lid 1906 in the closed position. Case 1990 can be delivered to a user in the closed position shown in FIG. 26B with ocular device 2126 protected and held at the desired orientation. When case 1990 is received by a user, case 1990 is configured to allow the user to orient ocular device 2126 in the specific orientation and/or position that facilitates proper the insertion of ocular device 2126.

A user can rotate lid 1906 from the position covering the open top of the well to the open position shown in FIG. 26A. When lid 1906 is in the open position, receiver 1908 delivers ocular device 2126 for insertion in an eye. It should be appreciated that ocular device 2126 may require a particular orientation for correct ocular insertion, or a particular orientation may be preferred. Receiver 1908 can be configured to hold and present ocular device 2126 in a specific orientation. When case 1903 is placed on a table or other substantially flat surface, the orientation of ocular device 2126 is determined by the orientation of case 1990. As a result, controlling the orientation of case 1990 determines and controls the orientation of ocular device 2126. Case 1990 can be oriented relative to a user so that ocular device 2126 is oriented correctly for insertion in the eye of the user. With the case oriented correctly relative to the user, lid 1906 is rotated to the open position to deliver ocular device 2126, ocular device 2126 is removed from receiver 1908, and the ocular device is inserted into the eye of the user, maintaining the orientation of the ocular device relative to the user.

FIG. 26C is a schematic illustrating an example embodiment of a case 1990 in the open position holding an example embodiment of an ocular device 2126 protruding from the receiver 1908 at the side of the receiver distal to the well and FIG. 26D is a schematic illustrating an example embodiment of a case 1990 in the open position holding an example embodiment of an ocular device 2126 protruding from the receiver 1908 at the side of the received proximate to the well. Ocular device 2126 may be removed from receiver 1908 through either open side of receiver 1908 as shown in FIGS. 26C and 26D. A user may use a pulling hand to grasp the protruding portion of ocular device 2126 from either the proximate or the distal side. A user may also use a pushing hand to direct the protruding portion of the ocular device 2126 toward the pulling hand. Because ocular device 2126 can be inserted or removed through either open side of receiver 1908, case 1990 can be held at multiple angles and the ocular device can be accessed by either hand of the user. This allows the user to choose their preferred hand and grip when performing the delicate task of manipulating and/or inserting ocular device 2126.

Case 1990 can include tactile and visual features to enable a user to identify the orientation of ocular device 2126, without opening lid 1096 of case 1990 and exposing ocular device 2126. Case 1990 can be larger than ocular device 2126, so that the orientation can be apparent, even if the orientation of the ocular device itself is not apparent. The orientation of case 1990 can be used to determine the orientation of ocular device 2126, instead of examining ocular device 2126 directly, reducing the risk of misidentifying the orientation and the risk of misplacement of the device due to an orientation error. The positioning of the case, stabilizer 1904, lid 1906, and/or receiver 1908 visually, tactilely, or otherwise indicates the proper orientation of ocular device 2126 to the user.

Delivery of ocular device 2126 from opposite sides of the receiver as shown in FIG. 26C and in FIG. 26D enables removal of the device from either side of the case with either hand pulling the device from the case. The device can be pushed into the position shown in FIG. 26C or in FIG. 26D, optionally using the other hand from the one used to pull the device.

Figure 27A:
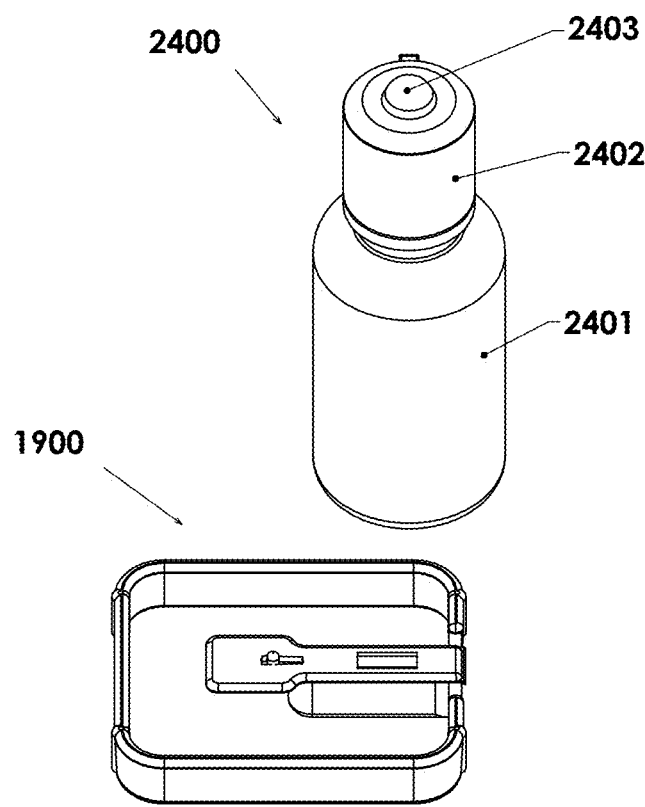
FIG. 27A is a schematic illustrating an example of a kit that includes a case holding an ocular device (not shown) and solution.

FIG. 27A is a schematic illustrating an example embodiment of a kit that includes a case 1990 holding an ocular device (not shown), and material to administer to the eye of a user. The kit includes case 1990, material to administer to the eye of a user contained in bottle 2400, and an ocular device. The material to administer to the eye can be, for example, wetting solution, medicine, drugs, or pharmaceuticals. The kit may be combined with a sterile pouch (not shown) configured to hold and protect case 1990. The sterile pouch may be composed of a plastic cover attached to a biological barrier bottom film composition with a seal along all edges of the plastic cover. This perimeter seal can ensure that case 1990, and any contents in the case, remain within the pouch during delivery and act as proof that sterilization of case 1990 has been maintained. The pouch seal may be configured so that a user may tear at least one edge open to expose the case. As an example, a commercially available Tyvek pouch may be used. The kit may also include a sealed case 1990 (see FIG. 25D) with a biological barrier such as a peel strip sealing the port, material to administer to the eye of a user in bottle 2400, and an ocular device in the sealed case. The material to administer to the eye can be, for example, wetting solution, medicine, drugs, or pharmaceuticals, or a combination of these materials.

Figure 27B:
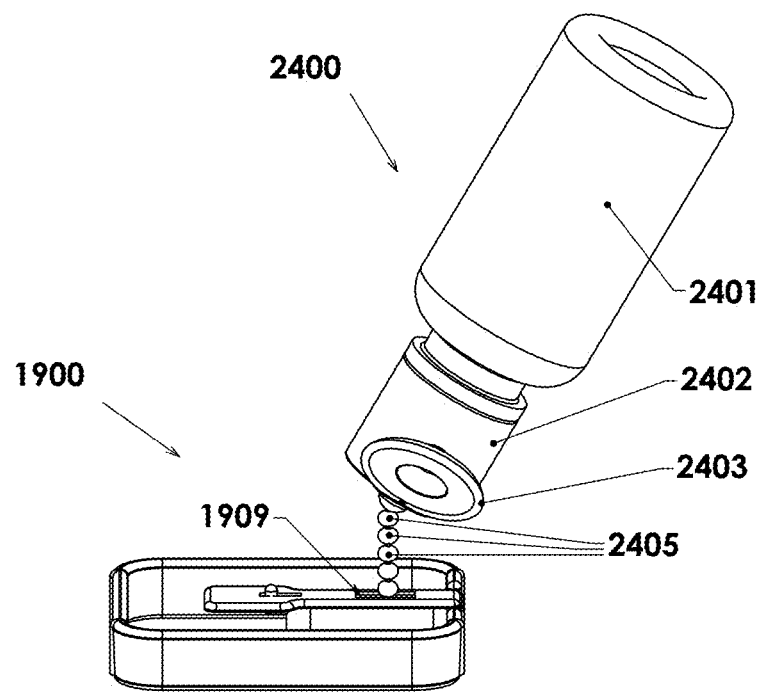
FIG. 27B is a schematic illustrating an example of a kit with the solution being applied to an ocular device (not shown) in a case.

FIG. 27B is a schematic illustrating an example embodiment of a kit where material being applied to an ocular device in a case. In this particular example, the user pours liquid 2405 through port 1909. During this process, case 1990 remains in the closed position and the ocular device within remains covered, with the port in fluid communication with the inside of the well. The ocular device in case 1990 is submerged in liquid 2405 as it flows through port 1909 and fills the well of case 1990. Air escaping the well case 1990 can also flow through port 1909. The ocular device in case 1990 is coated in liquid 2405.

Terms such as "convex" and "torus" and "sphere" are communication tools to describe attributes and interactions of disclosing devices and ocular anatomy and to inform as to relationships of the surface interactions and are not meant to be limitations to precise geometric forms of ocular devices disclosed.

Pockets and drug inserts that appear in figures are meant to illustrate possible features for simplification of description and are not intended to be in any way limiting.

It should be understood that terminology that describes geometric shapes and relationships are not to be considered as mathematically describing any device or feature with mathematical precision.

Insert Compositions and Methods of Manufacture

Any number of inserts may be placed into an ocular device described herein, particularly when fabricated of a geometry to permit placement in the ocular device. Typically, an insert comprises one or more pharmaceutically active agents, and a pharmaceutically acceptable carrier. Using more than one pharmaceutically active agents can provide, for example, release of pharmaceutically active agents that can treat more than one eye condition simultaneously.

Accordingly, provided herein is a composition (e.g., a pharmaceutical, such as an ocular, composition or insert composition) comprising one or more pharmaceutically active agents, and a pharmaceutically acceptable carrier (e.g., an ocularly compatible carrier). In some embodiments, the pharmaceutically acceptable carrier forms a matrix, and the one or more pharmaceutically active agents is dispersed (e.g., uniformly dispersed) within the matrix. In some embodiments, the matrix includes one or more polymers (e.g., a blend of two or more polymers, such as a water-soluble polymer, and a water-insoluble polymer). Pharmaceutically active agents, e.g., for use in inserts in ocular devices, can be of a variety of compositions, structures, and properties and include, but are not limited to, ciprofloxacin, dexamethasone, olopatadine, pilocarpine, hyaluronic acid and hydroxypropyl cellulose, as well as their pharmaceutically acceptable salts. Pharmaceutically active agents can include agents needed for short-term, long-term or both short- and long-term treatment of the eye. Examples of conditions of the eye that may be beneficially treated using the devices and compositions described herein include dry eye, glaucoma, allergies, infection (e.g., bacterial, viral and other infection), chronic inflammatory conditions such as acne rosacea keratitis, cyclitis, and blepharitis, selected retinal conditions such as diabetic retinopathy, age related macular degeneration and other retinal conditions, post-surgery, amblyopia.

Classes of pharmaceutically active agents useful in the treatment of the above-mentioned conditions include steroids, anti-inflammatories, antibiotics, glaucoma treatment compounds, antihistamines, dry eye medication, neuroprotectives, retinoids, antineovasculars, antioxidants, antimuscarinic drugs and biologics. Examples of steroids include glucocorticoids, aprogestins, amineralocorticoids, and corticosteroids. Exemplary corticosteroids include cortisone, hydrocortisone, prednisone, prednisolone, methylprednisone, triamcinolone, fluoromethalone, dexamethasone, medrysone, betamethasone, loteprednol, fluocinolone, flumethasone, rimexolone and mometasone. Other examples of steroids include androgens, such as testosterone, methyltestosterone, or danazol. Examples of anti-inflammatories include NSAIDs such as piroxicam, aspirin, salsalate (Amigesic), diflunisal (Dolobid), ibuprofen (Motrin), ketoprofen (Orudis), nabumetone (Relafen), piroxicam (Feldene), naproxen (Aleve, Naprosyn), diclofenac (Voltaren), indomethacin (Indocin), sulindac (Clinoril), tolmetin (Tolectin), etodolac (Lodine), ketorolac (Toradol), oxaprozin (Daypro), and celecoxib (Celebrex). Examples of antibiotics include amoxicillin, penicillin, sulfa drugs, erythromycin, streptomycin, tetracycline, clarithromycin, terconazole, azithromycin, bacitracin, ciprofloxacin, evofloxacin, ofloxacin, levofloxacin, moxifloxacin, gatifloxacin, aminoglycosides, tobramycin and gentamicin, as well as polymyxin B combinations including polymyxin B/trimethoprim, polymyxin B/bacitracin and polymyxin B/neomycin/gramicidin. Glaucoma treatment medications include beta-blockers, such as timolol, betaxolol, levobetaxolol, and carteolol; miotics, such as pilocarpine; carbonic anhydrase inhibitors, such as brinzolamide and dorzolamide; prostaglandins, such as travoprost, bimatoprost, and latanoprost; seretonergics; muscarinics; dopaminergic agonists; and adrenergic agonists, such as apraclonidine and brimonidine, and prostaglandins or prostaglandin analogs such as latanoprost, bimatoprost, and travoprost. Antihistamines and mast cell stabilizers include olopatadine and epinastine; the acute care anti-allergenic products ketorolac tromethamine, ketotifen fumarate, loteprednol, epinastine HCl, emedastine difumarate, azelastine hydrochloride, olopatadine hydrochloride, ketotifen fumarate, while the chronic care anti-allergenic products include pemirolast potassium, nedocromil sodium, lodoxamide tromethamine, and cromolyn sodium. Antimuscarinic drugs include atropine, scopolamine, tropicamide, ipratropium bromide, glycopyrrolate, used for myopia control. Antineovasculars include biologics ranibizumab (Lucentis) and bevacizumab (Avastin). Amblyopia medicine includes anesthetics and cycloplegics such as atropine. Retinitis pigmentosa treatment can be accomplished with N-acetylcysteine, N-acetylcysteine amide and voretigene neparvovec. Dry eye medication includes cyclosporine and lifitegrast as well as ocular lubricants such as methylcellulose, sodium carboxymethyl cellulose, hydroxyethyl cellulose, hydroxypropyl cellulose and hydroxypropylmethyl cellulose, polyethylene oxide, polyethylene glycol, and hyaluronic acid. Any of the foregoing agents can be present in free base form or as a pharmaceutically acceptable salt thereof.

Other examples of pharmaceutically active agents include nerve growth factors (e.g., human nerve growth factor), platelet-derived growth factor, transform growth factor, fibroblast growth factor (e.g., human fibroblast growth factor), growth hormone (e.g., human growth hormone), neurotrophin-3 growth factor, brain-derived neurotrophic factor, glial cell-line derived neurotrophic factor, platelet-activating factor (PAF, e.g., PAF receptor agonist and/or antagonist), tumor angiogenesis factor, albumin, β-lactoglobulin, bovine serum albumin, γ-globulin, monoclonal immunoglobulins, immunoglobulin G, ovalbumin, insulin, monoclonal antibodies (e.g., anti-hCG), alkaline phosphatase, tumor-associated antigens, catalase, ferritin, lactogen and mutants thereof, anti-horseradish peroxidase, prolactin and mutants thereof, macrophage inflammatory protein 3β, thrombospondin, trypsin, soybean trypsin inhibitor, DNA, high molecular weight reporter plasmids, RNA, heparin, lipopolysaccharide, GRGDSP peptide, and leuprolide, as well as their pharmaceutically acceptable salts. Pharmaceutically active agents, e.g., for use with EVA copolymers, are described in Schneider, C., et al., *Journal of Controlled Release* 262(2017), 284-295; and Schneider, C., et al., *Journal of Controlled Release* 278(2018), 156-158, the contents of which are incorporated herein by reference.

In some embodiments, the pharmaceutically active agent includes an anti-allergenic and/or antihistaminic compound, e.g., to prevent an allergic reaction to an ocular insert composition. In the compositions described herein, antiallergenic and antihistaminic compounds are typically used in combination with another pharmaceutically active agent. Accordingly, in some embodiments, the composition comprises a first pharmaceutically active agent and a second pharmaceutically active agent, wherein the second pharmaceutically active agent is an anti-allergenic and/or antihistaminic compound.

In some embodiments, a pharmaceutically active agent has a melting temperature of greater than about 99° C. In some embodiments, a pharmaceutically active agent is water-soluble. In some embodiments, a pharmaceutically active agent has a melting temperature of greater than about 99° C. and is water-soluble.

As used herein, "water-soluble" means that less than or equal to 10,000 parts per volume of an aqueous medium (typically, water, but sometimes, buffer) are needed to dissolve 1 part per volume of the solute. Various levels of solubility are described in the following table.

| Descriptive terms | Parts of solvent needed for 1 part solute |
|---|---|
| Very soluble | <1 |
| Freely soluble | 1-<10 |
| Soluble | 10-<30 |
| Sparingly soluble | 30-<100 |
| Slightly soluble | 100-<1000 |
| Very slightly soluble | 1000-10,000 |
| Practically insoluble or insoluble | >10,000 |

In some embodiments, a pharmaceutically active agent is very soluble, freely soluble, soluble, sparingly soluble, slightly soluble or very slightly soluble in an aqueous medium (e.g., water). In some embodiments, a pharmaceutically active agent is very soluble, freely soluble or soluble in an aqueous medium (e.g., water).

Particularly when a pharmaceutically active agent is incorporated into a composition using hot melt blending as described herein, the pharmaceutically active agent will typically be in the form of microparticles and/or nanoparticles. Accordingly, in some embodiments, the pharmaceutically active agent is in the form of particles (e.g., microparticles, nanoparticles). In some embodiments, a pharmaceutically active agent has a melting temperature of greater than about 99° C., is water-soluble, and is in the form of particles.

Typically, pharmaceutically active agent(s) account for from about 0.1% to about 99%, for example, from about 0.1% to about 75%, from about 0.1% to about 50%, from about 0.5% to about 50% or from about 1% to about 40% by weight, of a composition.

As examples and not as limitations, inserts that deliver pharmaceutically active agents include those disclosed in the following U.S. Pat. No. 3,302,646 (Behney), U.S. Pat. No. 3,416,530 (Ness), U.S. Pat. No. 4,309,996 (Theeuwes), U.S. Pat. No. 6,071,266 (Kelley), U.S. Pat. No. 6,331,313 (Wong), U.S. Pat. No. 7,211,272 (Renner), U.S. Pat. No. 8,167,855 (Leahy), U.S. Pat. No. 8,287,504 (Leahy), U.S. Pat. No. 8,574,659 (Ashton), U.S. Pat. No. 8,679,078 (Leahy), U.S. Pat. No. 8,939,948 (de Juan), U.S. Pat. No. 9,005,649 (Ho), U.S. Pat. No. 9,421,126 (de Juan), U.S. Pat. No. 9,549,846 (Clauson), U.S. Pat. No. 9,750,636 (de Juan), U.S. Pat. No. 9,814,671 (Lee), U.S. Pat. No. 9,849,085 (Ashton), U.S. Pat. No. 9,931,306 (Barman), and U.S. Pat. No. 9,937,073 (de Juan), the entire teachings of which are incorporated herein by reference.

As used herein, the term "pharmaceutically acceptable" refers to species that are, within the scope of sound medical judgment, suitable for use in contact with the tissues of mammals without undue toxicity, irritation, allergic response, and the like, and are commensurate with a reasonable benefit/risk ratio. For example, a substance is pharmaceutically acceptable when it is suitable for use in contact with cells, tissues or organs of animals or humans without excessive toxicity, irritation, allergic response, immunogenicity or other adverse reactions, in the amount used in the dosage form according to the dosing schedule, and commensurate with a reasonable benefit/risk ratio.

As used herein, the term "pharmaceutically acceptable salt" refers to those salts that are, within the scope of sound medical judgment, suitable for use in contact with the tissues of mammals without undue toxicity, irritation, allergic response, and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts include salts derived from suitable inorganic and organic acids, and suitable inorganic and organic bases.

Examples of pharmaceutically acceptable acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid or malonic acid or by using other methods used in the art, such as ion exchange. Other pharmaceutically acceptable acid addition salts include adipate, alginate, ascorbate, aspartate, benzenesulfonate, benzoate, bisulfate, borate, butyrate, camphorate, camphorsulfonate, cinnamate, citrate, cyclopentanepropionate, digluconate, dodecylsulfate, ethanesulfonate, formate, fumarate, glucoheptonate, glycerophosphate, gluconate, glutarate, glycolate, hemisulfate, heptanoate, hexanoate, hydroiodide, hydroxybenzoate, 2-hydroxy-ethanesulfonate, hydroxymaleate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 2-phenoxybenzoate, phenylacetate, 3-phenylpropionate, phosphate, pivalate, propionate, pyruvate, salicylate, stearate, succinate, sulfate, tartrate, thiocyanate, p-toluenesulfonate, undecanoate, valerate salts, and the like. Either the mono-, di- or tri-acid salts can be formed, and such salts can exist in either a hydrated, solvated or substantially anhydrous form.

Salts derived from appropriate bases include salts derived from inorganic bases, such as alkali metal, alkaline earth metal, and ammonium bases, and salts derived from aliphatic, alicyclic or aromatic organic amines, such as methylamine, trimethylamine, and picoline, or $N^+((C_1\text{-}C_4)alkyl)_4$ salts. Representative alkali or alkaline earth metal salts include sodium, lithium, potassium, calcium, magnesium, barium, and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate, and aryl sulfonate.

In one embodiment, a composition (e.g., pharmaceutical, such as ocular, composition) comprises one or more pharmaceutically active agents and a water-insoluble polymer (e.g., EVA, according to any of the embodiments described herein). In some embodiments, the composition further comprises a water-soluble polymer (e.g., PEO, according to any of the embodiments described herein). In some embodiments, the water-insoluble polymer has a melting point of less than about 99° C., for example, according to DSC ASTM D2417. In some embodiments, the water-soluble polymer has a melting point of less than about 99° C., for example, according to DSC ASTM D2417. In some embodiments, the water-soluble polymer and the water-insoluble polymer, taken together, have a processing formation melting point of less than about 99° C., for example, according to DSC ASTM D2417. Typically, in such embodiments, the water-insoluble polymer and the water-soluble polymer, when present, form a matrix, and the one or more pharmaceutically active agents is dispersed (e.g., uniformly dispersed) within the matrix.

Also provided herein is a matrix (e.g., for delivery of one or more pharmaceutically active agents), comprising water-insoluble polymer (e.g., EVA, according to any of the embodiments described herein), and a water-soluble polymer (e.g., PEO, according to any of the embodiments described herein).

Without wishing to be bound by any particular theory, it is believed that the water-insoluble polymer in the matrices and compositions described herein serves as a scaffold to provide shape and stability to the composition. In addition, it is believed that the water-insoluble polymer can prevent pharmaceutically active agent(s) in the matrix from escaping from the matrix.

Non-limiting examples of water-insoluble polymers include ethylene vinyl acetate (EVA). EVA is a copolymer of ethylene and vinyl acetate, and can be represented by the following structural formula describing a block copolymer of EVA:

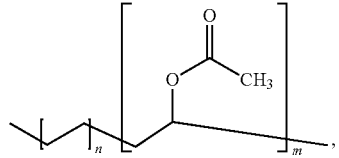

wherein n and m represent the weight percent of ethylene and vinyl acetate, respectively, in the copolymer, and the sum of n and m is 100%. Typically, m is 25% or greater (e.g., 28%, 40%). In some embodiments, the EVA has a tensile elongation of 750% or greater, for example, according to ASTM D638. In some embodiments, the EVA has a melt flow index of 6.0 g/10 min or greater, for example, according to ASTM D1238. In some embodiments, the EVA has a melting point of less than about 99° C., for example, according to DSC ASTM D2417.

Typically, the weight percentage of the water-insoluble polymer in a composition is from about 5% to about 99%, from about 20% to about 99%, from about 20% to about 75%, from about 25% to about 75% or from about 20% to about 50%.

It should be appreciated that tear fluid is an aqueous liquid. Water-soluble polymers dissolve (at least partially) in aqueous fluids, such as tear fluid. Thus, upon exposure to aqueous fluid, a water-soluble polymer present in a composition described herein is expected to dissolve (at least partially), thereby eroding from the composition. Desirably, inclusion of a water-soluble polymer in a composition described herein enhances dissolution and erosion of the pharmaceutically active agent(s) in the composition, such that the pharmaceutically active agent(s) erodes faster than it would if the water-soluble polymer were not present. The rate of transport of each pharmaceutically active agent is a direct factor of solubility of individual particles of the agent. Particles of each agent, whether alone or within an insert, will thus disperse independently, each agent at its own rate. When a water-soluble polymer is present, the water-soluble polymer transports the pharmaceutically active agent(s) dispersed within it. Hence, the rate of agent(s) delivered per unit time can be larger and can be regulated and/or controlled in manufacturing by adjusting the component relationships.

Non-limiting examples of water-soluble polymers include polyethylene oxide (Polyox or PEO), also known as polyethylene glycol (PEG). In some embodiments, the PEO has a molecular weight of from about 100,000 to about 300,000 (e.g., about 100,000, about 200,000, about 300,000). In some embodiments, the PEO has a viscosity of from about 10 CPS to about 20,000 CPS at a concentration of about 5 weight percent in water at about 25° C. (e.g., C=5% $H_2O$ at 25° C.). In some embodiments, from about 96% to about 100% of the PEO is in the form of 20 mesh particles. In some embodiments, the PEO has a melting point of less than about 99° C. Without wishing to be bound by any particular theory, it is believed that the presence of polyethylene oxide in a composition or delivery matrix described herein, particularly one for ocular administration, may inhibit allergic reaction to the composition in a subject, such as a patient. The elution of polyethylene oxide along with the pharmaceutically active agent may prevent adhesion of proteins and thus minimize the chance of developing an allergic reaction. Polyethylene oxide can also provide lubrication to the eye.

Typically, the weight percentage of a water-soluble polymer, when present, in a composition is from about 1% to about 90%, for example, from about 1% to about 75%, from about 1% to about 50%, from about 2.5% to about 85%, from about 5% to about 80%, from about 25% to about 80% or from about 40% to about 75%.

The compositions and matrices described herein may be produced by hot melt blending the components of the composition or matrix to form a hot melt blend. The hot melt blend may subsequently be shaped and/or cooled. The resulting shaped composition or matrix is also referred to herein as an insert.

Accordingly, also provided herein is a method of making a composition (e.g., pharmaceutical, such as ocular, composition), comprising hot melt blending one or more pharmaceutically active agents and a pharmaceutically acceptable carrier (e.g., one or more polymers, such as a blend of two or more polymers; a water-insoluble polymer; a water-insoluble polymer and a water-soluble polymer) to form a hot melt blend; and cooling the hot melt blend. In some embodiments, the method further comprises shaping the hot melt blend. In some embodiments, the method comprises hot melt blending one or more pharmaceutically active agents, a water-insoluble polymer (e.g., EVA, according to any of the embodiments described herein) and a water-soluble polymer (e.g., PEO, according to any of the embodiments described herein) to form the hot melt blend.

Also provided herein is a method of making a matrix (e.g., for delivery of one or more pharmaceutically active agents), comprising hot melt blending a water-insoluble polymer (e.g., EVA, according to any of the embodiments described herein) and a water-soluble polymer (e.g., PEO, according to any of the embodiments described herein) to form a hot melt blend, and cooling the hot melt blend. In some embodiments, the method further comprises shaping the hot melt blend.

It is advantageous that a therapeutic agent retain integrity during manufacturing, including melt processing, for example, as microparticle- or nanoparticle-like structures, dispersed within a blended polymer matrix. This is perhaps most useful for delivery of agents that may be the least soluble in tears and require more residence time to transport across membrane tissue, and/or where user natural tear generation retention is in fact minimal. Thus, typically, in the methods described herein the hot melt blending is performed at a low enough melt temperature (e.g., a temperature below about 99° C., below the melting temperature of the pharmaceutically active agent(s)) that the structure and/or performance of the pharmaceutically active agent(s) is not compromised. Thus, in some embodiments, the component(s) of the matrix (e.g., the water-insoluble polymer and/or the water-insoluble polymer), taken individually or collectively, have processing formation melting points of about 99° C. or less (e.g., 99° C. or less) and/or less than the melting temperature of the pharmaceutically active agent(s). In some embodiments, the hot melt blending is performed at a temperature of less than about 99° C. (e.g., less than 99° C.). In some embodiments, the hot melt blending is performed at a temperature below the melting temperature (e.g., 25° C., 50° C., 75° C., 100° C., or more, below the melting temperature) of the one or more pharmaceutically active agents.

Pharmaceutically active agents typically have melting points (Mp) greater than 99° C. For example, ciprofloxacin has a melting point of 318° C. to 320° C., dexamethasone has a melting point of 262° C. to 264° C., and olopatadine has a melting point of 242° C. to 245° C.

In use, an insert including one or more pharmaceutically active agents can be placed into an ocular device, and the assembled ocular device can be placed in an eye under an eyelid to deliver the one or more pharmaceutically active agents to the eye. An insert can, as one example, be shaped as a cylinder or rod. Alternatively, an insert can be in the form of a film or other configuration.

Without wishing to be bound by any particular theory, the following is a description of the steps believed to occur when a pharmaceutically active agent(s) is delivered to an eye from an ocular device containing a composition or insert described herein. When an insert-loaded device is placed in the eye, for example, under the bottom eyelid (inferior palpebra), it is in contact with tear fluid. The tear fluid permeates the surface of the insert and begins to dissolve water-soluble polymer to expose pharmaceutically active agent(s) to the tear fluid, which also begins to dissolve the pharmaceutically active agent. Dissolution of the water-soluble polymer also frees space within the insert, having been replaced with tear fluid in the matrix, allowing particles of pharmaceutically active agent(s) to release and transport out of the insert and/or device into tear retention zones and through ocular membrane surfaces. Thus, the water-soluble polymer and pharmaceutically active agent(s) slowly release from the ocular device into the eye. Natural tear fluid will continue to transport particles of pharmaceutically active agent(s) at ever decreasing concentrations following a first order drug delivery system. The water-insoluble polymer is expected to maintain geometrical shape of the insert, eventually becoming a scaffold comprising water-insoluble polymer and retained tear fluid. As the process of dissolution continues, the insert may swell, but the scaffold formed by the water-insoluble polymer can provide stability and prevent fracturing. The release of the water-soluble polymer can provide an added benefit of lubricating the eye. In addition, the water-soluble polymer, such as PEO, can fortify the mucin layer. The mucin layer is the deepest layer of the tear fluid, and it adheres to underlying epithelial cells of the cornea and conjunctiva.

Dispersion matrices, such as those described herein, typically have three release mechanisms that are generally operative:

Drug diffusion from the non-degraded polymer (Diffusion Controlled System),

Drug release due to polymer degradation and erosion (Erosion Controlled System) and Enhanced drug diffusion due to polymer swelling (Swelling Controlled System).

Studies described herein of various drugs incorporated into a drug insert indicated that the release kinetics appear to follow the Higuchi Model for early stages of drug release.

The compositions described herein are particularly suitable for ocular administration. The compositions described herein can, however, also be administered orally, parenterally (including subcutaneously, intramuscularly, intravenously, intradermally, by inhalation, topically, rectally, nasally, and vaginally) or buccally, or via an implanted reservoir. The term "parenteral," as used herein, includes subcutaneous, intracutaneous, intravenous, intramuscular, intraocular, intravitreal, intra-articular, intra-arterial, intrasynovial, intrasternal, intrathecal, intralesional, intrahepatic, intraperitoneal intralesional, and intracranial injection or infusion techniques.

As used herein, "topical administration" refers to administration of a substance to a particular place or particular places on or in the body of a subject without regard to the location of the effect of the substance, if any. Thus, the effect of a formulation comprising a formulation base described herein may be local or systemic. Non-limiting examples of topical routes of administration include transdermal, transmucosal (e.g., oral, nasal, vaginal, urethral), sublingual, buccal, nasal, and ocular routes of administration.

The compositions described are particularly suitable for administration that brings the composition in contact with a bodily fluid, such as tear fluid, rectal fluid, saliva, etc. Thus, in some embodiments, a composition described herein is administered to a mucous membrane (e.g., oral, nasal, vaginal, urethral mucous membrane), under the tongue, the cheek, the nose, and/or the eye of a subject.

The compositions described herein can be in any dosage form suitable for the intended mode of administration. For example, the compositions described herein can be in the form of a semi-erodible polymer matrix, for example, for ocular administration. The compositions described herein can also be in solid form, for example, for ocular administration. Compositions provided herein can be orally administered in any orally acceptable dosage form including, but not limited to, a solid dosage form (e.g., capsules, tablets, pills, powders, granules), aqueous suspensions, dispersions, and solutions. Compositions suitable for buccal or sublingual administration include tablets, lozenges, and pastilles. For rectal administration or administration to the lower intestinal tract, the formulation can be in the form of a suppository. A suppository is typically formulated with a suitable non-irritating excipient that is solid at room temperature but liquid at rectal temperature and, therefore, will melt in the rectum. Such excipients include cocoa butter, beeswax, and polyethylene glycols. For ophthalmic use, formulations can be provided as micronized suspensions in isotonic, pH-adjusted sterile saline, or, preferably, as solutions in isotonic, pH-adjusted sterile saline, either with or without a preservative such as benzylalkonium chloride. Alternatively, for ophthalmic uses, the formulations can be formulated as ointments, for example, with petrolatum. For nasal administration (e.g., inhalation), formulations can be prepared as solutions in saline, employing benzyl alcohol or other suitable preservatives, absorption promoters to enhance bioavailability, fluorocarbons, and/or other conventional solubilizing or dispersing agents.

The compositions described herein can further include an excipient (e.g., a pharmaceutically acceptable excipient), e.g., to increase the stability of the composition, or other physical characteristic of the composition. Typically, such carriers are non-bioactive, meaning they have insubstantial or no biological activity and/or produce insubstantial or no biological effect, e.g., in the amount administered. Examples of excipients include preservatives, flavor enhancers, diluents, solvents, glycerin, gelatin, albumin, lactose, starch, stabilizers, melting agents, emulsifying agents, suspending agents, salts, and buffers. An excipient can be organic or inorganic.

The compositions described herein can be formulated for immediate release or non-immediate release, such as delayed, sustained, or extended release. The compositions described herein can also be formulated to provide controlled release of a pharmaceutically active agent(s) contained therein. In some embodiments, the compositions described herein are formulated for extended release, for example, for release over about 12 hours, about 24 hours, about 36 hours, about 48 hours, about 72 hours, about 96 hours, about five days, about six days or about seven days. In some embodiments, a composition described herein is formulated for release over from about 12 hours to about 48 hours (e.g., about 12 hours, about 24 hours).

The amount of a pharmaceutically active agent in a single dosage form will vary depending upon the subject treated, the particular mode of administration and the activity of the agent employed. Preferably, compositions should be formulated so that a dosage of from about 0.01 mg/kg to about 100 mg/kg body weight/day of the compound, or pharmaceutically acceptable salt thereof, can be administered to a subject receiving the composition. For example, in some embodiments, a dose can range from about 0.5 mg/kg to about 100 mg/kg of body weight or, alternatively, from about 1 mg/dose to about 1000 mg/dose. Other suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. In some embodiments, compositions are formulated so that a dosage described herein of a pharmaceutically active agent can be administered to a subject receiving the composition.

The desired dose may conveniently be administered in a single dose, for example, such that the agent is administered once per day, as in daily ocular wear applications, or as multiple doses administered at appropriate intervals, for example, such that the agent is administered 2, 3, 4, 5, 6 or more times per day. The daily dose can be divided, especially when relatively large amounts are administered, or as deemed appropriate, into several, for example 2, 3, 4, 5, 6 or more, administrations.

It should also be understood that a specific dosage and treatment regimen for any particular subject will depend upon a variety of factors, such as the activity of the specific agent employed, the age, body weight, general health, sex, diet, time of administration, rate of excretion, drug combination, the judgment of the treating physician and the severity of the particular disease, disorder or condition being treated. The amount of an agent in a composition will also depend upon the particular agent in the composition. Determining the dosage for a particular agent, subject and disease, disorder or condition is well within the abilities of one of skill in the art. Preferably, the dosage does not cause or produces minimal adverse side effects.

Methods of Treatment

The devices and inserts described herein can be used for treatment of conditions of the eye. Thus, also provided herein is a method of treating an eye condition in a subject in need thereof, comprising administering to the subject a therapeutically effective amount of a composition described herein. Examples of conditions of the eye that may be beneficially treated using the devices and/or compositions described herein include dry eye, glaucoma, allergies, infection (e.g., bacterial, viral and other infection), chronic inflammatory conditions such as acne rosacea keratitis, cyclitis, and blepharitis, selected retinal conditions such as diabetic retinopathy, age related macular degeneration and other retinal conditions, post-surgery, and amblyopia. Pharmaceutically active agents useful in the treatment of the conditions described herein are as described throughout.

"Treating," as used herein, refers to taking steps to deliver an agent to a subject to obtain desired or beneficial results (e.g., as by administering to a subject one or more therapeutic agents). Non-limiting examples of beneficial results include inhibition of a disease or condition (e.g., as by slowing or stopping its progression or causing regression of the disease or condition), and relief of one or more symptoms resulting from the disease or condition. A person skilled in the art is capable of identifying beneficial results specific to a particular disease or condition to be treated.

"Administering," as used herein, refers to taking steps to deliver an agent to a subject, such as a mammal, in need thereof (e.g., as by administering to a mammal one or more pharmaceutically active agents). Administering can be performed, for example, once, a plurality of times, and/or over one or more extended periods. Administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. Routes of administration consistent with the compositions and methods described herein are as discussed in the context of the insert compositions.

"A therapeutically effective amount" is an amount effective, at dosages and for periods of time necessary, to achieve a desired therapeutic result (e.g., treatment, inhibition or amelioration of a disease or condition). The full therapeutic effect does not necessarily occur by administration of one dose, and may occur only after administration of a series of doses. Thus, a therapeutically effective amount may be administered in one or more administrations. A therapeutically effective amount may vary according to factors such as disease state, age, sex, and weight of a mammal, mode of administration and the ability of a therapeutic, or combination of therapeutics, to elicit a desired response in an individual. A therapeutically effective amount of an agent to be administered can be determined by a clinician of ordinary skill using the guidance provided herein and other methods known in the art.

As used herein, "subject" refers to a mammal, and includes humans and non-human mammals, such as, dogs, monkeys, pigs, rats, mice, cats, dogs, rabbits, cattle, sheep, goats, horses, etc. A "patient" is a human subject. In some embodiments, a subject is a human.

EXEMPLIFICATION

Example 1. Insert Preparation

Inserts were prepared for testing with the composition of water-insoluble polymer [A] percent (A %), water-soluble polymer [B], if any, percent (B %), and drug of interest to evaluate [C] percent (C %) identified in the Tables that follow. The components [A], [B], and [C] were obtained in powder form.

The composition began as a dry-mixed, weight-controlled blend of the identified constituents with ratios as listed in each Table. The blended dry mix was then moved into a cylindrical injection chamber, which had thermal control to heat the mixture to a set process temperature. Thermal heating was used to heat the low melting A % and B % polymeric materials to flow carry the dispersed C % into a metallic forming mold to create an insert, without impacting or degrading the C % (drug), which has a higher melting point and thus remained in particulate form dispersed throughout the mixture. Upon reaching the desired process temperature, a plunger or solid rod was inserted into the chamber. The exit orifice of the heated injection chamber was physically engaged and sealed to an empty metallic mold chamber. Force was applied by the plunger to the melted material to transfer the fluid-like, particle-filled polymer mix from the injection chamber into the metallic forming mold chamber. The previously empty metallic mold chamber was thereby filled by the transfer of the mixture. The plunger solid rod was retracted. The injection chamber was disengaged from the metallic forming mold. After a period of time for cooling to solidify the mix, the metallic forming mold was opened. The resulting insert, in solid form, shaped by and in the geometric size provided by the metallic mold chamber and of the composition indicated in each Table that follows was removed from the metallic mold chamber for testing.

In the Tables that follow, "Rod" refers to results of tests of an insert that is not in an ocular device, and "In Device" refers to tests of an insert that is in an ocular device.

Example 2. Testing Protocol Used for Therapeutic Agents

The Tables that follow provide, for illustration purposes, results of testing performed on numerous compositions ex vivo using a UV scanning spectrophotometer calibrated to the therapeutic agent to detect the concentration of that therapeutic agent in a 2 ml to 3 ml volume of phosphate buffer at pH 7, and evaluating the percent 'daily' release of drug for Ocular Daily Wear (e.g., about 12- to about 24-hour wear). Ocular Daily Wear is defined by FDA Class II CFR 866.5925 products currently indicated for ocular use and sclera tissue contact.

To begin testing, a UV scanning spectrophotometer concentration calibration curve for the therapeutic agent was established. The insert was prepared to the specification in the particular Table, and the time duration sample plan for measurement was determined. The insert was weighed to establish T=0. The insert was immersed in phosphate buffer of a fixed constant volume. A mean body temperature of 37° C. (e.g., from about 36.5° C. to about 37.5° C.) was simulated for the identified time interval. The insert was transferred and immersed at the end of each time period into a new phosphate buffer test container. The simulated mean 37° C.-body temperature was continued to next time interval. The UV scanning spectrophotometer data was generated for each time interval sample. The release rate was calculated versus time for the therapeutic agent, and graphical plots of the data were generated.

TABLE 7

| Geometry | Structural | A % Erodible | B % | Pharmaceutical | C % | 1 Day % Release | 2 Day % Release |
| --- | --- | --- | --- | --- | --- | --- | --- |
| Rod | EVA (40% vinyl acetate) | 90 | — | — Ciprofloxacin FB | 10 | 1.45% | |

TABLE 7-continued

| Geometry | Structural | A % | Erodible | B % | Pharmaceutical | C % | 1 Day % Release | 2 Day % Release |
|---|---|---|---|---|---|---|---|---|
| 2 Component | EVA (40% vinyl acetate) | 90 | — | — | Ciprofloxacin HCl | 10 | 4.06% | |
| Rod | EVA (40% vinyl acetate) | 40 | PEO | 40 | Ciprofloxacin FB | 20 | 8.97% | |
| 3 Component | EVA (40% vinyl acetate) | 40 | PEO | 40 | Ciprofloxacin HCl | 20 | 4.91% | |
| In Device | EVA (40% vinyl acetate) | 40 | PEO | 40 | Ciprofloxacin FB | 20 | 10.23% | 12.5% |
| In Device | EVA (40% vinyl acetate) | 40 | PEO | 40 | Ciprofloxacin HCl | 20 | 6.55% | 8.5% |

Figure 28A:
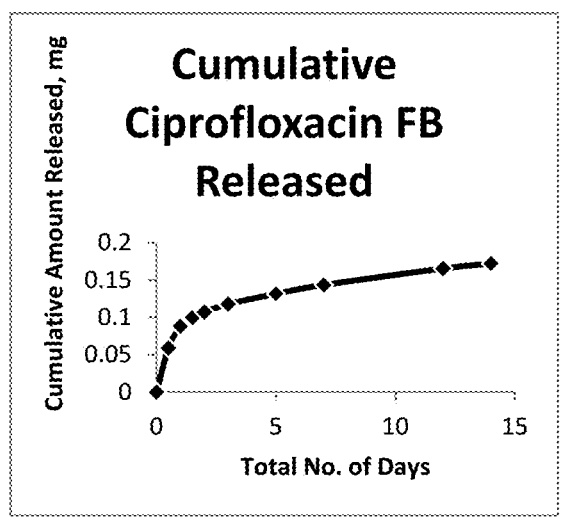
FIG. 28A is a graph of cumulative ciprofloxacin FB released versus time, and shows the release profile of the three-component, in device inserts from Table 7.
Figure 28B:
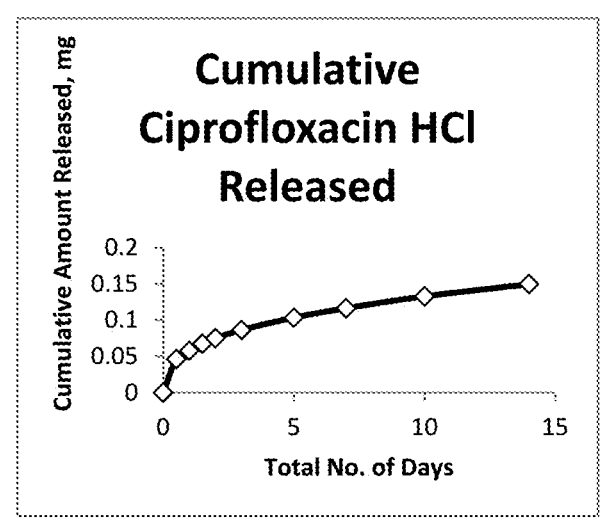
FIG. 28B is a graph of cumulative ciprofloxacin hydrochloride released versus time, and shows the release profile of the three-component, in device inserts from Table 7.

FIGS. 28A and 28B are plots of data obtained from the three-component, in-device inserts described in Table 7, and show cumulative amount of ciprofloxacin FB and ciprofloxacin hydrochloride, respectively, released from the insert over a period of several days. The ciprofloxacin FB 10.23% one-day release (Table 7) compares favorably to the one-day release of ciprofloxacin from the two-component EVA mixtures (1.45% and 4.06%).

TABLE 8

| Geometry | Structural | A % | Erodible | B % | Pharmaceutical | C % | 1 Day % Release | 2 Day % Release |
|---|---|---|---|---|---|---|---|---|
| Rod | EVA (40% vinyl acetate) | 80 | — | — | Dexamethasone FB | 20 | 6.14% | |
| | EVA (40% vinyl acetate) | 80 | — | — | Dexamethasone 21 Acetate | 20 | 1.89% | |
| 2 Component | EVA (40% vinyl acetate) | 80 | — | — | Dexamethasone Phosphate | 20 | 3.39% | |
| In Device | EVA (40% vinyl acetate) | 40 | PEO | 40 | Dexamethasone FB | 20 | 12.32% | 16.03% |
| 3 Component | EVA (40% vinyl acetate) | 40 | PEO | 40 | Dexamethasone Phosphate | 20 | 82.7% | 85.3% |

Figures 29A, 29B:
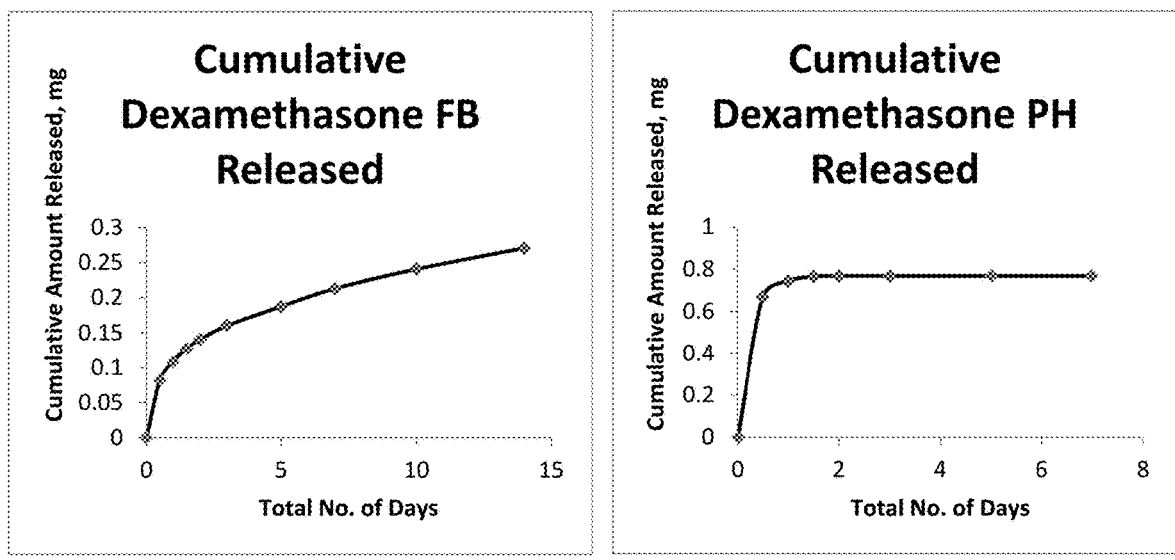
FIG. 29A is a graph of cumulative dexamethasone FB released versus time, and shows the release profile of the three-component, in device inserts from Table 8.
FIG. 29B is a graph of cumulative dexamethasone phosphate released versus time, and shows the release profile of the three-component, in device inserts from Table 8.

FIGS. 29A and 29B are plots of data obtained from the three-component inserts described in Table 8, and show cumulative amount of dexamethasone FB and dexamethasone phosphate, respectively, released from the insert over several days. The dexamethasone phosphate 82.7% one-day release compares favorably to the EVA, two-component dexamethasone mixtures (3.39%, 6.14%, and 1.89%).

TABLE 9

| Geometry | Structural | A % | Erodible | B % | Pharmaceutical | C % | 1 Day % Release | 2 Day % Release |
|---|---|---|---|---|---|---|---|---|
| In Device 3 Component | EVA (40% vinyl acetate) | 40 | PEO | 40 | Olopatadine FB | 20 | 35% | 43% |

Figure 30:
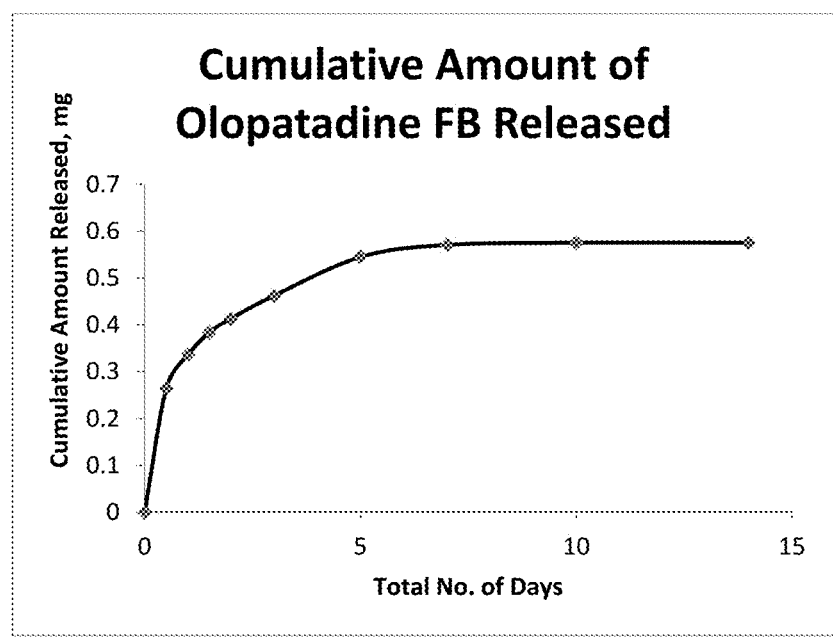
FIG. 30 is a graph of cumulative olopatadine FB released versus time, and shows the release profile of the three-component, in device insert from Table 9.

FIG. 30 is a plot of data obtained from the three-component insert described in Table 9, and shows cumulative amount of olopatadine FB released from the insert over several days. The olopatadine release curve follows the consistent pattern and timing of the previous therapeutic agent examples with similar proportional ratio of components.

Example 3. Testing Protocol Used for the EVA/PEO Matrix

The EVA/PEO matrix testing method followed the same sequence as the testing protocol for therapeutic agents described above with some exceptions. The EVA/PEO matrix testing was performed on a two-component mixture: A %+B %=100%. PEO is a lubricant well known for its ocular therapeutic benefit, but is not detectable using the UV scanning spectrophotometer. Accordingly, a mass loss method was employed for PEO.

The insert was manufactured to the specification in the matrix formulation tables.

The time duration sample plan for measurement was established. The sample was weighed to determine T=0. The test sample was placed in a new phosphate buffer at a fixed volume. Mean body temperature of 37° C. was simulated for the identified time interval. The test sample was transferred at the end of each time interval into a dry container. The insert was patted dry and weighed to establish its hydrated mass. The insert was air dried for two days, and then dried in an oven at 37° C. for one more day. The insert, which was at "Dry Weight," was weighed. The release rate versus time for the PEO component was calculated and the graphical plots were generated.

Tables 10A, 10B, 10C, and 10D are summaries of experimentation to evaluate the rate of release of the water-soluble polymer [B %] in an A % (Structural)+B % (Erodible)=100% combination. The PEO release kinetics was studied as a function of EVA %; PEO %; and PEO molecular weights, systematically varied.

TABLE 10A

| | Sample No. | | | | |
|---|---|---|---|---|---|
| | 1 | 2 | 3 | 4 | 5 |
| Composition: A % + B % | | | | | |
| A % EVA 40% VINYL ACETATE | 60 | 50 | 25 | 25 | 25 |
| B % Polyox (PEO) 200,000 Mw | 40 | 50 | 75 | 75 | 75 |
| Initial rod sample weight, mg | 12.8 | 13.2 | 12.3 | 12.7 | 12.9 |
| Amount of EVA in the sample, mg | 7.68 | 6.6 | 3.08 | 3.18 | 3.23 |
| Amount of Polyox in the sample, mg | 5.12 | 6.6 | 9.22 | 9.52 | 9.67 |
| Release time, hours | 12 hr | 12 hr | 12 hr | 24 hr | 24 hr |
| Hydrated rod sample weight, mg | 14.4 | 15.0 | 11.9 | 6.4 | 5.9 |
| Dried rod weight after release, mg | 12.2 | 12.0 | 8.6 | 4.7 | 4.4 |
| Weight loss due to Polyox erosion, mg | 0.6 | 1.2 | 3.7 | 8.0 | 8.5 |
| % Polyox eroded from initial Polyox loading | 11.7 | 18.2 | 40.1 | 84.0 | 87.9 |

TABLE 10B

| | Sample# | | | | |
|---|---|---|---|---|---|
| | 1 | 2 | 3 | 4 | 5 |
| Composition: A % + B % | | | | | |
| A % EVA 40% VINYL ACETATE | 60 | 50 | 25 | 25 | 25 |
| B % Polyox (PEO) 300,000 Mw | 40 | 50 | 75 | 75 | 75 |
| Initial rod sample weight, mg | 12.6 | 13.0 | 11.2 | 12.1 | 13.1 |
| Amount of EVA in the sample, mg | 7.56 | 6.5 | 2.8 | 3.03 | 3.28 |
| Amount of Polyox in the sample, mg | 5.04 | 6.5 | 8.4 | 9.07 | 9.82 |
| Release time in hours | 12 | 12 | 12 | 24 | 24 |

TABLE 10B-continued

| | Sample# | | | | |
|---|---|---|---|---|---|
| | 1 | 2 | 3 | 4 | 5 |
| Hydrated rod sample weight, mg | 13.4 | 14.8 | 11.7 | 6.6 | 7.3 |
| Dried rod weight after release, mg | 12.0 | 11.6 | 7.6 | 4.8 | 4.8 |
| Weight loss due to Polyox erosion, mg | 0.6 | 1.4 | 3.6 | 7.3 | 8.3 |
| % Polyox eroded from initial Polyox loading | 11.9 | 21.5 | 42.9 | 80.4 | 84.5 |

TABLE 10C

| | Sample | | | | |
|---|---|---|---|---|---|
| | 1 | 2 | 3 | 4 | 5 |
| Composition: A % + B % | | | | | |
| A % EVA 40% VINYL ACETATE | 60 | 50 | 25 | 25 | 25 |
| B % Polyox (PEO) 100,000 Mw | 40 | 50 | 75 | 75 | 75 |
| Initial rod sample weight, mg | 11.5 | 13.2 | 10.2 | 12.2 | 11.4 |
| Amount of EVA in the sample, mg | 6.90 | 6.60 | 2.55 | 3.05 | 2.85 |
| Amount of Polyox in the sample, mg | 4.60 | 6.60 | 7.65 | 9.15 | 8.55 |
| Release time, hours | 12 | 12 | 12 | 24 | 24 |
| Hydrated rod sample weight, mg | 12.0 | 13.5 | 6.3 | 4.7 | 3.9 |
| Dried rod weight after release, mg | 9.8 | 10.1 | 4.9 | 3.5 | 3.1 |
| Weight loss due to Polyox erosion, mg | 1.7 | 3.1 | 5.3 | 8.7 | 8.3 |
| % Polyox eroded from initial Polyox loading | 37.0 | 47.0 | 69.3 | 95.1 | 97.1 |

Figure 31A:
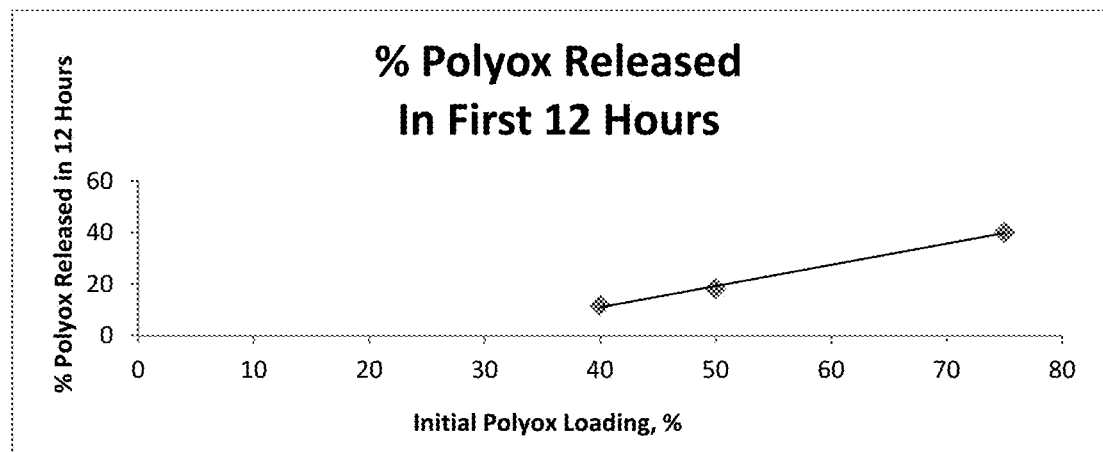
FIG. 31A is a graph of percentage polyox 200,000 MW released in twelve hours versus percentage of initial polyox 200,000 MW loading, and shows the impact of polyox loading on polyox release for polyox 200,000 MW.
Figure 31B:
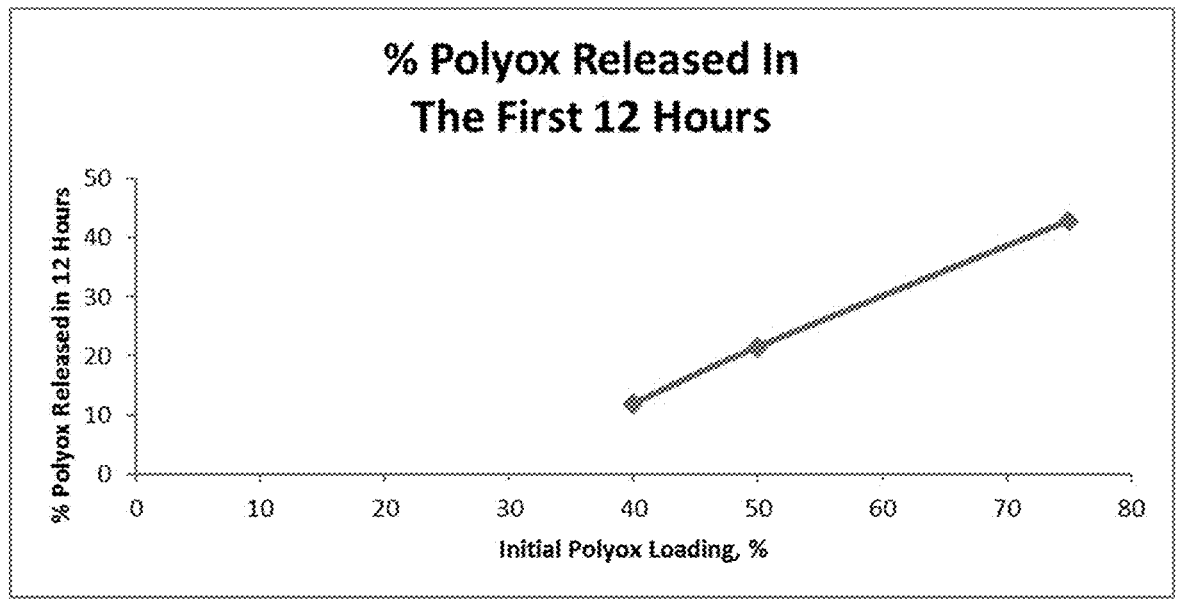
FIG. 31B is a graph of percentage polyox 300,000 MW released in twelve hours versus percentage of initial polyox 300,000 MW loading, and shows the impact of polyox loading on polyox release for polyox 300,000 MW.
Figure 31C:
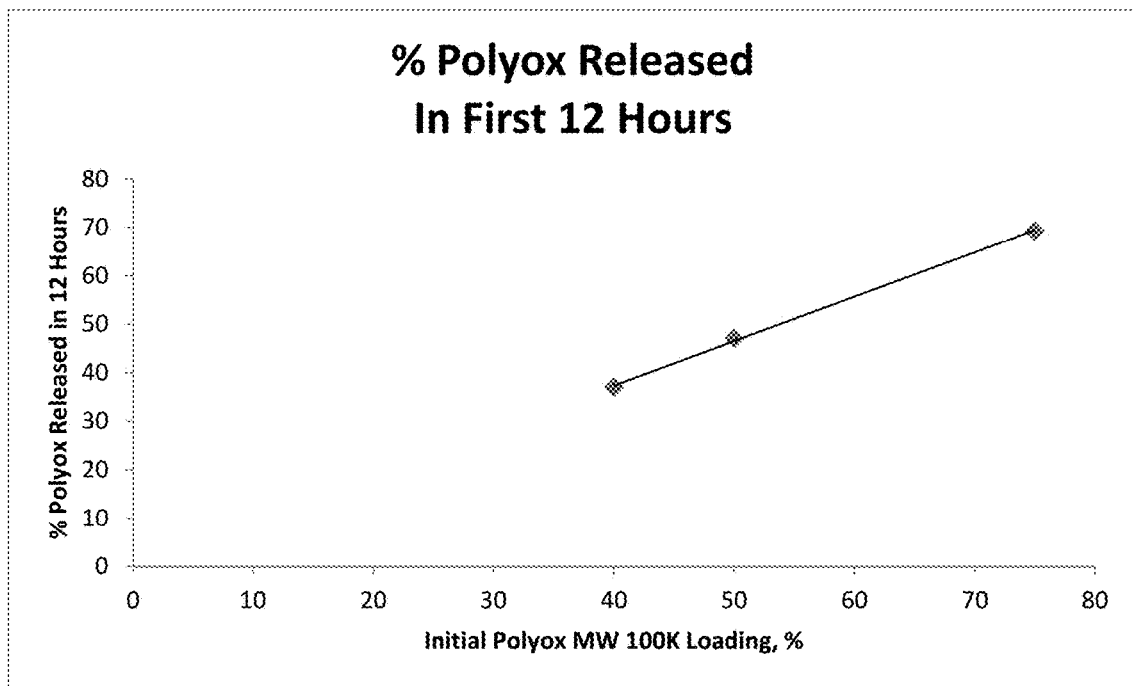
FIG. 31C is a graph of percentage polyox 100,000 MW released in twelve hours versus percentage of initial polyox 100,000 MW loading, and shows the impact of polyox loading on polyox release for polyox 100,000 MW.

Kinetic studies illustrated by Tables 10A, 10B, and 10C, and corresponding FIGS. 31A, 31B and 31C illustrate the capability of the PEO component to drive release in the first 12 to 24 hours of insert wear.

Table 10D is a summary of the results from Tables 10A, 10B and 10C.

TABLE 10D

| Initial Polyox % | Polyox MW 100K Series 1 % polyox released | Polyox MW 200K Series 2 % polyox released | Polyox MW 300K Series 3 % polyox released |
|---|---|---|---|
| 40 | 37 | 11.7 | 11.9 |
| 50 | 47 | 18.2 | 21.5 |
| 75 | 69.3 | 40.1 | 42.9 |

Figure 31D:
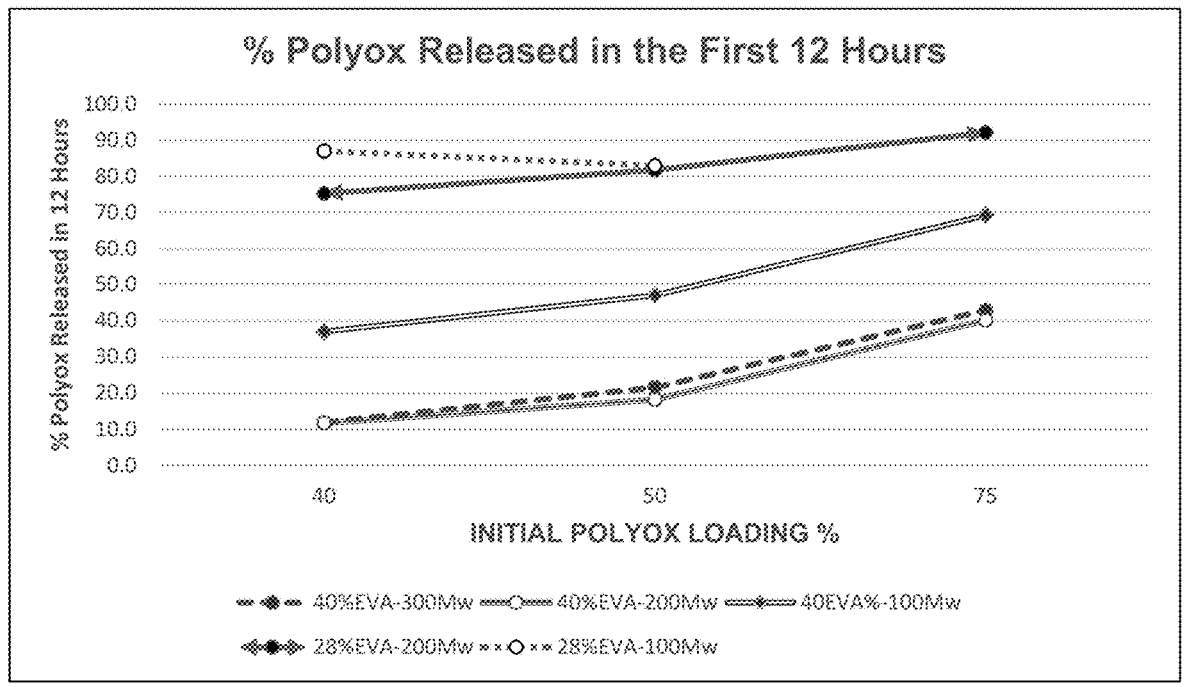
FIG. 31D is a graph of percentage polyox released in twelve hours versus percentage of initial polyox loading, and shows the impact of polyox loading on polyox release for various insert compositions.

Table 10E and corresponding FIG. 31D provide a comparison of percentage of polyox released in the first 12 hours as a function of initial polyox loading for polyox Mw 100K, 200K and 300K with EVA 4030AC (EVA 40, meaning 40% vinyl acetate EVA block copolymer), and Polyox Mw 100K and 200K with EVA 2816 (EVA 28, meaning 28% vinyl acetate EVA block co-polymer).

TABLE 10E

| | Graph Labels: | | | | |
|---|---|---|---|---|---|
| Polyox % | EVA 28 Polyox 100 Mw 28% EVA-100 Mw 12 hr Release % | EVA 28 Polyox 200 Mw 28% EVA-200 Mw 12 hr Release % | EVA 40 Polyox 100 Mw 40EVA %-100 Mw 12 hr Release % | EVA 40 Polyox 200 Mw 40% EVA-200 Mw 12 hr Release % | EVA 40 Polyox 300 Mw 40% EVA-300 Mw 12 hr Release % |
| 40 | 87.0 | 75.3 | 37.0 | 11.7 | 11.9 |
| 50 | 83.0 | 81.8 | 47.0 | 18.2 | 21.5 |
| 75 | | 92.1 | 69.3 | 40.1 | 42.9 |

The release rate of polyox from the matrix reaches a lower limit around Mw of 200,000 when combined with 40% EVA, and is rapid over the same period of time when combined with 28% EVA. Data also indicated that 40% EVA-polyox combinations for molecular weights above 200,000 may release from the matrix at about the same general rate for a 12-hour time period as demonstrated by the 300,000 Mw Data.

From a formulation point of view, a workable molecular weight range for a 12 to 24-hour release using an EVA/PEO matrix includes PEO at 300,000 MW or less. Further, blends of differing PEO molecular weights less than 300,000 can be an additional rate control tool to adjust an erosion rate (of a drug) from a matrix, which is an important tool to achieve a desired therapeutic design goal for drug delivery. The ability to control delivery of a drug using disclosed materials and methods is important for precise drug delivery, which is of significance for many drugs.

Example 4. Demonstration of Ciprofloxacin FB Delivery Rate Control Using the EVA/PEO Matrix Table 10F is a summary of the matrix compositions and delivery rates of ciprofloxacin FB over 7 days, where the PEO concentration of the three-component system has been modified. The first data (Series 1) has been shown within Table 7 as part of the ciprofloxacin group of drugs. The last data (Series 4) is the two-component system most similar to the two-component (EVA+Drug) formulation from Table 7.

TABLE 10F

| Composition | Series 1 | Series 2 | Series 3 | Series 4 |
|---|---|---|---|---|
| EVA 40% vinyl acetate % | 40 | 60 | 65 | 70 |
| % polyox 100,000 Mw | 40 | 10 | 5 | 0 |
| % ciproFB | 20 | 30 | 30 | 30 |
| Total# days | % tot rel. | % tot rel. | % tot rel. | % tot rel. |
| 0 | 0 | 0 | 0 | 0 |
| 0.5 | 6.9 | 6.8 | 3.7 | 4 |
| 1 | 10.3 | 8.6 | 4.6 | 5 |
| 1.5 | 11.6 | 9.6 | 5.1 | 5.5 |
| 2 | 12.4 | 10.3 | 5.4 | 5.9 |
| 3 | 13.7 | 11.4 | 5.9 | 6.3 |
| 5 | 15.3 | 13 | 6.6 | 6.7 |
| 7 | 16.7 | 14.4 | 7.2 | 7 |

Figure 32:
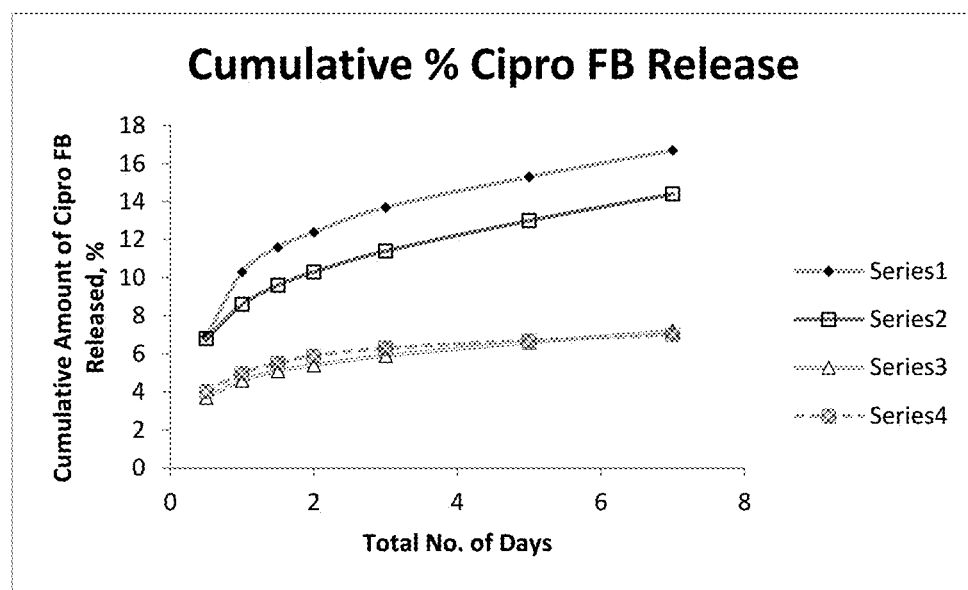
FIG. 32 is a graph of cumulative percentage of ciprofloxacin FB released from an insert versus time, and shows the cumulative percentage of ciprofloxacin released from an insert, in device over seven days.

Table 10D and Table 10F and corresponding FIG. 32 demonstrate the range of drug delivery rate control as a function of formulation concentrations, PEO molecular weight selection blending, and EVA vinyl acetate concentrations that the EVA/PEO matrix system can provide.

The disclosure is supplemented by the following references, which are incorporated here by reference in their entirety:

[1] Quaia, C; Optican, L; (2001) "Three Dimensional Rotations of the Eye" Chapter for Alder's Physiology of the Eye, 10th Edition. Kauffman & Alm, Eds. National Eye Institute; NIH.

[2] Doughty M J, Laiquzzaman M, Oblak E, Button N.; (2002) "The tear (lacrimal) meniscus height in human eyes: a useful clinical measure or an unusable variable sign?" Cont Lens Anterior Eye. 2002 June; 25(2):57-65.

[3] Bekerman, I; Gottlieb, P; & Vaiman, M; (2014) "Variations in Eyeball Diameters of the Healthy Adults," Journal of Ophthalmology, vol. 2014, Article ID 503645, 5 pages, 2014.

[4] Atchison, D; Jones, C. E; Schmid, K. L; Pritchard, N; Pope, J; Strugnell, W; Riley, R; (2004) "Eye Shape in Emmetropia and Myopia" Investigative Ophthalmology & Visual Science; October 2004 Vol 45, No. 10 PP 3380-3386.

[5] Vojnikovic, B; Gabric, N; Dekaris, I; Juric, B (2013) "Curvature Analysis of the Corneal Front and Back Surface" Coll. Antropol. 37 (2013) Suppl. 1:93-96.

[6] Hashemi, H; Khabazkhoob, M; Emamian, M. H; Shariati, M; Yekta, A; Fotouhi, A; "White to white corneal diameter distribution in an adult population" Journal of Current Ophthalmology 27 (2015) 21-24 http://dx.doi.org/10.1016/j.joco.2015.09.001.

[7] Khan, I. J; Abdul-Jabbar, G; Hodson, J; Edmunds, M. R; Cottrell, P; Evans, S; Williams, G. P; Rauz, S; (2014) "Defining the limits of Normal Conjunctival Fornix Anatomy in a Healthy South Asian Population" Opthamology 2014; 121:492-497 http://dx.doi.org/10.1016/j.optha.2013.09.033.

[8] Vasanthakumar, P; Kumar, P; Rao, M; (2013) "Anthropometric Analysis of Palpebral Fissure Dimensions and its Position in South Indian Ethnic Adults" Oman Medical Journal (2013) Vol. 28, No 1:26-32 DOI 10.5001/omj.2013.06.

[9] Robinson D A; (1964) "The Mechanics of Human Saccadic Eye Movement" J. Physiol [1964] 174 PP 245-264.

[10] Laurutis, V. P; Robinson, D. A; (1986) "The Vestibulo-Ocular Reflex during Human Saccadic Eye Movements" J. Physiol. (1986) 373, pp. 209-233.

[11] Findlay, J; & Walker, R (2012) "Human Saccadic Eye Movements" Scholarpedia, 7(7):5095.

[12] Castelhano, M; & Henderson, J (2008) "Stable Individual Differences Across Images in Human Saccadic Eye Movements" Canadian Journal of Experimental Psychology: 2008 Vol. 62 No. 1 PP 1-14.
[13] Bentivolgio A R; Bressman S; Cassetta E; Carretta, D; Tonali, T; Albanese, A: "Analysis of Blink Rate Patterns in Normal Subjects" Movement Disorders Vol. 12 No. 6, 1996 PP 1028-1034.
[14] Abelson, M; ORA, Andover, MA "It's Time to Think About the Blink" Pub 13-June 2011.
[15] Ousler. G W.; Abelson, M; Johnston, P; Rodriguez, J; Lane, K; Smith, L: 2014 "Blink patterns and lid contact times in dry-eye and normal subjects". Clinical Ophthalmology (Auckland N.Z.) 8 (1): 869-874.
[16] Francis, I C; Stapelton, F; Ehrmann, K; Coroneo, M T; (2006) "Lower eyelid tensometry in younger and older normal subjects" Eye (2006) 20 (pp 166-172).
[17] S. K. Savale Technical operations/services Scientist at Mylan Laboratories LTD Nasik, Maharashtra, India: Department of Pharmaceutics, Slide Presentation 2015-2016 'Slide #4'. https://www.slideshare.net/sagarsavale1/drug-release-kinetics.
[18] C. Mircioiu, V. Voicu, V. Anuta, A. Tudose, C. Celia, D. Paolino, M. Fresta, R. Sandulovici, I. Miricioiu Modeling "Mathematical Modeling of Release Kinetics from Supramolecular Drug Delivery Systems" Pharmaceutics 2019, 11, 140 doi: 10.3390/pharmaceutics11030140 www.mdpi.com/journal/pharmaceutics.
[19] X. Huang, & C. S. Brazel: "On the importance and mechanisms of burst release in matrix-controlled drug delivery systems" Journal of Controlled Release 73 (2001) pp 121-136.
[20] C. Brazel & X. Huang 'The Cost of Optimal Drug Delivery: Reducing and preventing the Burst Effect in Matrix Systems' Carrier-Based Drug Delivery Chapter 19; DOI: 10.1021/bk-2004-0879.ch019.
[21] Mishmia, S.; Gasset, P.; Klyce, D. Jr.; & Baum, J. L; (1966) "Determination of tear volume and tear flow", Investigative Ophthalmology, Vol. 5, Number 3, 1966, pp. 264-276.
[22] Brecher, Jonathan (2006). "Graphical representation of stereochemical configuration (IUPAC Recommendations 2006)" (PDF). Pure Appl. Chem. 78 (10): 1897-1970. doi:10.1351/pac200678101897.
[23] Brecher, Jonathan (2008). "Graphical representation standards for chemical structure diagrams (IUPAC Recommendations 2008)". Pure and Applied Chemistry. 80 (2): 277-410. doi:10.1351/pac200880020277. ISSN 1365-3075.
[24] Almeida, et al., "Sustained release from hot-melt extruded matrices based on ethylene vinyl acetate and polyethylene oxide," European Journal of Pharmaceutics and Biopharmaceutics 82 (2012) 526-533.

The teachings of all patents, published applications and references cited herein are incorporated herein by reference in their entirety.

While example embodiments have been particularly shown and described, it will be understood by those skilled in the art that various changes in form and details may be made therein without departing from the scope of the embodiments encompassed by the appended claims.

What is claimed is:

1. An ocular device comprising:
at least three plates, wherein a given plate is configured to deliver a substance to an eye and at least one plate comprises a back surface, the back surface having at least one protrusion having a contact surface to contact an outermost layer of the eye and to provide an offset space between the outermost layer of the eye and the back surface of the at least one plate, and the at least one plate is connected to an elongated support member of flexible material comprising a first end and a second end.

2. The ocular device of claim 1, wherein the at least one plate is connected proximate to the first end of the elongated support member and a plate is connected proximate to the second end of the elongated support member.

3. The ocular device of claim 2, wherein the elongated support member, the at least one plate connected proximate to the first end of the elongated support member, and the plate connected proximate to the second end of the elongated support member are substantially coplanar, flexibly interconnected, and configured to adapt to irregular surfaces.

4. The ocular device of claim 1, wherein a flexible connector connects the at least one plate to the elongated support member.

5. The ocular device of claim 4, wherein a connection between the flexible connector and the elongated support member is configured to be located adjacent to a canthus of the eye, when the ocular device is under an eyelid.

6. The ocular device of claim 1, wherein the contact surface forms a boundary around the offset space.

7. The ocular device of claim 1, wherein the at least one protrusion is a complete annulus.

8. The ocular device of claim 1, wherein the at least one protrusion is toroidal.

9. The ocular device of claim 1, wherein the back surface has at least three protrusions having a contact surface to contact the outermost layer of the eye and to provide the offset space between the outermost layer of the eye and the back surface of the at least one plate.

10. The ocular device of claim 1, wherein the contact surface is a convex contact surface.

11. The ocular device of claim 1, wherein the at least one plate further comprises a front surface on an other side of the at least one plate from the back surface, the front surface having at least one protrusion having a contact surface to contact the outermost layer of the eye of the eye and to provide an offset space between the outermost layer of the eye and the front surface of the at least one plate.

12. The ocular device of claim 11, wherein the contact surface of the at least one protrusion of the front surface is a convex contact surface.

13. The ocular device of claim 1, wherein perimeter of a plate is curved.

14. The ocular device of claim 1, wherein the at least one plate extends laterally from the elongated support member.

15. The ocular device of claim 1, wherein elongated support member length is between about 3 millimeters and about 24 millimeters.

16. The ocular device of claim 15, wherein the length of the elongated support member is between about 3 millimeters and about 8 millimeters.

17. The ocular device of claim 15, wherein the length of the elongated support member is between about 4 millimeters and about 10 millimeters.

18. The ocular device of claim 15, wherein the length of the elongated support member is between about 6 millimeters and about 16 millimeters.

19. The ocular device of claim 1, wherein the at least one plate is connected to the elongated support member between the first end and the second end of the elongated support member, the at least one plate being substantially coplanar with the elongated support member.

20. The ocular device of claim 1, wherein each plate is connected to the elongated support member by a flexible connector.

21. The ocular device of claim 1, further comprising at least one additional plate, wherein at least two plates are connected to the elongated support member by a curved flexible connector and at least two plates are connected to the elongated support member by a substantially straight flexible connector.

22. The ocular device of claim 1, wherein thickness from front to back of a plate decreases with distance from a central area of the ocular device.

23. The ocular device of claim 1, wherein each plate is connected to a same side of the elongated support member.

24. The ocular device of claim 1, wherein the elongated support member is curved.

25. The ocular device of claim 1, wherein a plate is substantially circular.

26. The ocular device of claim 1, wherein a widest portion of the back surface of the at least one plate is about 2 millimeters to about 7 millimeters.

27. The ocular device of claim 1, wherein a plate is substantially circular and diameter of the substantially circular plate is about 2 to about 7 millimeters.

28. The ocular device of claim 1, wherein the elongated support member comprises an arch portion and outer sweep portions, each sweep portion extending from the arch portion.

29. The ocular device of claim 28, wherein the arch portion has a radius of curvature between about 0.0 millimeters and about 6.0 millimeters.

30. The ocular device of claim 29, wherein the arch portion is a segmental arch that is positioned in a central area of the ocular device, between the first end and the second end of the elongated support member.

31. The ocular device of claim 1, further comprising the substance in the given plate.

32. The ocular device of claim 1, wherein the given plate provides at least one pocket for holding the substance.

33. The ocular device of claim 32, wherein the at least one pocket is cylindrical.

34. The ocular device of claim 32, further comprising the substance in the at least one pocket.

35. The ocular device of claim 32, wherein the at least one pocket includes an opening configured to receive the substance.

36. The ocular device of claim 35, wherein the opening is substantially polygonally shaped.

37. The ocular device of claim 35, wherein the opening is substantially hexagonally shaped.

38. The ocular device of claim 32, wherein there is an insert in the at least one pocket and wherein the insert contains the substance.

39. The ocular device of claim 38, wherein the ocular device further comprises a retention element to retain the insert in the at least one pocket.

40. The ocular device of claim 39, wherein the retention element is a sealing membrane bonded to the ocular device, the insert, or the ocular device and the insert.

41. The ocular device of claim 40, wherein the sealing membrane includes at least one aperture.

42. The ocular device of claim 39, wherein the retention element comprises a lip at an opening of the at least one pocket.

43. The ocular device of claim 38, further comprising an orifice in the given plate, the ocular device configured to dispense the substance to the eye from the insert and through the orifice, to provide a dual direction substance delivery system.

44. The ocular device of claim 38, wherein the substance is a pharmaceutically active agent and the insert comprises, consists essentially of or consists of a composition comprising the pharmaceutically active agent and a pharmaceutically acceptable carrier.

45. The ocular device of claim 44, wherein the pharmaceutically acceptable carrier comprises a water-soluble polymer.

46. The ocular device of claim 44, wherein the pharmaceutically acceptable carrier comprises a water-insoluble polymer.

47. The ocular device of claim 44, wherein the pharmaceutically acceptable carrier forms a matrix, and the pharmaceutically active agent is dispersed within the matrix.

48. The ocular device of claim 1, wherein at least a portion of the ocular device is formed from polymeric material.

49. An ocular device comprising:
an elongated support member of flexible material; and
at least three plates, wherein a given plate is configured to deliver a substance to an eye and at least one plate is connected to the elongated support member, the at least one plate comprising a back surface, the back surface having at least one protrusion having a contact surface to contact an outermost layer of the eye and to provide an offset space between the outermost layer of the eye and the back surface of the at least one plate.

50. The ocular device of claim 49, wherein the contact surface is convex.

51. The ocular device of claim 49, wherein the elongated support member and the at least one plate are substantially coplanar.

52. The ocular device of claim 49, wherein the at least one plate is connected to the elongated support member proximate to an end of the elongated support member.

53. The ocular device of claim 49, wherein a first plate is connected proximate to an end of the elongated support member and a second plate is connected to the elongated support member proximate to another end of the elongated support member, the elongated support member and the first and second plates being substantially coplanar.

54. An ocular device comprising:
an elongated support member;
at least three plates, wherein a given plate is configured to deliver a substance to an eye and a first plate is connected proximate to an end of the elongated support member and a second plate is connected proximate to another end of the elongated support member, wherein the first plate and the second plate are substantially coplanar with the elongated support member; and
the first plate and the second plate comprise a back surface, each back surface having at least one protrusion having a contact surface to contact an outermost layer of the eye and to provide an offset space between the outermost layer of the eye and the back surface.

55. The ocular device of claim 54, wherein at least one contact surface is convex.

56. The ocular device of claim 54, wherein the substance is a pharmaceutically active agent.

57. The ocular device of claim 56, wherein the pharmaceutically active agent is disposed within the given plate.

58. The ocular device of claim 54, wherein at least a portion of the ocular device is formed of the substance blended with other material.

59. The ocular device of claim 54, wherein the given plate provides a pocket capable of receiving the substance.

60. The ocular device of claim 59, further comprising the substance in the pocket provided by the given plate.

61. The ocular device of claim 59, further comprising a removable insert in the pocket provided by the given plate, wherein the insert is capable of containing the substance.

62. The ocular device of claim 61, further comprising a retention element to retain the insert in the pocket provided by the given plate.

63. An ocular device comprising:
an elongated support member; and
at least three plates, wherein a given plate is configured to deliver a substance to an eye and at least one plate is connected to the elongated support member and the least one plate includes (i) a contact surface with at least three points configured to contact an outermost layer of the eye and (ii) a remote surface configured to be maintained remote from the outermost layer of the eye by the at least three points, the remote surface and the at least three points providing an offset space configured to retain a tear fluid.

64. The ocular device of claim 63, wherein the substance is a pharmaceutically active agent.

65. The ocular device of claim 64, wherein, when the ocular device is placed under an eyelid, the pharmaceutically active agent is delivered to the eye by the tear fluid.

66. The ocular device of claim 63, wherein surface area of the contact surface is less than about 20% of surface area of the remote surface.

67. The ocular device of claim 63, wherein the ocular device is flexible and adaptive to the contact surface.

* * * * *

UNITED STATES PATENT AND TRADEMARK OFFICE
CERTIFICATE OF CORRECTION

PATENT NO. : 12,257,184 B2  
APPLICATION NO. : 17/076634  
DATED : March 25, 2025  
INVENTOR(S) : Denis LaBombard Page 1 of 1

It is certified that error appears in the above-identified patent and that said Letters Patent is hereby corrected as shown below:

In the Claims

In Column 64, Lines 39, Claim 11 please delete "of the eye".

Signed and Sealed this  
Twenty-seventh Day of May, 2025

Coke Morgan Stewart  
*Acting Director of the United States Patent and Trademark Office*